United States Patent
Dunham et al.

(10) Patent No.: US 9,670,495 B2
(45) Date of Patent: Jun. 6, 2017

(54) PAN-YEAST AUTONOMOUSLY REPLICATING SEQUENCE

(71) Applicant: UNIVERSITY OF WASHINGTON THROUGH ITS CENTER FOR COMMERCIALIZATION, Seattle, WA (US)

(72) Inventors: Maitreya Dunham, Seattle, WA (US); Ivan Liachko, Seattle, WA (US)

(73) Assignee: UNIVERSITY OF WASHINGTON THROUGH ITS CENTER FOR COMMERCIALIZATION, Seattle, WA (US)

( * ) Notice: Subject to any disclaimer, the term of this patent is extended or adjusted under 35 U.S.C. 154(b) by 20 days.

(21) Appl. No.: 14/770,074

(22) PCT Filed: Feb. 25, 2014

(86) PCT No.: PCT/US2014/018446
§ 371 (c)(1),
(2) Date: Aug. 24, 2015

(87) PCT Pub. No.: WO2014/131056
PCT Pub. Date: Aug. 28, 2014

(65) Prior Publication Data
US 2016/0002647 A1    Jan. 7, 2016

Related U.S. Application Data

(60) Provisional application No. 61/769,085, filed on Feb. 25, 2013, provisional application No. 61/784,975, filed on Mar. 14, 2013, provisional application No. 61/868,749, filed on Aug. 22, 2013.

(51) Int. Cl.
| | |
|---|---|
| *C12Q 1/68* | (2006.01) |
| *C12Q 1/00* | (2006.01) |
| *C12N 15/81* | (2006.01) |
| *C12N 15/69* | (2006.01) |

(52) U.S. Cl.
CPC .......... *C12N 15/81* (2013.01); *C12N 15/69* (2013.01); *C12N 15/815* (2013.01)

(58) Field of Classification Search
None
See application file for complete search history.

(56) References Cited

U.S. PATENT DOCUMENTS 4,837,148 A    6/1989 Cregg

OTHER PUBLICATIONS

Sikorski et al. A System of Shuttle Vectors and Yeast Host Strains Designed for Efficient Manipulation of DNA in Saccharomyces cerevisiae. May 1989. Genetics Society of America. vol. 122, pp. 19-27.*

Darby et al. Which Yeast Species Shall I Choose? Saccharomyces cerevisiae Versus Pichia pastoris (Review). 2012. Recombinant Protein Production in Yeast: Methods and Protocols, Methods in Molecular Biology. vol. 866, pp. 11-23.* pRS406 (ATCC 87517). ATCC Product Sheet. printed on Dec. 19, 2016, 2 pages.*

Meyer J. et al. Galactokinase encoded by GAL1 is a bifunctional protein required for induction of the GAL genes in Kluyveromyces lactis and is able to suppress the gal3 phenotype in Saccharomyces cerevisiae, Molecular and Cellular Biology, 1991, vol. 11, No. II, p. 5454-5461, especially abstract, fig 2 (EMBL-Bank: M74111, Aug. 31, 2006).

Liachko I. et al. A comprehensive genome-wide map of autonomously replicating sequences in a naive genome, PLoS Genetics., 2010, vol. 6, No. 5: e1000946. doi:10.1371/journal.pgen.1000946, p. I-12

Liachko I. et al. Novel features of ARS selection in budding yeast Lachancea kluyveri. BMC Genomics, 2011, 12: 633.doi:IO.II86/I47I-2164-12-633, p. I-18.

Written Opinion of the International Searching Authority, and International Search Report related to corresponding PCT International application No. PCT/US14/18446, 6 pages.

Boer, Erik, et al., "Yeast expression platforms", Appl Microbiol Biotechnol (2007) 77: 513-523.

Brewer, Bonita J. et al., "The Localization of Replication Origins on ARS Plasmids in S. cervisiae", Cell, Nov. 6, 1987, 51: 463-471.

Broach, J.R. et al., "Localization and Sequence Analysis of Yeast Origins of DNA Replication", Cold Spring Harbor Symposia on Quantitative Biology, 1983, 47: 1165-1173.

Chee, Mark K. et al., "New and Redesigned pRS Plasmid Shuttle Vectors for Genetic Manipulation of Saccharomycescerevisiae", G3 (Bethesda). May 2012;2(5):515-26.

Chuang, Ray-Yuan et al., "The fission yeast homologue of Orc4p binds to replication origin DNA via multiple AT-hooks", PNAS, vol. 96(6): 2656-2661.

Cregg, James M. et al. "Pichia pastoris as a host system for transformations", Mol Cell Biol. Dec. 1985;5 (12):3376-85.

Database EMBL, "Kluyveromyces lactis galactokinase (GAL1) gene, complete cds.", XP002750737, retrieved from EPBI accession No. EM_STD:M74508, Database accession No. M74508, Feb. 4, 1992, 2 pages.

Dershowitz, Ann et al., "Linear Derivatives of Saccharomyces cerevisiae Chromosome III Can Be Maintained in the Absence of Autonomously Replicating Sequence Elements", Molecular and Cellular Biology (Impact Factor: 4.78). Aug. 2007; 27(13):4652-63.

(Continued)

*Primary Examiner* — Channing S Mahatan
(74) *Attorney, Agent, or Firm* — Karen S Canady; canady + lortz LLP

(57) ABSTRACT

A DNA sequence that functions as an origin in many different yeast species. From 1 to 17 mutations can be introduced into this sequence to improve its function across multiple yeasts. The resulting synthetic DNA sequence confers stable plasmid replication function in all yeast species tested, including but not limited to *Saccharomyces cerevisiae, Lachancea kluyveri, Kluyveromyces lactis, Kluyveromyces wickerhammii, Hansenula polymorpha*, and *Pichia pastoris*. Also provided are sequences that function as an optimal origin in the industrially useful *Pichia pastoris*.

20 Claims, 12 Drawing Sheets

(56) References Cited

OTHER PUBLICATIONS

Di Rienzi, Sara C. et al., "Maintaining replication origins in the face of genomic change", Genome Research, Jun. 4, 2012; 22:1940-1952.
Donato, Justin J. et al., "Genome-Wide Hierarchy of Replication Origin Usage in Saccharomyces cerevisiae", PLoS Genetics, Sep. 2006; 2(9):1328-1338.
Dujon, Bernard et al., "Genome evolution in yeasts", Nature, Jul. 1, 2004;430(6995):35-44.
Fowler, Douglas M. et al., "High-resolution mapping of protein sequence-function relationships", Nature Methods, Sep. 2010; 7(9):741-748.
Fowler, Douglas M. et al., "Enrich: software for analysis of protein function by enrichment and depletion of variants", Bioinformatics, 2011; 27(24):3430-3431.
Iborra, Francois et al., "Kluyveromyces marxianus small DNA fragments contain both autonomous replicative and centromeric elements that also function in Kluyveromyces lactis", Yeast, 1994; 10(12):1621-1629.
Iwakiri, Ryo et al., "Isolation and structural analysis of efficient autonomously replicating sequences (ARSs) of the yeast Candida utilis", Yeast, 2005; 22:1049-1060.
Lee, Charles C. et al., "An episomal expression vector for screening mutant gene libraries in Pichia pastoris", Plasmid, Jul. 2005; 51(1):80-85.
Liachko, Ivan et al., "High-resolution mapping, characterization, and optimization of autonomously replicating sequences in yeast", Genome Research, 2013, 23:698-704.
Liachko, Ivan et al., "An autonomously replicating sequence for use in a wide range of budding yeasts", Yeast Research, Dec. 2013, 14 (2):364-367.
Mechali, Marcel et al., "Genetic and epigenetic determinants of DNA replication origins, position and activation", Current Opinion in Genetics & Development, 2013, 23:124-131.
Meyer, Jutta, et al., "Galactokinase encoded by GAL1 is a bifunctional protein required for induction of the GAL genes in Kluyveromyces lactis and able to suppress the gal3 phenotype in Saccharomyces cerevisiae", Molecular and Cellular Biology (Impact Factor: 4.78). Dec. 1991; 11(11):5454-61.
Nieduszynski, Conrad A., et al., "OriDB: a DNA replication origin database", Nucleic Acids Research, 2007, vol. 35, Database Issue, D40-D46.

Parent, Stephen A. et al., "Vector systems for the expression, analysis and cloning of DNA sequence in S. cerevisiae", Yeast, Dec. 1985, 1(2):83-138.
Patwardhan, Rupali, et al., "High-resolution analysis of DNA regulatory elements by synthetic saturation mutagenesis", Nature Biotechnology, Dec. 2009, 27(2):1173-1175.
Raghuraman, M.K. et al., "Replication Dynamics of the Yeast Genome", Science, Oct. 2001, 294:115-121.
Scalfani, R.A. et al., "Cell Cycle Regulation of DNA Replication", Annu Rev Genet. 2007 ; 41: 237-280.
Siow, Cheuk C. et al., "OriDB, the DNA replication origin database updated and extended", Nucleic Acids Research, 2012, vol. 40, Database issue, D682-D686.
Smith, Duncan et al., "Intrinsic coupling of lagging-strand synthesis to chromatin assembly", Nature, Mar. 2012, 483:434-439.
Stinchcomb, D.T. et al., "Isolation and characterisation of a yeast chromosomal replicator", Nature, Nov. 1979, 282:39-43.
Stinchcomb, D.T. et al., "Eukaryotic DNA segments capable of autonomus replication in yeast", PNAS, 1980, 77 (8):4559-4563.
Vernis, Laurence, et al., "An Origin of Replication and a Centromere Are Both Needed To Establish a Replicative Plasmid in the Yeast Yarrowia lipolytica", Molecular and Cellular Biology, Apr. 1997, 17(14):1995-2004.
Walker, Scott S. et al., "A DNA replication enhancer in Saccharomyces cerevisiae", PNAS, 1990, 87(12):4665-4669.
Wilmes, Gwendolyn M. et al., "The B2 element of the Saccharomyces cerevisiae ARS1 origin of replication requires specific sequences to facilitate pre-RC formation", PNAS, Jan. 2002, 99(1):101-106.
Wright, Martin C. "Replicative transformation of the filamentous fungus Ashbya gossypii with plasmids containing Saccharomyces cerevisiae ARS elements", Gene, Dec. 1991, 109(1):99-105.
Xu, Jia, et al., "Genome-wide identification and characterization of replication origins by deep sequencing", Genome Biology, 2012, 13:R27, 14 pages.
Yabuki, Nami, et al., "Mapping of early firing origins on a replication profile of budding yeast", Genes to Cells, 2002, 7: 781-789.
Yang, Vina, et al., "High efficiency transformation of Pichia stiptis based on its URA3 gene and a homologous autonomous replication sequence, ARS2", Applied and Environmental Microbiology, Dec. 1994, 60(12): 4245-4254.
Extended European Search Report for corresponding EP Application No. 14754495.1 (EP2959001), dated Jan. 12, 2016, 7 pages.

* cited by examiner

| Plasmid 1 | Plasmid 2 | T-test Pval |
|---|---|---|
| ARS | OPT | 0.0115 |
| ARS | PARS1 | 0.0002 |
| ARS | pRS316 | 0.0310 |
| OPT | PARS1 | 0.00002 |
| OPT | pRS316 | 0.002 |
| PARS1 | pRS316 | 0.0140 |

SEQUENCE LISTING

```
<160> NUMBER OF SEQ ID NOS: 59

<210> SEQ ID NO 1
<211> LENGTH: 183
<212> TYPE: DNA
<213> ORGANISM: artificial sequence
<220> FEATURE:
<223> OTHER INFORMATION: mutated ARS

<400> SEQUENCE: 1
actttaataa ttaktttaat atttkkttct awataatgac wtttaattaa aaaagataaa      60
atataaaaac atcataataa ctcaccagag gttaagaaca aaaaaacaaa ttagatatct    120
```

```
gctaatccaa tatagttaaa tcaatctttc cttggtataa tgggtatatt acatatattt    180
caa                                                                  183

<210> SEQ ID NO 2
<211> LENGTH: 452
<212> TYPE: DNA
<213> ORGANISM: artificial sequence
<220> FEATURE:
<223> OTHER INFORMATION: mutated ARS

<400> SEQUENCE: 2
tcaacatctt tggataatat cagaatgaga agaacagat acgcagtacg ttttttggtg     60
agctctttgc acttctttag ttctttccat caatatcagt tkyttawrcw yttakgacta   120
awaktgatgt ttaacttcaa watstttaaa mttttgttct tcccgacgtt cattaagaat   180
actaatacac tttaataatt aktttaatat ttkkttctaw ataatgacwt ttaattaaaa   240
aagataaaat ataaaaacat cataataact caccagaggt taagaacaaa aaaacaaatt   300
agatatctgc taatccaata tagttaaatc aatctttcct tggtataatg ggtatattac   360
atatatttca aggaccgaca ctcctaccaa atatctaaaa tttaccatat taacataaca   420
tgtatataaa cgtcaaatca taatcagcac ta                                 452

<210> SEQ ID NO 3
<211> LENGTH: 128
<212> TYPE: DNA
<213> ORGANISM: artificial sequence
<220> FEATURE:
<223> OTHER INFORMATION: mutated ARS

<400> SEQUENCE: 3
actttaataa ttaktttaat atttkkttct awataatgac wtttaattaa aaagataaa     60 atataaaaac atcataataa ctcaccagag gttaagaaca aaaaaacaaa ttagatatct   120
gctaatcc                                                            128

<210> SEQ ID NO 4
<211> LENGTH: 116
<212> TYPE: DNA
<213> ORGANISM: Kluyveromyces lactis

<400> SEQUENCE: 4
aacatcataa taactcacca gaggttaaga acaaaaaaac aaattagata tctgctaatc    60
caatatagtt aaatcaatct ttccttggta taatgggtat attacatata tttcaa       116

<210> SEQ ID NO 5
<211> LENGTH: 100
<212> TYPE: DNA
<213> ORGANISM: artificial sequence
<220> FEATURE:
<223> OTHER INFORMATION: mutated ARS

<400> SEQUENCE: 5
gttgggawtc gaaccywmga yckswcsctt gcaaggggag cgcgctacca actacgccac    60
acgcccgaat aatacaaact aggataatgg agtaattata                         100

<210> SEQ ID NO 6
<211> LENGTH: 183
<212> TYPE: DNA
<213> ORGANISM: artificial sequence
<220> FEATURE:
<223> OTHER INFORMATION: mutated ARS
```

<400> SEQUENCE: 6

```
actttaataa ttattttaat attttgttct aaataatgac ttttaattaa aaaagataaa    60
atataaaaac atcataataa ctcaccagag gttaagaaca aaaaaacaaa ttagatatct   120
gctaatccaa tatagttaaa tcaatctttc cttggtataa tgggtatatt acatatattt   180
caa                                                                183
```

<210> SEQ ID NO 7
<211> LENGTH: 452
<212> TYPE: DNA
<213> ORGANISM: artificial sequence
<220> FEATURE:
<223> OTHER INFORMATION: mutated ARS

<400> SEQUENCE: 7

```
tcaacatctt tggataatat cagaatgaga agaacagat acgcagtacg ttttttggtg     60
agctctttgc acttctttag ttctttccat caatatcagt tttttaaact tttaggacta   120
aaagtgatgt ttaacttcaa aatgtttaaa attttgttct tcccgacgtt cattaagaat   180
actaatacac tttaataatt attttaatat tttgttctaa ataatgactt ttaattaaaa   240
aagataaaat ataaaacat cataataact caccagaggt taagaacaaa aaacaaatt    300 agatatctgc taatccaata tagttaaatc aatctttcct tggtataatg ggtatattac   360
atatatttca aggaccgaca ctcctaccaa atatctaaaa tttaccatat taacataaca   420
tgtatataaa cgtcaaatca taatcagcac ta                                 452
```

<210> SEQ ID NO 8
<211> LENGTH: 118
<212> TYPE: DNA
<213> ORGANISM: artificial sequence
<220> FEATURE:
<223> OTHER INFORMATION: mutated ARS

<400> SEQUENCE: 8

```
actttaataa ttattttaat attttgttct aaataatgac ttttaattaa aaaagataaa    60
atataaaaac atcataataa ctcaccagag gttaagaaca aaaaaacaaa ttagatat     118
```

<210> SEQ ID NO 9
<211> LENGTH: 100
<212> TYPE: DNA
<213> ORGANISM: artificial sequence
<220> FEATURE:
<223> OTHER INFORMATION: mutated ARS

<400> SEQUENCE: 9

```
gttgggattc gaaccttcga tcggacgctt gcaaggggag cgcgctacca actacgccac    60
acgcccgaat aatacaaact aggataatgg agtaattata                         100
```

<210> SEQ ID NO 10
<211> LENGTH: 183
<212> TYPE: DNA
<213> ORGANISM: Kluyveromyces lactis

<400> SEQUENCE: 10

```
actttaataa ttagttttaat atttgtttct atataatgac atttaattaa aaaagataaa   60
atataaaaac atcataataa ctcaccagag gttaagaaca aaaaaacaaa ttagatatct   120
gctaatccaa tatagttaaa tcaatctttc cttggtataa tgggtatatt acatatattt   180
caa                                                                183
```

```
<210> SEQ ID NO 11
<211> LENGTH: 452
<212> TYPE: DNA
<213> ORGANISM: Kluyveromyces lactis

<400> SEQUENCE: 11
tcaacatctt tggataatat cagaatgaga aagaacagat acgcagtacg tttttggtg      60 agctctttgc acttctttag ttctttccat caatatcagt tgcttatgca cttatgacta    120
atattgatgt ttaacttcaa tatctttaaa cttttgttct tcccgacgtt cattaagaat    180
actaatacac tttaataatt agtttaatat ttgtttctat ataatgacat ttaattaaaa    240
aagataaaat ataaaaacat cataataact caccagaggt taagaacaaa aaaacaaatt    300
agatatctgc taatccaata tagttaaatc aatctttcct tggtataatg ggtatattac    360
atatatttca aggaccgaca ctcctaccaa atatctaaaa tttaccatat taacataaca    420
tgtatataaa cgtcaaatca taatcagcac ta                                 452

<210> SEQ ID NO 12
<211> LENGTH: 128
<212> TYPE: DNA
<213> ORGANISM: Kluyveromyces lactis

<400> SEQUENCE: 12
actttaataa ttagtttaat atttgtttct atataatgac atttaattaa aaagataaaa     60
atataaaaac atcataataa ctcaccagag gttaagaaca aaaaaacaaa ttagatatct    120
gctaatcc                                                            128

<210> SEQ ID NO 13
<211> LENGTH: 100
<212> TYPE: DNA
<213> ORGANISM: Pichia pastoris

<400> SEQUENCE: 13
gttgggaatc gaacccaaga cctctcccct gcaaggggag cgcgctacca actacgccac     60
acgcccgaat aatacaaact aggataatgg agtaattata                          100

<210> SEQ ID NO 14
<211> LENGTH: 99
<212> TYPE: DNA
<213> ORGANISM: Pichia pastoris
<220> FEATURE:
<221> NAME/KEY: misc_feature
<222> LOCATION: (70)..(91)
<223> OTHER INFORMATION: n is a or g or c or t

<400> SEQUENCE: 14
ttgggaatcg aacccamgay ckvwcsmtyg cahrkbghgc gcgmtaccaa ctacgccaca     60
ckcccbmhyn mtacharywn ndddddddnd nwhwtwwww                           99

<210> SEQ ID NO 15
<211> LENGTH: 99
<212> TYPE: DNA
<213> ORGANISM: Pichia pastoris

<400> SEQUENCE: 15
ttgggaatcg aacccaagac ctctcccttg caaggkgwgc gcgctaccaa ctacgccaca     60
cgcccgaata mtacaaactr rradrrkrrr dwawttata                           99
```

<210> SEQ ID NO 16
<211> LENGTH: 99
<212> TYPE: DNA
<213> ORGANISM: Pichia pastoris

<400> SEQUENCE: 16
agatatcgtg cgaataaaca tgaatgtttc atatttatca attacgctca ctattaaatt    60
gtgagaatca tattataaat catgctatat atttattct                           99

<210> SEQ ID NO 17
<211> LENGTH: 101
<212> TYPE: DNA
<213> ORGANISM: Pichia pastoris
<220> FEATURE:
<221> NAME/KEY: misc_feature
<222> LOCATION: (31)..(84)
<223> OTHER INFORMATION: n is a or g or c or t

<400> SEQUENCE: 17
wkatathktd cgaawaaahw tkwvtbtwtc ntrbkwnwmd wdkdcgsckm rvnnnkvvnt    60
ctbtdmdaww hwwattataa athnwrctat atattwattc k                       101

<210> SEQ ID NO 18
<211> LENGTH: 99
<212> TYPE: DNA
<213> ORGANISM: Pichia pastoris

<400> SEQUENCE: 18
wkatathktg cgaawaaaha tkwatktttc dtabdthwma attdcsckmr vdhdtvvmtt    60
btdmraathw wattataaat hdtgctatat attwattct                           99

<210> SEQ ID NO 19
<211> LENGTH: 99
<212> TYPE: DNA
<213> ORGANISM: Pichia pastoris

<400> SEQUENCE: 19
ttttaaatta cgaaaaaaat gttgattatc gtgggacaat tagtgccgag ggtgggcccc    60
tcacaataat aattataaat ataactatat attaattcg                           99

<210> SEQ ID NO 20
<211> LENGTH: 348
<212> TYPE: DNA
<213> ORGANISM: Pichia pastoris

<400> SEQUENCE: 20
ccgatcgtct tccgaatgga catccagatt atgtcaaact cattcttaca agcagagtct    60
atgatgttac agacgaaagt cctatcacac acgccgttaa cctttcacag aaaaccaata   120
gtaacgttgt tttgaaaaga gaagacctcc ttccagtatt ctcgttcaag ctacgtggag   180
cttacaacat gatcgcccaa ctgtcgccag agaagcgtag taaggtgtt gtgggttgct    240 ctgcaggcaa ccatgctcag ggaattgcat ttagcgccaa aaagctggga atacctgcca   300
ctattgtgat gccaactgcc actcctagta tcaagtatca gtcagtgg                348

<210> SEQ ID NO 21
<211> LENGTH: 190
<212> TYPE: DNA
<213> ORGANISM: Pichia pastoris

```
<400> SEQUENCE: 21
ctctttgaat gctgtaaaga ggtcttaatt cttgttcagc ttcaaaccta tcagactcat      60
ccaacaaatt ttgccacaat gtttgcttgg ccttccttac tacttgatct ggcgtcagtt    120
ctagtaatga tagccatccg tggtccttga attcatctct atgcaaatgc ttcgcattcc    180
aaatattaag                                                            190

<210> SEQ ID NO 22
<211> LENGTH: 953
<212> TYPE: DNA
<213> ORGANISM: Pichia pastoris

<400> SEQUENCE: 22
cttgatgtga cgtataagca tgcacagcag gtgtaccatg atccgatcct gttccatgca     60 caagggtaa atatatcatt ttctctttag gcgcggaaga tttcgaaaga aggtgtgtc     120 caagggatcg ttcacgatgg tagcaaacgt ttcgtaaagt ttcgtgattc taatctagta    180
tagtcagggc gatcaatagc atcaaacaat tctgatggtc ttgtcagaaa atactcgaac    240
gctgtaattg atgctgaaga taaataatgc tgtcacatgt actggaagat accttcttct    300
tggcggcagt tcaatttggc gtggttggcg ataatgaaag taattataga cattagagat    360
actaagacaa ctccaatcag aattgctgcc ccataattgc tccaatatat gtacataaaa    420
aaaaaatgag aatgacttca tattcttgga aaggccaatg ataatttaga ctgaaaaaaa    480
aatattgtac aaaatagtaa ctaagaaagt acttcttcgg agtactaaaa cgccagcaat    540
tgaactagaa tgtacataga cgtgtttgtg gtaagatgcc tcaaattggc tataacatgc    600
aaattctttc tgagagtcac tagaacaagg ttgtgcatac tgcataattc ccaattgaga    660
tatatgatct accttgcagc aaggctgaga acactttata taggatattc caatattatt    720
tactgttgtt caaaattgaa actcttttt aactctcctt catctttagg tatacataca    780
tatctttgcc ggctttcaat atccaaacca cagaaaccgc ctattcaaac agtacttaac    840 ttcgttttcca aggctatatt ttccaacaac acttatatcc aactttgatc acccgcccgc    900
aatgcggttg tacttagcaa cattaggaac tccgctcact ggtacaacgc cag           953

<210> SEQ ID NO 23
<211> LENGTH: 301
<212> TYPE: DNA
<213> ORGANISM: Pichia pastoris

<400> SEQUENCE: 23
ctcaccaatc aacagaatac gaactggata cctttagtgt taaattgtat gaagataaga     60
tcaacttggc atcaaaaata gggcgacctg tgctggaccc gatatctcgt tgggactttg    120
acgttgaaga actaccatac gctccaattg tgaaaataat agattttat gagtttgatg     180 gtactctttt caaatcccca gttttaaatg atgaactgtt ccgtcgtagt tcgatacata    240
tgatagaatc aggagcaggg ctaagagata ttgactggtg gaactttcat gaagcctgga    300
g                                                                    301

<210> SEQ ID NO 24
<211> LENGTH: 504
<212> TYPE: DNA
<213> ORGANISM: Pichia pastoris
```

<400> SEQUENCE: 24

```
ctattgccaa cattgcatga tctcttacgc cactatgaag agatgcacat tcagccctcg      60
cctccagaaa tggagacacc caggtcaaag gcggtcaata gtattttgga cactgtatca     120
acgaatgagg tgttttatc ccatcaagga atggagccac aatttcaagt tccagagttt     180
gactttgccg tcacgaataa ctttcaaaat cagcattctg aaacttctgg cgtggatgat     240
cccacaccta aaactcagcc tggagcgact gtaggtgctg gcctcaatc tcaaatacgg     300
cagggccagc accaacagca acaatttcct atggacgaag atgaagatac ggaaatgtgc     360
attgatgacc ccgctcgtca tctatacgtt agtgaacaca cgaacatag accttttaaa     420
tgtcctgttg ttggatgcga taagacctac aagaaccaga acggtctcaa ataccatcgt     480
cttcacggcc atcagaatca aaag                                            504
```

<210> SEQ ID NO 25
<211> LENGTH: 190
<212> TYPE: DNA
<213> ORGANISM: Pichia pastoris

<400> SEQUENCE: 25

```
ctctcatcca gttcttatta cctctcaatg tattgatctc accattatgg gcagcccaac      60
gcaaaggttg agccctatcc caagatggaa aagtgtttgt agagaaacgg gagtgcacca     120
gagcaaaatg ggattcgtac tccacattga ccaaatcatg atagtagtta aatacctggg     180
caggagtaag                                                            190
```

<210> SEQ ID NO 26
<211> LENGTH: 437
<212> TYPE: DNA
<213> ORGANISM: Pichia pastoris

<400> SEQUENCE: 26

```
ctgcaaaccc aaaaattggc cctcctgaaa agagacacca taagatggca cagctgactt      60
gggccaatct tttattccgt ggtacttgga agtaaaacat agtgtttaga aatgaatgtt     120
caaccttgag gttttttttc aatgtactta gttgaaaata ggaagggaac gatgatgggg     180
ttgtatgaaa gttgaatgga gtgtgataag gatatcgtaa tgcgcgaact tccgagttaa     240
tgcataagtg ttgtaaaaaa aaagataca ttaacagata gggagggatt gccggcaatt     300
gccgctgtga tgaagtcgaa ccctttttct tctattggag gtagagtcac cagtcactga     360
atggctctgc gctggaaaag tcatcgttct agttttgttg tctttccatt ttggtcggat     420
tataccgtat tccggag                                                    437
```

<210> SEQ ID NO 27
<211> LENGTH: 159
<212> TYPE: DNA
<213> ORGANISM: Pichia pastoris

<400> SEQUENCE: 27

```
ctcttttccc tgtaatcaag gttaagcata tatagaattg tttaaatcat gatagtagtc      60
ttacgtaggc caaaaccaaa gcaaacgtac cagtgcacac acctatcaac cactgtagga     120
cttgtgtctt tgtagagtca atttgcacct tcatgttag                            159
```

<210> SEQ ID NO 28
<211> LENGTH: 216
<212> TYPE: DNA
<213> ORGANISM: Pichia pastoris

<400> SEQUENCE: 28

| | | | | |
|---|---|---|---|---|
| cccatttgtc | aaagctttgc | actaagttgt | aacgtaattc | taagttgtgg tgctgaggga | 60 |
| tgcgggattc | ttgttgagcg | tcattctctg | tgggcatcca | aaagcacagc cgtccgccta | 120 |
| ccggcaatct | ttcagatgca | aattgtagaa | gatcatccag | taaagcgtcc aattcataag | 180 |
| gtttcttagg | ttgaatataa | tctcgtctgg | tgtggg | | 216 |

<210> SEQ ID NO 29
<211> LENGTH: 1001
<212> TYPE: DNA
<213> ORGANISM: Pichia pastoris

<400> SEQUENCE: 29

| | | | | | |
|---|---|---|---|---|---|
| cccaggcttt | cttttcgcg | atggtttcc | atcctttatt | cgcctgggtc ctcatacaat | 60 |
| tttgactttt | gtagctttgg | aacaattgag | aacatggcgg | attgccatgt agactatcac | 120 |
| ttggctagtc | ggttccattt | ctgatagtaa | tagatataaa | tataaattag ctatttattg | 180 |
| attgacactt | attgctaaac | cattgatgat | gttcctggtt | tacttacatt tgctacagaa | 240 |
| aaccgcgatt | cttatcagtt | ttcatgtctc | aagcgaacaa | gaacttgaaa caattctaat | 300 |
| tcacctgaaa | gattgtataa | aagtggtgcc | aacaattaaa | tcgtgtcgtt gttttcttcg | 360 |
| caaactatga | tttctcagta | agttaatcaa | aaacatcaat | agcaatcaaa actcaaataa | 420 |
| agctctaaca | ttagactctt | gcgtgtgcac | aaaactctga | tgagaatctt gcagggata | 480 |
| tctcataatg | cgttacattc | caattggaca | tctatctgta | atcaaatagg ctcctcccaa | 540 |
| agaaaactct | cttcattatt | ggagcaagga | attgatcaaa | atgatcaaac tttacgtgaa | 600 |
| attcttgtcc | aaattaatag | gatgtgcaga | gcgatcgctt | taatgttgga aaataagaga | 660 |
| atgctcaaga | acgacgtgga | aattatcctg | caacaaatat | tagatagtaa tagtactgag | 720 |
| agaaaagaa | ggttgccaag | ggaaaaggtt | agaatacttg | aaaattggtt tgcggatcac | 780 |
| ttccaacatc | catacgcgac | gcagcaagat | tttgatgagc | tagtgcacct gacatctctt | 840 |
| agcaaaactc | aaatcagaaa | ttggatctca | aacaaaagac | gaaaggaaag atcttcaact | 900 |
| gtttctacag | agctacttca | agcattaaac | aaatcacccct | cgtaaatata ataatttat | 960 |
| tgaatggtta | gctattgtga | atttaaaatt | gacgtatgtg | g | 1001 |

<210> SEQ ID NO 30
<211> LENGTH: 3826
<212> TYPE: DNA
<213> ORGANISM: Pichia pastoris

<400> SEQUENCE: 30

| | | | | | |
|---|---|---|---|---|---|
| ctctgcttag | tgatggaact | ataggaaaga | actgcaatgc | tatgcgagac acgccatttc | 60 |
| gggtgcaatg | aattttctgg | aattgatgaa | ttggcgttcc | gctttaacat gacaggtgaa | 120 |
| aactaattat | gcagattagg | tattagaatg | ctgctgcaaa | atttcaaact gatgagtgcg | 180 |
| cttctttgta | aagtgcttaa | tgcaatcatg | cgctgcacgt | taaagtataa attccctgat | 240 |
| cgctttccga | actatgtttt | cgagatctag | atctaataga | ccgtattcga tatttatttt | 300 |
| tgtttcgact | ctgcttatat | tcacgctatt | tacatgctac | catacttgaa tggaaaacaa | 360 |
| cttgaaattt | cattttcatg | cacctactga | accggcaatt | actaccacaa gagggcgaaa | 420 |
| attggcgttg | ttgctgattc | ttaaattgat | gactgcgcta | tgtgtattcc caaatgcaac | 480 |
| atttgcagca | ggtttaacca | aatgaatctc | tagtatactc | agccagacta atgaaaagag | 540 |
| agaccaaccct | gaaagtttga | ctaatagtca | tagagtgcca | aaattatgat cactttgttg | 600 |

```
ttcaagacat aattggtctc atgttgaaaa gcggttgtat ctatagtccg agagaatacg      660
ttctttattg aaacgctcta tatatacttg aagttgtcta tccaaatccc agaccgggtc      720
acatgtttac aggtcttttc tttttagctg cggttgtgcg tcatgcttgc catagccccg      780
tatataaaaa tctgagtatt atttgggtaa ttcgaccttt gcatcatgca ttccgtctaa      840
aataggccag atttgaatga agaataacag tggtggctgt tgcatgaatt ttgccgatga      900
tggttgaagc gttctaacaa acatcaacac ttcagtagat actccagacg cttcagtaac      960
tccagggcca gatggaaaaa tatatcgatt gtacgaatct tacttcttgt caggcgggta     1020
gttgttatct ttgagcaatt atatttattc atgcattatg aagaaatagg gacctagttg     1080
ttgtttgata attttttctg ctgtatagat ataatacgcc atgcggtagt aaacggttgc     1140
acgcaaggca ttcttaaatg caacgattct agaaatttca caatcgtcgt ctcattaccc     1200
tgcacaaaca aaatgggcca aactagttat caaaaagtaa ttcaatttca ttgctgcata     1260
aactcaaatt agttattctc tccgcttatt gtgacagagt caaagcattc gtggctaaca     1320
tgaatgaaac tctttttta cagtcccgac tcacgttcaa tgacccgccg gcttaattaa      1380
ctttcaagag ctagagtcgc ttctagtgaa cctcagatct acttgtaata tctgcacttc     1440
attgccataa aggtaatagg atcgtctgag ttttgagtac gtaatcttaa ttaattgtta     1500
cgtactttgt gcatgcagca tgcagatttc aaaatcatcc ttcagagcat tcgtcaaaaa     1560
caattgtccc gccaagaaat gagtaaatta tatttgtgct gcagcatacc ttttcagcc      1620 tacacacttc aaactatgtg gtcgtgtcac gtgtaccgga aagaaagta cttcttggct      1680 gcatctcaat ttgaatattg atcacaacag gaatcaaaga aaacaaaagg caacaagagt     1740
acgctaaatg acttattggt caaatagctg cttttatacc acatgaaata cagactaagc     1800
tagtaatacc atagtggaaa attgtgattt cctgtgcaat acttagtaaa ttctccttca     1860
aacttgtcaa gagagagcct taaataaaca catgcttacg aaaaacattt ccactactta     1920
ctcttctata tttgtatact ctctatctac gaataggcgt agttgggtct tttaaaatgg     1980
cagacacctc tttccttgtc attaatgtct atatgggaag aaacttatcg ttcggggact     2040
aaacagtaag tatcttcttg atcaattagt tcaggaccaa ttcttttgat gggtctattg     2100
ctgcgcggat agcacagtca tttgcaggat gattctaggc agagtttgac acagtacttg     2160
caactctagc ctatgacttt ttaagattag tctgtctttt cgaagaggct tgaccgctat     2220
tttgtacaga gtggcaaggg tatgcagtat atattcttgg cagaacttca cttcactaac     2280
agttgatgct gaaagaaaaa tggcatgtta ttgtatcggt agaccattct atttggttga     2340
gaagctagca aggaggaatg agctaatggt ggtaaagatg ttaccaagct gaatgaagtt     2400
atttagcagg atagggatgg aaccagccaa tgttagttgc aatgtcatac agtacttgtg     2460
ctggcgctaa aatcagtgcg atagaaagtc ctgaggcttt ttcagattgt ggaacaatcc     2520
attagtgtgt ttgattttgt tgtctacgga ggccaaagtg cgtatgaagt agaattaagt     2580
agaatttttg gaaagaacgc aaatttcgaa taatgatgaa ataatcctca gttgtgtcaa     2640
taccagatgt ttaaataaag ctttcgtatc ttcggactaa aaagaatctg tttcatcagt     2700
tcaagatggc tagcaagcag attgatatgt gagcccacaag atgagaaatc catcaaacta    2760
tataccaatc gtaaatcaga tgccgaattt aattccctta tagggttatt ttttgtggtc     2820
tcttcaaatt aatggttctc ttcggttgtc ctgaccgtag catagccaac cacaggaagt     2880
gctggaactt tatacggtaa actttgtttt tgaagccagt gacagaaaaa aaggaacctc     2940
aaacccgcaa gaaagaaatt tgttttgaac aggtttgaaa cgattatatc attgtaatag     3000
```

```
gtccaactct ggcctgactt ctaaaccaca acgaatacag tgcgaaggag aaaacaaata   3060
agaccatgtt cagataaaaa attctccatt acctccattc acaataatta attgtttact   3120
tgggttcctc gatgtagttt tgtttacttt cccgccattt acaagcagca ttttttggga   3180
atcgaacgat tggggtttca ttctgaactt taagttgaca actaccatta tcagatgacc   3240
taaattgggt tgctgcattt tcgtaataaa tcaatagatg cgttgcagta caatgtttct   3300
agtgaaaaca tacgtatcat gtttgaccca caaagtcata gcattttgaa aagcggcact   3360
gatatctcta tagccttcaa ttttaggtcc agtaattatg ctcatctaca gtctccgtat   3420
atattcaaag attatacgct gtaatttcaa gactgcatca catgcatcat gcataataag   3480
ttgatgcacc tgagtttgcg cagttcaggc tgatcgaagg acagattggg gaagtggcgt   3540
gtaaatcagc agatttcaat ataaaggcat tacaaaacag gatataaccg aactttttaa   3600
aatccacact tagtttcatg caagtgttga ataaacaaca tatgatcatc tacgcaacct   3660
caagtggtgg caacaattta attgagtgcg cagagactaa catgaatgta accagcgaag   3720
ttctagacgc gcgcgcctac attcgagaag tagacaagca aaacatattg tttgactaat   3780
cctgatgatc aacagtacta acacgggaat caaaaattga gtatag         3826
```

<210> SEQ ID NO 31
<211> LENGTH: 3000
<212> TYPE: DNA
<213> ORGANISM: Pichia pastoris

<400> SEQUENCE: 31

```
cactgcccat caatcagaag aacatttggt acttttcag  ggtaagaact tcatttacat     60
aatcatgctt tttaggatgt tccagagtgc cctgacattg gtcagaaagg aaggagaaca    120
tattaccagg gaatccactg aattttaac  ctacctgcaa atatcttact accttaatga    180
tgtcatcaaa ggtattgttg aaattgcgca ggttcctgaa atacgtaaac ctgaacattg    240
gaaagttgtg gaaacaaaca tacaaatatt ggccacttta atttcatcag aaccttataa    300
gtttcatatg gtgcacgaaa acaacttat  tgaccatgac gtaacaaaga aaccaaccctc    360
tcttattaat ccattgaatg gattactgtc taacatgtta acaaccgtaa gggccaattc    420
ttttcatttt ttaactcgtc aagtttctca gattaatttt tggagtatca atcccgaagt    480
ctcattttca gatgatttag actatctgaa actctcatcg aagagtttag aagcaattac    540
tttgagttca cagataaaaa ttggccactg gattagaaat ggatccatga ctagtaaaca    600
agcgcaattg tactgcacga ggttcactca atatggttac atagccgacg ttcatttgaa    660
ccaacttgct atactcgaag aacgcgacga tgatcgtcta ttattaaaca ttttggatag    720
attcaatcta atagattggt tctataacga tcaggacgtg cttggtactg ttttcgaaga    780
acgatctttt tacctaatga atgaattggt taagtttctt tataatatgt tttcacacag    840
agttaacttc cagtttgaat caaatttcac agagaaaacc cagtatgagg taacgcaata    900
cattttatac acgctttgta aaggatcttt gtcatttttca gatctgacag ccgactttcc    960
tatctccgtg gaagttactg tttttgacaa gatccttgat gaggttgctg tttacgaaga   1020
gcccaaaact atgaatgatt ctggaaagta ttctatcaag aaaagttatt acaaaaagat   1080
ggatccaatg tctatttatg tggactcggg tgatttcgat gatgtatcaa cagcgatagt   1140
aaaggaactt tcaattttag gaaaaataaa agaggagaat gttgtaattg aacctcagat   1200
cagtggaccg aatgaatcca acagccgtgt cttgagcaga ttgaaacggt tcttcattag   1260
caaatctgta gtcaaactgt tttataaatt gttacaatct gctctttctg agagcaatga   1320
```

```
gacctacgtc attgaacttt tacatttgat tcaagcagtt ttattagatg aacatgaatt    1380
gtacagaatc gaagatccag tgcaatactt tattcaaatt cctgtgtgtg atctactgtt    1440
atcagttgtt gagcacaatg attttcacg acctgtctgc aaaaaactga agttctattg     1500
aattggttga tccagcggga cgagtcaatc attgactcat tggttgattc ttttggtgaa    1560
aagcacattg aaaactttaa aaaatctaag ggatctcaag ttctggagac taaacgagct    1620
aaacaaaagc gtttagccaa ggagagacaa gagaagatca aatcacgatt tgctaaacag    1680
caaaagtctt tcatgaagca gaatttggac gcaaaaaaga gtgcggaaca tgtaactaca    1740
cattatccca aagacaatga aggattaggt agttcctccc aggactcttt tcatgagtgc    1800
attctttgtc aacgtgctca ggagggcaac gagatgtttg gaatccctgc atatgttgaa    1860
aaagttccca cgttttggga ttttcaacct aaggatgagt caacctatac ggaaagatgc    1920
ttaacaacca ttgaaaatca aatgaaacaa ttgcatgaag aaacggatgc caacaatgag    1980
gttagagaac atcttatta tcaaaaagat actcctgtaa aaagcatggc accgatatct     2040
tcaagacaca ttgttaagtc atgcgggcac cacatgcatt ataaatgttt ttctgagtta    2100
ctagaaaaca gcaggaagtt tagcacttgt ccgctttgtc gctctgccat taatgctttt    2160
gttccacaat ttgccatgaa aaacgatgct agccctgctt tcaggaggc tgcttcgaat     2220 attagtcact ttgaaaagtt gaatttgaat caaattgtat cgaaatatct tctcaatgat    2280
tccttcttga aatttattgc ggaagaaagt aaggaccagt tcatgtattt gaatgagttt    2340
aaagacattt tgaaagacgc cccagatgct tctgaccaca tgttgagtga agggttattt    2400
ccctcatttt tggccatgtc aacattattg ggtaataccc tagcaaatac tgaaattcgt    2460
ctcagattat cccccgagaa gattccccag aaaggaaact tgaagagaaa agattcggaa    2520
ttaataacct cattacttca atgtgtctcg gttatctcaa tcttattgaa acaatcttat    2580
cctgaagagc agtatctgtc tccatttttg aataaaccaa attcattaat tattgatttt    2640
gccatttcac ttctacttgg aaaagaagac tcacttcaag aaactattgt gggcatttac    2700
aagcaaacaa ttctgcattc attgaattta ctattgacta acgttggaga taatgagcat    2760
ttcagaagga tgctgagcgg tgcaaactct attattaatg attcagaact ggccattttc    2820
aaaaagtttg tgtcaacggc cacttttacc tctgatgttt cattcattac ttgcaacgaa    2880
caattattgg ttggactgta tattcttttg gagaaaacca ccacagtgta tcttaaacag    2940
ttgtttctga taatcagcat gtgcagaccc ttggacttat gcctaaatcg tgactacgag    3000

<210> SEQ ID NO 32
<211> LENGTH: 3000
<212> TYPE: DNA
<213> ORGANISM: Pichia pastoris

<400> SEQUENCE: 32
tttcctctat catttaactc taataccgga gttatagaag tagagagaat agtagtagag      60
cgtaaattca aggaaaatca agtacaagga gaccctccct ctcaagatag atttaaaatg     120
cagcctcata gtcaacaaa ctctggatgc ctaacttgcc gcaaaagaca agtcaagtgt      180
gacgaacgca agccgttttg tctaaactgt gaaaaaagcg aacagaagtg tactggtttt     240
acccatttat ccaaagatct cccttccagt tcctcttctc tcagttcaga tgactcttat     300
aaatcgatac tattaatcaa tggtctgaaa acttatctat tcaagaagcc gaagaaggtg    360
aaaactttcg ataaatctgg aatccaatgt tcgtatttgt cgcctaatgc ttcggaaatt     420
gaactgattg agctagaaat gacaatgtca gattttactt ctttgattga ttcgttggag     480
```

```
cttttttttg agcagctgaa agttgtgaat catccgaaga tggatatagc taaggagaaa        540
acagttttcc ggacctcatt caactccaga atcctgtcca ggaatcccag ggctcttggt        600
tcccaaacag gggcaatgtt ttcccattcg tcactagtct catttcttag aataaactct        660
gtttcatttc ttttgaaaga agctttgaat ggatttggtg atgtctctgg tagaataaag        720
tctattaatt gtaactttca tgttaaaggc tttcaagact ttttttgttgg gagcttagac       780 gttgctagaa tccacaaatt atcgtcccaa ttgatactgg agaaagttga tgctccagga       840
aacaaaaaac caatgctaat tgctaggttg aaatcatcgt ctctgacgat ccaactggct        900
gattgtcttg ctcattatta cggtgaatgg ttctcattct tgcaccaatg caatatgaag        960 gaagggaaa ttgtgaagcg ccaagaagat attggtccca agatagagc tcgtgattca         1020 aacaactttg tcatcagtct ccacctaaac aatataatta ttgaattgaa tccagtaagc       1080
ttgaaaagta agctgttttt gttcatcaag aaaggatgtg gaactgtgac ttttggttct       1140
caaagacttt caatctcatc gtctctaact gagattacgc ccttactgat agatgataca       1200
aagaatctaa agaatgagat aaaactggat tcaaaaaact cacatccttt gggtaattct       1260
ttcttgctgt tgcttatgga catgggatat atctctatgg ggatgctttc ctcggtctcc       1320
gtttcttttg aaactgagag cagcgcatct ctgatagcac ctgttaatgt aaatgttatg      1380
tgtgatactt acgtctcga tatatgtgct gactccttac agtgtttgct taacttaatc      1440
aaagatttaa acaaccgat aatagttcca tttgaacaaa agtacaggac acaacctgaa      1500
actcctttgg atgctcttaa agacgttgac tttgatgcat tcttccaca gaaaacaaaa        1560 gactcaaata atgttgctgc gacaaaaaca cgtacctttt cagaaacagc gttgaatggt      1620
gcattcagac caaaagtgta ttcggacggt tcgttggaga taattgataa ctactacgaa      1680
catgaatctg tgaatcaagg gttagacaat cgcacttatg gggatcttga agtctttgaa      1740
gagaactccg aagatgacat ttctttggaa aactctctca acatgaaaca tgatcacttt        1800
taccatactt cttttatgga taatacaaga aacacagaac atgtgccttt caaacttaat        1860
cttagtgttg aagctgtata catcaggtta tttgatggtt atgattggaa ggaaactcga        1920
gtatcgattt tgaacgcagt gcgaagagtt gaagccaaag cagctgcaga gctttccaga        1980
attgagaaga ttaggaatac caagttgcgg agagattcct cagcctccaa ctctggtaat        2040
gaaggctctc ttcaaactga tgatgactct gccacgagtg gttccgtctc ggaaccagtg        2100
atagaagaaa ccctttatca atccatacat ttatccctcc cagttggaat ggagccaact        2160
ttgttagctg aaagggtcaa caatgatgta aacttcaaaa gagctagttc agattctcta        2220
gacaagacac agtctccaag ttctgtcagt tcaaagtcgc aggtatcgtc tccacaaact        2280
agacgcctga aactcaagag gtccactttt cataaagttg ccttggaatt acgaaatctg        2340
agcataactt tcaagctgtt aagttctttt gatcccacaa caatcaaaaa taaatcgagt        2400
attcgaaatc ccaactcagc agagattgtc aatagaattt ctgttgaggt ggatgatttc        2460
ttaattactg ataatattcc cacctcaaca tggaaaacat tgtaacata tttgaaggaa        2520 gctgggtcta gagagttgaa ttcaaagatg gtccatctgg atattgctac aattagaccc        2580
actaggttgt tggccactac agagatgaga atagagacta cgtgttacc attgaggcta         2640 tatgtagacc aagacaccct tgacttttg actaggtttg gagagtttaa ggacttgagg        2700
tttgttcctc aagtggtcga tgacgatgat ctttttgtgt ctaaacttca cgttttccca        2760
gttcgtctaa agttagatta taaacccaag acgttgatt atgcaggaat aagatctgga        2820
aagactagtg agtttatgaa ctttttttata cttgatgagg cttcaatggt tcttcgagat        2880
```

```
gttgtactgt atggggttaa aataaccaag ttaaatccca tactaaacgg aatatggaca    2940
cctgatatta ctcgcaatca actgaaaggt gttctttcgg ggttagcatc tatcaactcg    3000

<210> SEQ ID NO 33
<211> LENGTH: 3000
<212> TYPE: DNA
<213> ORGANISM: Pichia pastoris

<400> SEQUENCE: 33
catcaattat gagtattttg agagctatct ggctccactt atcatcacac tacacgaaat      60
tccaagtttc cggaacctga ttttcaaatt agagtctttc aatgattatg ggtatgaaaa     120
aaattggtgg aaggataaag atatcaagat cgctggatcg taggaaata ggtttgttat      180 ggagttacaa agagtagtcg ccttcttgga caatgcaccg tcaaaaagat tttttgctag     240
tattcataac ctggttcaac atttgagtaa agatctgctg gcaggtttga atgatatgga     300
gggagttgaa gatttttttc ctgccttttt taaatcactc tcaggcgctg ctactggcgt     360
tgataatgag aaactacaga ggttattcca aagtgaaata attgagatct ataatggaga     420
agaacgtgaa aaacaggtag tagaatgttt tactattgaa ccagatgttt tgaagtgtaa     480
catttatcag acattccata agttgctgtg ggaaaatgat tttgaaagat gggaatgat      540 acatatcaac cgtttaagtg aggtcatggt cattcctatt tgggaaaacc tgaatgaaag     600
cgtttatggt agttttcag tttcagagat attttaccct caaatttatc taaaagagaa      660
cgaacagttg atgagatcta aaattgagct gagacaggag ttgatcaacc aaaggttgag     720
caattccaag aaaatcatgg atatttcaag ttatcaaggc aaaagggtta atgattttt      780 gtccacaacg gtcgaatact tgcaaaataa agcagaggat gaagaaatcc aaaggccttt     840
acaaaacatc aatcagatca aagataacat aatcaaggaa aaattgtcaa taactgacca     900
acagaatgct attgtggaga aattaaacag taatatggac ctgttcaata tcccagggat     960
agtgaaggaa gaaaaattag actgggaacc gtattttctt acctcaatag ttcttgatac    1020
ttccaacatt tattatttta ccaaaaactt tgaatcgaag gaaacagatt actgttggta    1080
tcaggttcga tatttccata gagagcattc gaagagggtc tccaatttca acattagaaa    1140
aataatggac ttttccgaga ttcagaatac aatccatgag tttacgcgct cgggtatttc    1200
aaacacgatg accttaacat atgtgaaaag atcagccttt tttgacgaag atccattgga    1260
cgtattgcca aacaatttag tcaagttttt caacagggac aacgagcaat agcggaaaa    1320 cttacgtgaa aactctgacg aggaatcgga agtcatcgat ctaactagag acagtgacag    1380
ctacgaagaa tttgactcct ctgctgaatc aaatggtgaa tcggcccggc gcatttgaag    1440
gagccgtgtt aattccggga cctgttagag gctgaacaaa gggttgacaa taaaggagag    1500
acacctcact cataatgtca acatgcatg cacgcatcgt tacttactgc cctgtgctcc     1560
gcccagtagg caggaatggt gccacaaaat gtttggaggg taataaaatc agccaatggt    1620
gattagcctt cactcgtctt agtcggaaga cctctcctac gcaggcacgg cctgttttt     1680 tctttattag atataaataa aaaagaaacg agattggcaa cagcctttaa cctgccatcc    1740
gattaccgtt taacgcaggt gggattggcc ctaatcatta cttggtagca caacattagc    1800
gaacagtcaa acacaaattc tgccgggaga ctaaacggc gcatctgtca acgaattgaa    1860
ttcaccagct cggcccaaag atgagtggaa gacccgattt aggttactat ggtgctggag    1920
tctaaacagt accttactca tcctttatgc cgttgtgaat gtagagagag ggaaaagaaa    1980
ataaccgacg tcagcccttt tttggcccac cgtttctaca agaaacacc actgccacca    2040
```

-continued

```
aaacagcatt ttattctcca tctttctttg tttctattat tgcttcccaa tctctgacca    2100
tctcggttgt gcaatcacta ggattagtcc ccagtgtaac aatagattgg atgatatctg    2160
gctattataa ttctcaacgg tttcccagta tttcgggtgc agcgaaatcg tatcgtaatg    2220
tcacaatcag cgagaaacaa taacgatttt ctcttccttt tacctttga ttttggcttt     2280
ttttcctcac ccttcagttg tttgccactc aaaatagctc atcgcattgt ctctgtgttg    2340
ttgagctagt cagttattag atggaccgta gaagggagtt gaatatccta atgctgggca    2400
atgtaggtgt tgggaagtcc tcaatcaccc tacagtttgt ccagaatcaa atgccggagc    2460
accatgatga cgatatagaa gacacgtaca gtagagtctg ggagatcgag gggaaggagt    2520
accagataaa cattcttgat actgctgact cctcccaatc gaccatggag actgatctac    2580
aatccgatca cagaagacag cagattctcg caacccaagg aattatactg gccttccgta    2640
tcaattccaa ggactccttt gataatttat caaacattct ccgaaatctt agccgcatac    2700
ggggaactc tttacctcca atattactcc tggggaacat gatggacttg aagatgaaa      2760
gggaagtttc tagaacggaa gccgagtacc tccagtatca gtacaaactt gacgactata    2820
tcgaggctag tgcatctatg aggctaaacg ttgacgacgt gttcactaga atgatagagc    2880
ttatactaga tatcccagat agtaaaccac atagtgccaa cgacagccag gtcggcatac    2940
gccagaactc ttcgatgcaa ggagagtcta acatgatag aaacatagac gatgaagatt     3000

<210> SEQ ID NO 34
<211> LENGTH: 3000
<212> TYPE: DNA
<213> ORGANISM: Pichia pastoris

<400> SEQUENCE: 34
tttctgctgt ggtaccttct ttcttaccca atcatgttcg tctccacatc ggattattgt      60
ttttccgtta gaccagattt ccccttcgct gctgctccaa ttccaaagtc tcaaacaatg    120
ctttgaaatt gcctgctcca aacccgttat ggttttctcg ttggatcact tccaagaata    180
aggtcggccg gtcctgcatc ggtttactga ataactgcaa gaggtaaccg ttctcgtcaa    240
aatcaaccag aattccagcc ttttccaact catcgaggga ttctttaatt tcgtagttcc    300
gttttgtttc taggagacgc tgccgcaatc tagagtagta tttgggtgga acgttttataa    360
actccacacc tctaaatttc atgttcttca ctgtggagac gatattgggg gtcagcagcg    420
ctatatgctg cacaccgggg ccctcataaa agtccaagaa ctcctctatc tgggacttct    480
taagtcccctt tgcaggctcg tttataggca tttttaccag ttcgttgctt gaggccatca    540
ctgttgacct caatgctgaa tattgggtgc atatcacatt ctcatctacc gaccaaaatt    600
ggtgaaatcc aaacgctttg gcataaaact cgcaggattg aaacatctca ttccagtctt    660
ggttttggac acaatgatct atgcaagcaa atgaaacttt tggtagcact ttttcgttca    720
attctgtcac cgtctgcatg tagtcatggc caaaggcgtc ctcatatgat atgtaccctg    780
gcatgaacac acctttatac tgacttcgat tgatcaaagt atgcacaacg tcacctaatg    840
ctccaacttt ggctattacc aaagtagacc cttcttcttc tagagctgta ggtttcaaga    900
ttggccgtgc tccatttgct actgccaact caaatacatg tgaaacattc tccacttgaa    960
aagcaacgtc cttcaccccca tccccgtgtt ttgcaacgtg attttgaatt tccttgatca   1020
tcagatcctc gttttttgttg tcactaaatg atcttaatgt actaacgaac tggaacgtca   1080
cagatccgtt agatacaaca tgatgacaga tattcttgga gccagtttcc aatcccttgt    1140
aggctatggg gtaaaaccct agagagttta tgaagaaccg agagcttagt tttgcattag   1200
```

| | |
|---|---:|
| acacatagaa ggtcacatgg tcatatgcta caaatccgtc gtttgcaagt ttaggcatca | 1260 |
| gcgaggagtc gatagataag ccttcgagtt ggttggtttt ggccaacgag gaggacaaat | 1320 |
| ccaaactatc ttttacaagg acatgctctg acaagggatt tactggttct accatgaggg | 1380 |
| aaagaagatt cgaaggagca aacgggtaag ttcaaaggcc acaaagttgg aggagtagag | 1440 |
| atcaggaaag caggaactac atcgcggttc tgaggaagga gatgtccgat gttagatgta | 1500 |
| aaggggtttg cttatctccc gtaggcattc aatgcattaa aatgaagtct ctcccaaaaa | 1560 |
| cagcagtaac tccttccttc cccggtttcg taactgccta tttatgtgaa caacatccta | 1620 |
| tattagtaat tatctctgca atagcccact gctcccccag atttctaatc aaaccccga | 1680 |
| aaaagtcgct cccccactaa tctcatagat tttccccac tgttgtcaaa accctgtaac | 1740 |
| ctcccgatta cgcaatatct atacgatatt cacttattgt tgcctagcta taaataagga | 1800 |
| cggctcaccc aaatttcaac tcttcatcaa aatgccagga gaaagagttt tacttaccgg | 1860 |
| agcatccggc ttcattgccc agcacattac agacgttctg ctctctaagg gttacagagt | 1920 |
| cttgggaacc actagaagac aggaacaggc cgaccaattg actcaacaat tcacggcaga | 1980 |
| gtacccgaag atcgctgagg acaagtccct gttgcaattc catttggtcc ctgacatcgg | 2040 |
| taccgacaat gctttcgatg aagtcttgaa gcagaacccg gatatagatt tcgtcctgca | 2100 |
| tactgcttcc cccttctact ttggtgacga cagacctttg aaggaggttt atttacaccc | 2160 |
| tgctgttggt ggaaccgaga acattttgaa cgctatccaa aagtacgctt cagacaatat | 2220 |
| caagaaggta gtggtcacat cttcgtttgc tagtgttgtc aacatggaca agttcaagga | 2280 |
| taaacgtttc attcacaatg aagacacttg gaatcctctt acttgggagc aggccgaagt | 2340 |
| agaaggagag acttctgctt atagagcctc taagaaatac gcagaattgg ctgcttggga | 2400 |
| tttcgtcaag aaggagtcgc caaagttcag tttgactacc atcctccccc catttgtctt | 2460 |
| tggtcctcag aagttttctt ctagcgcagc caaaggcaca ttgaacactt cagccgaaat | 2520 |
| tgttaacaag ttcctttcca ctgagtatcc atcagatgac aagttttttg atgctccaac | 2580 |
| ccacttgtct gttgatgtta gagatgtggc tctttaccat gttttgccct tagagattaa | 2640 |
| tgctctggct aacaagaggt tattcactgt ccagagcaag ttctctggtc aaagaatatt | 2700 |
| gaatattctg aacgagaact tcccagaact caagggcaag attgctgttg acaacctga | 2760 |
| aaagacagca cagaatgaag ctgccaatgg tccagaatac aacaatagtt tgaccgtagc | 2820 |
| tttgggagga gtcgagttcc gatcattgga aaccactatt attgattcgg tgaaacaaat | 2880 |
| ccttgagtct gcaaaataat aagatttgat taaatacatt aagtttatac aaatcgaata | 2940 |
| caattactcc ttctcctcct tcttttggt cctctttaca cagtacgaac aatctcagga | 3000 |

<210> SEQ ID NO 35
<211> LENGTH: 3000
<212> TYPE: DNA
<213> ORGANISM: Pichia pastoris

<400> SEQUENCE: 35

| | |
|---|---:|
| cagatgaaga actagattat gctgatgaag atgttccact agttgatgtt gcagaataag | 60 |
| tacttcaagc caataaacct gcgtgcttga ttggtgggag aggacttgtg cacctactg | 120 |
| agaagggaga agctcaactg tatttcttct tcatttactt taagggtgaa gaccattttt | 180 |
| gtcctttaat gtttctttgt tttattgttt attgtttctt atatacccaa actaaatata | 240 |
| ctaatgttca gtgatccatg aaggagcccc tcccccagcg agtccaagac tggccccgaa | 300 |
| atttctataa tctgctacag ccaggttggg atgtgaagtt catcagtgac tgcacctgga | 360 |

```
gccaaactga tgccacgttg ggccaagaca gtgaactagg ggtccaactt atcaaaatac    420
ctgaatccgt cagagcgcga aagcctaatg ccagcttcaa ctttcagagt tgaaccctcc    480
cctcccccaa tacgtataac gatcaaccca caattgcaca ccacagacgt tgtaagatc    540 tgatgttgtg gccatatgtt gtatctcaca tcaattcatt gccacaggtt tcgttacccg    600
atcacgccaa taaagattcc aacgtaatag atgactcctc ccatacagaa ccaattattc    660
agataagccc aaataagtat aatctaccaa ctgttgcaat taccaagaga tctttgtact    720
tgttcaacta tcgtacctac tcaccaattg ctgcgcatgt acgaaaactt tcttcattgg    780
aggaatatgg tgagaataag aatgtgaaaa ttacctccga tgggttcatg tttgttgttg    840
agacgtccaa gaattaccta atggtgttca ccattcataa ccttaagaat ggagaggtaa    900
ccacactaaa tgaagtacag actgtttttt catccaatgg cacgttattg caacaggggt    960
tccccctaat cgaaacggaa tcatcctcaa tcacttcctt catttcgaca atgttctcca   1020
gagctgacct tgagtatcct aatttttgatt ttggtttacg attcaagttg gtgctaaaag   1080
tgcaacgtcc attggttgcc tttcattccc actcttctga tgttcttatg cttctatcca   1140
cagatcctct ctccttttcaa gtgatcaacc ttttttcgaa gaataggacg gatggaaagc   1200
atattgaggt tctgttgttg gagcagttgg actggtatcg aatcgatcag tccgaagtta   1260
agtcgtggat ttactctaag cgatggagtt gttttttctg gcttacagag aagggaaata   1320
tttggaaggt acgtactgag attggaccgt caaatggaac caccaaacta gatggggtat   1380
gtttgtacaa tcaggaacta gaagatcaaa atgatcctaa aattgttggt ctttacttga   1440
atgatcttca agattgcctt taccttgtgg atgagaatga aaacatacga atctaccatc   1500
gaacaaatga aaattacat ctatggagaa ttgtggaaaa accattatct ttggaaaggt   1560
taattgacat ccagtttttcc ccttctgggc agtcttttat caccagattt tttaacggtt   1620
ggaatatgta cagcagcatg ggaaatcttt gttttcatc cattgatcat agtgattctt   1680
ccatcgctga agttgacaac tggttgcaat ttgtgagcga tataaggttt acccctcaa   1740 acgatttaat aatatccaaa ggaagcttgt ttttgttgt tgggcttatc aatttgaact   1800
cgtcattaaa ccaatgttca ataactgca aagaccaat actttacacc agcgaggaac   1860
tatttctatt caaaggttgg gataagaatt tgactgatta ctttaagcag gatcccgcct   1920
tgtcgagaga tgctaccttg tggttgccaa tcaacatacc tacaaagttt atcttaaaga   1980
atctgcacat tactagtata agctcggatg agagtggaac actaatttgt gtagttggaa   2040
ataagtcagc acttgtttat catgttgtta cagacaaatg gaagctgttc gatttgaatt   2100
cggaagtcac acttcaccaa gccgaatcaa ctagtaatga gcaaaacaat aatattatag   2160
ctaccggttg gtgaaaaat cacctattca tggctttgag aaacattttt gatgataacg   2220
gcaaacttat ttcagcgtca aaagttttgg tattttcaac cttacgtttc gattccaatg   2280
atgaaaagga aacttatttt ggtgccgagg agattatttg gagttttgac tttgaggaaa   2340
cttcagttga cgagttcttg ctctatttca attgtgatgt cttgaggtcc caactaattg   2400
ttgtcagttc tgaattcaat gtttacactt ggtcaatgag tatggaatct cacgaagaaa   2460
aaaaaacaaa aggaaggctg atcttgcaaa gaggaaatgt ttacagattg aagaatctct   2520
ttgcagaaaa tgataagcta aattccaaaa gattaaagac tttgaaatat gttagcttaa   2580
ttgacgaaca caacattgtt atgttatttg aagggatctt ttattgcgtt caaagatcct   2640
tgaataaaga tcctgaaaat cctagttttag tcaaagtcgg ttacaccaaa gaagtgatta   2700
gcactggaat agagtttatt caagttgttt ccgcagatgt cgtgattgca ttcaatggtt   2760
```

```
gcaaatgttt atattttgat ctgtgtcaag agaagaatat atcagaggtg tcacccatat    2820
tcatagatac cggatcagaa tctgctctgg catcccacag aaacctttct aaacaccaac    2880
aagatatact gaataacaaa gctttgacaa taaggaagac tgaagggact caggcttatc    2940
ccatattgat tatgagtgaa aaaagcttgc ttttggtct tgatatcgag atctcaacaa    3000

<210> SEQ ID NO 36
<211> LENGTH: 125
<212> TYPE: DNA
<213> ORGANISM: Pichia pastoris

<400> SEQUENCE: 36
gacctccgcg acggggaatt gaaccccggt ctaccgcgcg acaagcggtg gttctaccac      60
taaactatca cggatttcga tgctgctttc ccacttcctt actttacatt ctctaggcgt     120
ttagc                                                                125

<210> SEQ ID NO 37
<211> LENGTH: 125
<212> TYPE: DNA
<213> ORGANISM: Pichia pastoris

<400> SEQUENCE: 37
gacctccgcg acggggaatt ccaccccggt ctaccgcgcg acaagcggtg gttctaccac      60
taaactatca cggatttcga tgctgctttc ccacttcctt actttacatt ctctaggcgt     120
ttagc                                                                125

<210> SEQ ID NO 38
<211> LENGTH: 125
<212> TYPE: DNA
<213> ORGANISM: Pichia pastoris

<400> SEQUENCE: 38
ttgagaaata cgggaatcga acccatgtca cctgcttgga aggcaagtat gataaccact      60
acactaattt cccttggatg taatcatgaa ctaaggttat ccccatgtag ggttattttt     120
caaaa                                                                125

<210> SEQ ID NO 39
<211> LENGTH: 125
<212> TYPE: DNA
<213> ORGANISM: Pichia pastoris

<400> SEQUENCE: 39
ttgagaaata cgggaatccc acccatgtca cctgcttgga aggcaagtat gataaccact      60
acactaattt cccttggatg taatcatgaa ctaaggttat ccccatgtag ggttattttt     120
caaaa                                                                125

<210> SEQ ID NO 40
<211> LENGTH: 125
<212> TYPE: DNA
<213> ORGANISM: Pichia pastoris

<400> SEQUENCE: 40
aacggggcga gctgggaatt gaacccaggg cctctcgcac ccaaagcgag aatcatacca      60
ctagaccaca cgcccgtgcg atggaaagaa aagtctcaag attgttatgt tgaaaagttc     120
tttat                                                                125
```

```
<210> SEQ ID NO 41
<211> LENGTH: 125
<212> TYPE: DNA
<213> ORGANISM: Pichia pastoris

<400> SEQUENCE: 41
aacggggcga gctgggaatt ccacccaggg cctctcgcac ccaaagcgag aatcatacca      60
ctagaccaca cgcccgtgcg atggaaagaa aagtctcaag attgttatgt tgaaaagttc     120
tttat                                                                 125

<210> SEQ ID NO 42
<211> LENGTH: 125
<212> TYPE: DNA
<213> ORGANISM: Pichia pastoris

<400> SEQUENCE: 42
attgaactcg ggcgagctg ggaatcgaac ccaggacctc tcacacccga agcgagaatc      60
ctaccgctag accacacgcc ctgaggcaaa tcagtcttgg taaatgatag agtggtggta     120
tagta                                                                 125

<210> SEQ ID NO 43
<211> LENGTH: 125
<212> TYPE: DNA
<213> ORGANISM: Pichia pastoris

<400> SEQUENCE: 43
attgaactcg ggcgagctg ggaatcccac ccaggacctc tcacacccga agcgagaatc      60
ctaccgctag accacacgcc ctgaggcaaa tcagtcttgg taaatgatag agtggtggta     120
tagta                                                                 125

<210> SEQ ID NO 44
<211> LENGTH: 125
<212> TYPE: DNA
<213> ORGANISM: Pichia pastoris

<400> SEQUENCE: 44
agaatgccct ctgccagaat tgaactagcg acctttgcat tacaagtgca acgctctacc      60
actaagctaa gggggctcaa cttgttggag tgattgaaca ttagatatct aaggacaact     120
agtat                                                                 125

<210> SEQ ID NO 45
<211> LENGTH: 125
<212> TYPE: DNA
<213> ORGANISM: Pichia pastoris

<400> SEQUENCE: 45
agaatgccct ctgccagaat tccactagcg acctttgcat tacaagtgca acgctctacc      60
actaagctaa gggggctcaa cttgttggag tgattgaaca ttagatatct aaggacaact     120
agtat                                                                 125

<210> SEQ ID NO 46
<211> LENGTH: 125
<212> TYPE: DNA
<213> ORGANISM: Pichia pastoris
```

<400> SEQUENCE: 46
actccgcgac ggggaattga accccggtct accgcgcgac aagcggtggt tctaccacta    60
aactatcacg gatggttata aaggcactcc gctttggaga ttattctata aagtcattaa   120
cagat                                                              125

<210> SEQ ID NO 47
<211> LENGTH: 125
<212> TYPE: DNA
<213> ORGANISM: Pichia pastoris

<400> SEQUENCE: 47
actccgcgac ggggaattcc accccggtct accgcgcgac aagcggtggt tctaccacta    60
aactatcacg gatggttata aaggcactcc gctttggaga ttattctata aagtcattaa   120
cagat                                                              125

<210> SEQ ID NO 48
<211> LENGTH: 125
<212> TYPE: DNA
<213> ORGANISM: Pichia pastoris

<400> SEQUENCE: 48
taatgacaac tgtggggttc gaacccacgc ctccggagag accagaacct taatctggcg    60
ccttagacca actcggccaa attgtctcta cgtaagtata cacgaaagat gtcatatata   120
aggga                                                              125

<210> SEQ ID NO 49
<211> LENGTH: 125
<212> TYPE: DNA
<213> ORGANISM: Pichia pastoris

<400> SEQUENCE: 49
taatgacaac tgtggggttc ccacccacgc ctccggagag accagaacct taatctggcg    60
ccttagacca actcggccaa attgtctcta cgtaagtata cacgaaagat gtcatatata   120
aggga                                                              125

<210> SEQ ID NO 50
<211> LENGTH: 125
<212> TYPE: DNA
<213> ORGANISM: Pichia pastoris

<400> SEQUENCE: 50
aagtggtccc tagcaggatc gaactgctga tccccgcgtt attagcacga tgccttgacc    60
aactgggcca aggaccatt gattagttga gagtagctaa tattatacta tatgcttatt   120
atgaa                                                              125

<210> SEQ ID NO 51
<211> LENGTH: 125
<212> TYPE: DNA
<213> ORGANISM: Pichia pastoris

<400> SEQUENCE: 51
aagtggtccc tagcaggatc ccactgctga tccccgcgtt attagcacga tgccttgacc    60
aactgggcca aggaccatt gattagttga gagtagctaa tattatacta tatgcttatt   120
atgaa                                                              125

<210> SEQ ID NO 52
<211> LENGTH: 125
<212> TYPE: DNA
<213> ORGANISM: Pichia pastoris

<400> SEQUENCE: 52

```
acctccgatg ccgggagtcg aacccgggtc tgcccggtga agcggaccg tgctagccgt    60 tacactacat cggatgtaga taaccaaaaa ttaaaccatt gagcttttgt tatacaattt   120
tactg                                                              125
```

<210> SEQ ID NO 53
<211> LENGTH: 125
<212> TYPE: DNA
<213> ORGANISM: Pichia pastoris

<400> SEQUENCE: 53

```
acctccgatg ccgggagtcc cacccgggtc tgcccggtga agcggaccg tgctagccgt    60 tacactacat cggatgtaga taaccaaaaa ttaaaccatt gagcttttgt tatacaattt   120
tactg                                                              125
```

<210> SEQ ID NO 54
<211> LENGTH: 125
<212> TYPE: DNA
<213> ORGANISM: Pichia pastoris

<400> SEQUENCE: 54

```
acagggcga gctgggaatt gaacccaggg cctctcgcac ccaaagcgag aatcatacca    60
ctagaccaca cgccctgata ttgaaagaag agtgtctgga aattatatga cattaaagac   120
tcagg                                                              125
```

<210> SEQ ID NO 55
<211> LENGTH: 125
<212> TYPE: DNA
<213> ORGANISM: Pichia pastoris

<400> SEQUENCE: 55

```
acagggcga gctgggaatt ccacccaggg cctctcgcac ccaaagcgag aatcatacca    60
ctagaccaca cgccctgata ttgaaagaag agtgtctgga aattatatga cattaaagac   120
tcagg                                                              125
```

<210> SEQ ID NO 56
<211> LENGTH: 125
<212> TYPE: DNA
<213> ORGANISM: Pichia pastoris

<400> SEQUENCE: 56

```
gtatgcgaat tctgtggatc gaacacagga ccttcagatt attgagaccg aagttttctt    60
cagtctgacg ctctcccaac tgagctaaat ccgcaattac aagtacaaaa cttctcttgt   120
ctctt                                                              125
```

<210> SEQ ID NO 57
<211> LENGTH: 125
<212> TYPE: DNA
<213> ORGANISM: Pichia pastoris

```
<400> SEQUENCE: 57
gtatgcgaat tctgtggatc ccacacagga ccttcagatt attgagaccg aagttttctt      60
cagtctgacg ctctcccaac tgagctaaat ccgcaattac aagtacaaaa cttctcttgt     120
ctctt                                                                 125

<210> SEQ ID NO 58
<211> LENGTH: 125
<212> TYPE: DNA
<213> ORGANISM: Pichia pastoris

<400> SEQUENCE: 58
aagcccaacg cggggattga acccgcaacc ttgtgattaa gagtcacacg ctctaccgat      60
tgagctagcc aggcagttta catgaaattg tgtgatttta gctacataaa gttataaatg     120
gtatt                                                                 125

<210> SEQ ID NO 59
<211> LENGTH: 125
<212> TYPE: DNA
<213> ORGANISM: Pichia pastoris

<400> SEQUENCE: 59
aagcccaacg cggggattcc acccgcaacc ttgtgattaa gagtcacacg ctctaccgat      60
tgagctagcc aggcagttta catgaaattg tgtgatttta gctacataaa gttataaatg     120
gtatt                                                                 125
```

PAN-YEAST AUTONOMOUSLY REPLICATING SEQUENCE

This application claims the benefit of U.S. provisional patent application No. 61/769,085, filed Feb. 25, 2013, 61/784,975, filed Mar. 14, 2013, and 61/868,749, filed Aug. 22, 2013, the entire contents of each of which are incorporated herein by reference.

STATEMENT REGARDING FEDERALLY SPONSORED RESEARCH

This invention was made with government support under Grant Nos. 8 P41 GM103533-17 and GM090561-03, each awarded by the National Institutes of Health (NIH). The government has certain rights in the invention.

TECHNICAL FIELD OF THE INVENTION

The present invention relates to molecules and methods for improving, stabilizing, enhancing, increasing, and optimizing replication of plasmids in multiple yeast species.

BACKGROUND OF THE INVENTION

The initiation of DNA replication at replication origins is essential for the duplication of genomes. In yeast, the autonomously replicating sequence (ARS) property of replication origins is necessary for the stable maintenance of episomal plasmids. However, because the sequence determinants of ARS function differ among yeast species, current ARS modules are limited for use to a subset of yeasts. In addition, lower efficiency replication origins result in the loss of plasmids during culture growth. Origins have not been isolated or optimized in many yeast species, making the use of plasmid-based expression systems difficult.

Due to the diversity of sequences required for origin function in different yeast species, ARSs are usually restricted to function in only a few yeast species. For example, *K. lactis* ARSs rarely work in non-*Kluyveromyces* yeasts and ARSs from other species rarely function in *K. lactis* host cells (Liachko et al. 2010; 2011). On the other hand, *L. kluyveri* is a permissive host species and can utilize most ARSs from *S. cerevisiae* and *K. lactis* (Liachko et al. 2011). The methylotrophic budding yeast *Pichia pastoris* uses at least two different kinds of ARS sequences, neither of which function in *S. cerevisiae* (Liachko et. al., PLoS Genetics, 2014, in press).

There remains a need for an ARS that functions across all yeasts. In addition to facilitating commercial use of yeast expression systems, an ARS that works across a variety of yeast species would be a useful genetic tool to provide shuttle vectors for cross-species studies.

SUMMARY OF THE INVENTION

To address these needs and others, we have identified a 452 bp DNA sequence from the *Kluyveromyces lactis* genome that functions as an origin in many different yeast species. We have introduced 1 to 17 mutations into this sequence to improve its function across multiple yeasts. The resulting synthetic DNA sequence confers stable plasmid replication function in all yeast species tested. This module is useful for plasmid based expression systems in multiple yeast species.

In one embodiment, the present disclosure includes methods for improving, stabilizing, enhancing, increasing, or optimizing replication of plasmids in multiple yeast species, including but not limited to *Saccharomyces cerevisiae, Saccharomyces bayanus, Saccharomyces paradoxus, Lachancea kluyveri, Lachancea waltii, Kluyveromyces lactis, Kluyveromyces wickerhammii, Hansenula polymorpha, Naumovozyma castellii,* and *Pichia pastoris,* comprising transforming one of SEQ ID NO:1-19 into a yeast cell. In one embodiment, the present disclosure includes a yeast cell comprising one or more of SEQ ID NO:1-19, such as SEQ ID NO: 6-9 or 19. In one embodiment, the present disclosure includes a yeast cell other than *Kluyveromyces lactis* comprising one or more of SEQ ID NO:1-19. In one embodiment, the present disclosure comprises SEQ ID NO:6-9 or 19.

In another embodiment, the present disclosure comprises a nucleotide sequence having at least one of the illustrated mutations in SEQ ID NO:1-3, 5-9, 14-15, and 17-19. In another embodiment, the nucleotide sequence has two or more mutations relative to the corresponding wild type sequence. In a further embodiment, the nucleotide sequence has at least one of the mutations identified herein as "beneficial", "very beneficial", or "optimizing".

In another embodiment, the invention provides an efficient origin of replication in *Pichia pastoris,* ARS-C379 or ARS-A2772. The results of deep mutational scanning showed which nucleotides are important to function. The ARS-C379 and ARS-A2772 sequences were optimized by changing the nucleotides within the core functional region to the ones that have the most positive effect on ARS function. The resulting optimized sequence has several mutations relative to wildtype and confers an improved plasmid maintenance function in *P. pastoris* cells.

In one embodiment the present disclosure includes methods for improving, stabilizing, optimizing, increasing, or enhancing replication of plasmids in yeast species, including but not limited to *Pichia pastoris* comprising transforming SEQ ID NO: 9 or 19 into a yeast cell.

In one embodiment, the invention provides autonomous replicating sequences (ARSs) in the form of a recombinant or synthetic nucleic acid molecule selected from the group consisting of SEQ ID NO: 1-19. In one embodiment, the nucleic acid molecule includes at least one mutation relative to the corresponding wild type sequence. In a typical embodiment, the mutation is at one or more nucleotides corresponding to the following positions of SEQ ID NO: 2: 102, 103, 107, 108, 110, 111, 115, 122, 124, 141, 144, 151, 202, 213, 214, 220, 229, or of SEQ ID NO: 5: 8, 16, 17, 18, 21, 23, 24, 25, 27. Optionally, the nucleic acid molecule may include additional adjacent sequence of up to 10-50 bp in length at either or both ends. Such additional adjacent sequence is not required, but can be added without interfering with the function of the ARS. For example, the 99 bp sequences shown in SEQ ID NO: 5, 9, and 19, have been used as fully functional ARSs as 100 bp sequences with the addition of a single wild type nucleotide. Likewise, functional ARS activity has been found with substantial deletions at either end of SEQ ID NO: 11 (e.g., see SEQ ID NO: 4, 10, and 12).

Sequences Referenced:

SEQ ID NO: 1—188-371 (of the full 452 bp) panARS with optional bases indicated at each of 5 mutation sites.

SEQ ID NO: 2—full 452 bp panARS with optional bases indicated at each of 17 mutation sites.

SEQ ID NO: 3—188-316 of 452 panARS with optional bases indicated at each of 5 mutation sites.

SEQ ID NO: 4—256-371 of 452 panARS (same as wild type).

SEQ ID NO: 5—PpARS-C379 with optional bases indicated at each of 9 mutation sites.

SEQ ID NO: 6—188-371 (of the full 452 bp) panARS with each of 5 optimizing mutations.

SEQ ID NO: 7—full 452 bp panARS with each of 17 optimizing mutations.

SEQ ID NO: 8—188-316 of 452 panARS with each of 5 optimizing mutations.

SEQ ID NO: 9—PpARS-C379 with each of 9 optimizing mutations.

SEQ ID NO: 10—188-371 (of the full 452 bp) panARS wild type sequence.

SEQ ID NO: 11—full 452 bp panARS wild type sequence.

SEQ ID NO: 12—188-316 of 452 panARS wild type sequence.

SEQ ID NO: 13—PpARS-C379 wild type sequence.

SEQ ID NO: 14—PpARS-C379 with several optional mutations shown.

SEQ ID NO: 15—PpARS-C379 with 16 very beneficial mutations shown.

SEQ ID NO: 16—PpARS-A2772 wild type sequence.

SEQ ID NO: 17—PpARS-A2772 with several optional mutations shown.

SEQ ID NO: 18—PpARS-A2772 with 37 very beneficial mutations shown.

SEQ ID NO: 19—PpARS-A2772 with each of 60 optimizing mutations.

In one embodiment, the nucleic acid molecule comprises SEQ ID NO: 1, 2, or 3, and the nucleic acid sequence contains at least 2 mutations relative to the corresponding wild type sequence shown in SEQ ID NO: 10, 11, or 12. Optionally, the sequence may contain 3, 4 or 5 or more mutations relative to the wild type sequence. Representative examples of such nucleic acid molecules include SEQ ID NO: 6, SEQ ID NO: 7 and SEQ ID NO: 8. In one embodiment, the nucleic acid molecule is SEQ ID NO: 4, and optionally contains at least one or more mutations.

In another embodiment, the nucleic acid molecule comprises SEQ ID NO: 5, 14 or 15, and the nucleic acid sequence contains at least 2 mutations relative to the corresponding wild type sequence shown in SEQ ID NO: 13. Optionally, the sequence may contain 3, 4, 5, 6, 7, 8, or 9 or more mutations relative to the wild type sequence. Representative examples of such nucleic acid molecules include SEQ ID NO: 9. In another embodiment, the nucleic acid molecule comprises SEQ ID NO: 17 or 18, and the nucleic acid sequence contains at least 2 mutations relative to the corresponding wild type sequence shown in SEQ ID NO: 16. Optionally, the sequence may contain 3, 4, 5, 6, 7, 8, or 9 or more mutations relative to the wild type sequence. Representative examples of such nucleic acid molecules include SEQ ID NO: 19.

In one embodiment, the invention provides a plasmid comprising (or containing) a nucleic acid molecule described above. In another embodiment, the invention provides a host cell comprising a nucleic acid molecule and/or plasmid of the invention. In a typical embodiment, the host cell is a yeast cell. In one aspect of the invention, the yeast cell has been transformed with a nucleic acid molecule and/or plasmid of the invention.

In one embodiment, the yeast cell is a member of the genera consisting of *Saccharomyces, Lachancea, Kluyveromyces*, and *Pichia (Komagataella)*. Representative yeast cells include, but are not limited to, members of the group consisting of *Saccharomyces cerevisiae, Saccharomyces bayanus, Saccharomyces paradoxus, Lachancea kluyveri, Lachancea waltii, Kluyveromyces lactis, Kluyveromyces wickerhammii, Hansenula polymorpha, Pichia pastoris*, and *Naumovozyma castellii*. In one embodiment, the yeast cell is *Pichia pastoris*, and the nucleic acid molecule is SEQ ID NO: 9 or 19.

In one embodiment, the invention provides a method of producing stable plasmid replication in a yeast cell. Also provided is a method of enhancing plasmid replication in a yeast cell. The method comprises transforming a plasmid comprising a nucleic acid molecule of the invention into the yeast cell. The methods comprise transforming a plasmid comprising a nucleic acid molecule of the invention into the yeast cell. The nucleic acid molecule is typically selected from SEQ ID NO: 1-19. In one embodiment, the yeast cell is a member of the genera consisting of *Saccharomyces, Lachancea, Kluyveromyces*, and *Pichia (Komagataella)*. In some embodiments, the yeast cell is selected from the group consisting of *Saccharomyces cerevisiae, Saccharomyces bayanus, Saccharomyces paradoxus, Lachancea kluyveri, Lachancea waltii, Kluyveromyces lactis, Kluyveromyces wickerhammii, Hansenula polymorpha, Pichia pastoris*, and *Naumovozyma castellii*. In one embodiment, the yeast cell is *Pichia pastoris*, and the nucleic acid molecule is SEQ ID NO: 9 or 19. Alternatively, the nucleic acid molecule is one of SEQ ID NO: 14, 15, 17, or 18. In one embodiment, the method of enhancing plasmid replication in a yeast cell is performed in a yeast cell that is not *K. lactis, S. cerevisiae*, or *L. kluyveri*.

The invention additionally provides a method of producing a shuttle vector for use in multiple species of yeast. The method comprises introducing a nucleic acid molecule of the invention into a plasmid. The plasmid is typically selected from pRS400, pRS40H, pRS40N, pRS40B, pBR322, pIL07 and pIL13, pRS406 and its derivatives pIL19 and pIL22. In one embodiment, the insertion sites are the unique BamHI or the unique AatII restriction site in these plasmids.

Also described herein is a method of producing an optimized autonomous replicating sequence (ARS). The method comprises generating a library of mutagenized wild type ARSs; growing yeast containing the mutagenized ARSs on selective media; measuring the growth rate of the mutagenized ARSs relative to wild type ARSs; and identifying those mutagenized ARSs that grow at a faster rate on selective media relative to wild type ARS as optimized ARSs. The above method can further comprise sequencing the mutagenized ARSs to identify the mutations the effect the optimization of the ARS.

BRIEF DESCRIPTION OF THE FIGURES

FIG. 1A: The ARS-less URA3 vector pRS406 and its counterpart bearing the panARS sequence (pIL20) were used to transform ura3 strains of different budding yeast species. Transformations were plated on agar plates lacking uracil. The growth of URA3 colonies indicates ARS activity conferred by the panARS plasmid (right side of each plate) and not by the empty vector (left side of each plate). FIG. 1B: Relative coordinates of recovered functional subfragments of panARS in different species. FIG. 1C: Plasmid loss assays were performed on indicated yeast species transformed with plasmids bearing the wild-type panARS sequence (ARS) or the optimized mutant allele of panARS (OPT). Plasmid loss per generation of growth in non-selective medium is shown (y axis) with error bars representing standard deviations between at least four replicate experiments. Increased plasmid loss is indicative of weaker ARS function and decreased plasmid stability. Bars represent, from left to right, of S. cerevisiae, ARS & OPT, S. paradoxus, ARS & OPT, S. bayanus, ARS & OPT, L. waltii, ARS & OPT, L. kluyveri, ARS & OPT, K. wickerhamii, ARS & OPT, K. lactis, ARS & OPT, and P. pastoris, ARS & OPT, respectively.

FIG. 2A: Phylogenetic relationships and previously published ACS motifs are shown for S. cerevisiae (Broach et al. 1983; Liachko et al. 2013), L. waltii (Di Rienzi et al. 2012), L. kluyveri (Liachko et al. 2011), and K. lactis (Liachko et al. 2010). FIG. 2B: The sequences of the native (ARS; SEQ ID NO: 12) and optimized (OPT; SEQ ID NO: 7) panARS elements are shown. The region highlighted between the lines represents the only significant match to the K. lactis ACS within the minimal functional region of the panARS. The region highlighted with lighter shading represents a strong match to the K. lactis ACS outside of the main functional region. The region highlighted with darker shading represents the best match to the S. cerevisiae/L. waltii/L. kluyveri ACS motifs. Functional ARS sequence determinants in other species are not yet known. The mutations introduced into the optimized version of ARS are indicated by lowercase letters.

FIG. 3A: The P. pastoris strain was transformed with plasmid pRS316 and a derivative of pRS406 bearing PARS1. Plasmid loss rates are shown for these, as well as wt and optimized panARS plasmids for comparison. FIG. 3B: One-tailed two-sample T-tests were performed on data from plasmid loss assays. The resulting P-values are listed as a table.

FIG. 4A: Schematic of ARS-seq and miniARS-seq screens. Fragmented genomic DNA was ligated into non-replicating URA3 vectors and screened for ARS activity followed by deep sequencing of the resultant plasmid inserts (ARS-seq, top). ARS-seq plasmid inserts were amplified and sheared using DNase I. Short fragments of ARSs were ligated into the URA3 vectors and screened for ARS activity followed by deep sequencing of the plasmid inserts (miniARS-seq, bottom). FIG. 4B: The GC-ACS motif identified by the MEME algorithm (SEQ ID NO: 64). FIG. 4C: The distribution of MAST motif scores of the best match to the GC-ACS in every PpARS. FIG. 4D: 2D gel analysis at loci A2772 (putative AT-ARS at chromosome 1: 2,772 kb) and C379 (putative GC-ARS at chromosome 3: 379 kb). The arrows highlight arcs corresponding to replication bubble intermediates.

FIG. 6A: Schematic of the mutARS-seq deep mutational scanning experiment. Auxotrophic ura3 yeast were transformed with a library of mutant ARS variants and competed in selective medium. The abundance of different ARS variants was determined by deep sequencing at intervals during competitive growth. FIG. 6B: Results of mutARS-seq of ARS-C379. The relevant sequence of ARS-C379 (SEQ ID NO: 13) is shown with the best match to the GC-ACS motif (SEQ ID NO: 64) underlined (and a 3' constrained dinucleotide also underlined). The log-transformed enrichment ratio is shown for each nucleotide at each position along the sequence. FIG. 6C: Results of mutARS-seq of ARS-A2772 (SEQ ID NO: 16). Same as in 6B, except that the motif logo (SEQ ID NO: 65) shown was constructed from the enrichment ratio scores post-analysis, whereas the motif shown in 6B was constructed from ARS alignments.

FIG. 10A: Genomic DNA from G1 and S phase cells was sheared and sequenced. Normalized S/G1 DNA copy ratios (in 1 kbp windows) were smoothed and plotted against chromosomal coordinates. Peaks correspond to positions of replication initiation. The profile of chromosome 4 is shown (all chromosomes are shown in Figure S6) with ARS locations indicated by open (AT-ARSs) and shaded (GC-ARSs) circles. Un-smoothed ratio data for one of the replicates is shown are grey. Coordinates of replication timing peaks are indicated by dashed vertical lines. FIG. 10B: The distributions of smoothed S/G1 ratio data. The distribution of all ratios ("Genome") is shown adjacent to the distribution of values at bins containing midpoints of GC-ACSs ("GC") or AT-ARSs ("AT"). Values for ARSs that have no other ARSs within 40 kb in both directions are shown on the right ("isolated"). FIG. 10C: The complete genomic ratio distribution is shown relative to distributions after removal of data within 60 kb ranges centered on AT-ARSs ("AT"), GC-ARSs ("GC"), or all ARSs ("all ARS"). FIG. 10D: For each ARS, the distance to the nearest replication peak was calculated. The ARS-peak distances are shown as distributions separately for GC-ARSs (darkest bars) and AT-ARSs (medium-tone bars). Peak distances from simulated random sets of loci are shown in light grey.

DETAILED DESCRIPTION OF THE INVENTION

The present invention is based on the discovery and identification of a 452 bp *K. lactis* genomic fragment that retains ARS function in at least 10 budding yeast species with diverse ARS sequence requirements. This sequence ("panARS") maps to coordinates 781040-781491 bp on chromosome F of the *K. lactis* genome (strain NRRL Y-1140 (Dujon et al. 2004)).

Figure 1A:
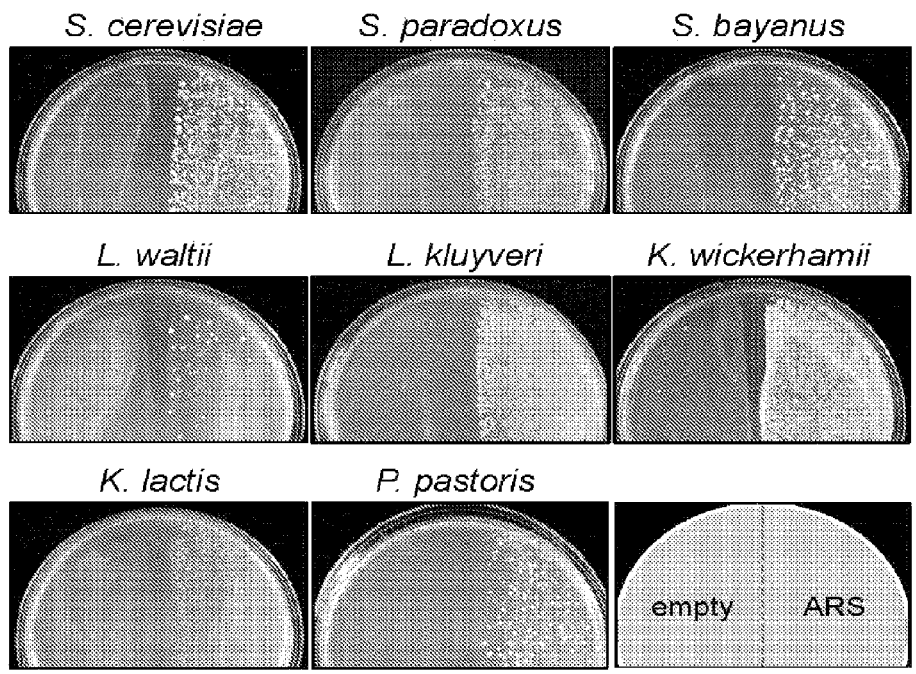
FIGS. 1A-1C. The function of panARS in different budding yeast species.
Figure 1B:
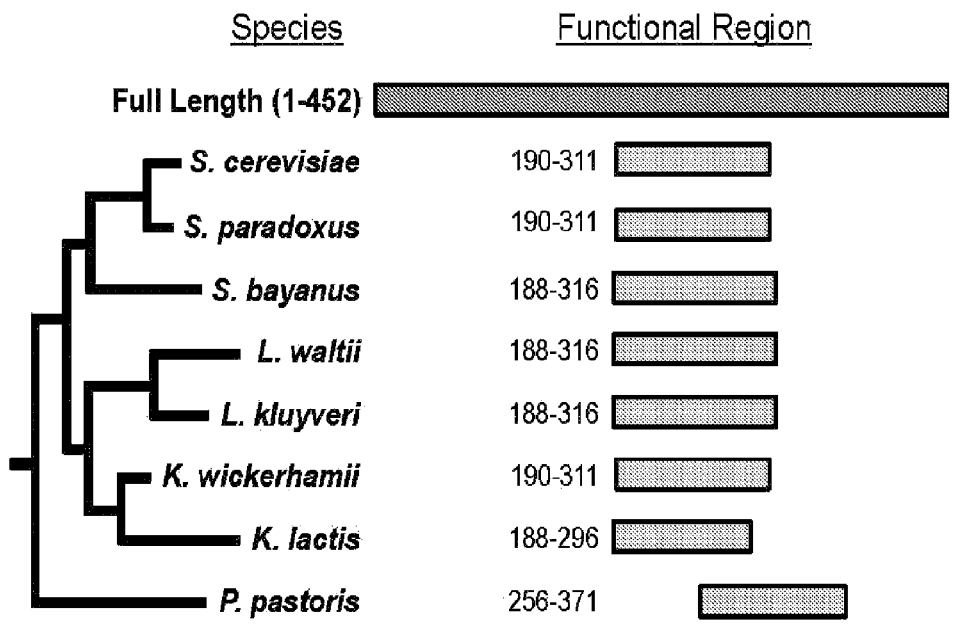

To delineate the region of panARS required for function in each of the different species, we sheared the 452 bp ARS fragment and cloned a library containing ARS sub-fragments. This library was used to transform the different yeast species in order to identify sub-fragments of the ARS that retain function. Short ARS fragments isolated from this screen were also tested for function across multiple species. In this manner we were able to isolate the minimal region of the ARS that confers function across all species to a region near one end of the ARS (e.g., within positions 188-371 relative to the 452 bp fragment; see FIG. 1B). All species listed except *P. pastoris* were able to initiate replication with ARS sub-fragments in a region between relative positions 188-316. For ARS function, *P. pastoris* required ARS DNA fragments within relative coordinates 256-371 (FIG. 1*b*).

In addition, we describe herein a synthetically optimized mutant version of this sequence that performs either equivalently to or better than the wild type sequence. Additionally, this module performs significantly better than other characterized ARS plasmids in *P. pastoris*, with a stability that resembles ARS/CEN plasmids in better-studied models. These results suggest that panARS provides an efficient ARS module in other related yeast species and a superior construct even when cross-species performance is not required.

We further show that *P. pastoris* has two general classes of origins—NT-rich origins resembling those of most other yeasts, and a novel, G/C-rich class, that appear more robust and are associated with promoters. *P. pastoris* is the first known species using two kinds of origins and the first known budding yeast to use a G/C-rich origin motif. Additionally, we describe herein synthetically optimized mutant versions of this sequence that perform better than the wild type sequence.

DEFINITIONS

All scientific and technical terms used in this application have meanings commonly used in the art unless otherwise specified. As used in this application, the following words or phrases have the meanings specified.

The term "nucleic acid" or "polynucleotide" refers to a deoxyribonucleotide or ribonucleotide polymer in either single- or double-stranded form, and unless otherwise limited, encompasses known analogs of natural nucleotides that hybridize to nucleic acids in a manner similar to naturally-occurring nucleotides.

As used herein, a "heterologous molecule" is not identical to the reference molecule, nor is it, in the context of polypeptides and polynucleotides, an adjacent native sequence with respect to the reference molecule. Heterologous molecules are not limited to polypeptides and polynucleotides. Representative examples of heterologous molecules for use in accordance with the invention include, but are not limited to, labels, small molecules, vectors, and "attachment domains".

As used herein, "small molecule" refers to a low molecular weight organic compound having a molecular weight of less than 2000 Daltons, in some embodiments less than 1000 Daltons, and in still other embodiments less than 500 Daltons or less. A small molecule is typically between about 300 and about 700 Daltons. In a typical embodiment, a small molecule for use with the invention binds with high affinity to a protein, nucleic acid molecule, or a polysaccharide and alters the activity or function of the biopolymer to which it binds. Such molecules include, for example, heterocyclic compounds, carboxylic compounds, sterols, amino acids, lipids, and nucleic acids.

As used herein, "vector" means a construct, which is capable of delivering, and preferably expressing, one or more gene(s) or sequence(s) of interest in a host cell. Examples of vectors include, but are not limited to, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells. Optionally, the vector may include a selectable marker. Examples of selectable markers for use with plasmids of the invention include, but are not limited to, KanMX, HygB, NatMX, and Bleomycin.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "a" or "an" means at least one, unless clearly indicated otherwise.

Autonomously Replicating Sequences

Autonomously replicating sequences (ARSs) as described herein may be of any length. Typically, the ARS will be between 50 and 500 nucleotides in length, more typically about 100 to about 450 bp in length. Optionally, the ARS further includes flanking sequence to facilitate incorporation into a delivery construct or carrier. The ARSs listed in the table below are shown in a form that is suitable for incorporation into a plasmid. Those skilled in the art will appreciate that flanking sequence may be provided to facilitate the insertion process, such as restriction sites and/or short regions of homology.

| ARS (upper case is wild type; lower case is optimizing mutation)* | | SEQ ID NO: |
|---|---|---|
| 188-371 (of the full 452 bp) panARS with optional bases indicated at each of 5 mutation sites: | | 1 |
| AC TTTAATAATT A(G,t)TTTAATAT TT(G,t)(T,g)TTCTA(T,a) | 220 | |
| ATAATGAC(A,t)T TTAATTAAAA AAGATAAAAT ATAAAAACAT | 260 | |
| CATAATAACT CACCAGAGGT TAAGAACAAA AAAACAAATT AGATATCTGC | 310 | |
| TAATCCAATA TAGTTAAATC AATCTTTCCT TGGTATAATG GGTATATTAC | 360 | |
| ATATATTTCA A | 371 | |

-continued

| ARS (upper case is wild type;<br>lower case is optimizing mutation)* | | SEQ<br>ID NO: |
|---|---|---|
| Full 452 bp panARS with optional bases indicated<br>at each of 17 mutation sites:<br>TCAACATCTT TGGATAATAT CAGAATGAGA AAGAACAGAT ACGCAGTACG<br>TTTTTTGGTG AGCTCTTTGC ACTTCTTTAG TTCTTTCCAT CAATATCAGT<br>T(G,t)(C,t)TTA(T,a)(G,a)C(A,t) (C,t)TTA(T,g)GACTA<br>A(T,a)A(T,g)TGATGT TTAACTTCAA (T,a)AT(C,g)TTTAAA<br>(C,a)TTTTGTTCT TCCCGACGTT CATTAAGAAT ACTAATACAC<br>TTTAATAATT A(G,t)TTTAATAT TT(G,t)(T,g)TTCTA(T,a)<br>ATAATGAC(A,t)T TTAATTAAAA AAGATAAAAT ATAAAAACAT<br>CATAATAACT CACCAGAGGT TAAGAACAAA AAAACAAATT AGATATCTGC<br>TAATCCAATA TAGTTAAATC AATCTTTCCT TGGTATAATG GGTATATTAC<br>ATATATTTCA AGGACCGACA CTCCTACCAA ATATCTAAAA TTTACCATAT<br>TAACATAACA TGTATATAAA CGTCAAATCA TAATCAGCAC TA | 50<br>100<br>120<br>150<br>190<br>220<br>260<br>310<br>360<br>410<br>452 | 2 |
| 188-316 of 452 panARS with optional bases indicated<br>at each of 5 mutation sites:<br>AC TTTAATAATT A(G,t)TTTAATAT TT(G,t)(T,g)TTCTA(T,a)<br>ATAATGAC(A,t)T TTAATTAAAA AAGATAAAAT ATAAAAACAT<br>CATAATAACT CACCAGAGGT TAAGAACAAA AAAACAAATT AGATATCTGC<br>TAATCC | 220<br>260<br>310<br>316 | 3 |
| 256-371 of 452 panARS:<br>AACAT<br>CATAATAACT CACCAGAGGT TAAGAACAAA AAAACAAATT AGATATCTGC<br>TAATCCAATA TAGTTAAATC AATCTTTCCT TGGTATAATG GGTATATTAC<br>ATATATTTCA A | 260<br>310<br>360<br>371 | 4 |
| PpARS with optional bases indicated at each of 9<br>mutation sites (1st position optional):<br>(G)TTGGGA(A,t)TC GAACC(C,t)(A,t)(A,c)GA<br>(C,t)C(T,g)(C,g)(T,a)C(C,g)CTT GCAAGGGGAG CGCGCTACCA<br>ACTACGCCAC ACGCCCGAAT AATACAAACT AGGATAATGG AGTAATTATA | 20<br>50<br>100 | 5 |
| 188-371 (of the full 452 bp) panARS with each of<br>the 5 optimizing mutations:<br>AC<br>TTTAATAATT AtTTTAATAT TTtgTTCTAa ATAATGACtT TTAATTAAAA<br>AAGATAAAAT ATAAAAACAT CATAATAACT CACCAGAGGT TAAGAACAAA<br>AAAACAAATT AGATATCTGC TAATCCAATA TAGTTAAATC AATCTTTCCT<br>TGGTATAATG GGTATATTAC ATATATTTCA A | 190<br>240<br>290<br>340<br>371 | 6 |
| Full 452 bp panARS with optional bases indicated with<br>each of the 17 optimizing mutations:<br>TCAACATCTT TGGATAATAT CAGAATGAGA AAGAACAGAT ACGCAGTACG<br>TTTTTTGGTG AGCTCTTTGC ACTTCTTTAG TTCTTTCCAT CAATATCAGT<br>TttTTAaaCt tTTAgGACTA AaAgTGATGT TTAACTTCAA aATgTTTAAA<br>aTTTTGTTCT TCCCGACGTT CATTAAGAAT ACTAATACAC TTTAATAATT<br>AtTTTAATAT TTtgTTCTAa ATAATGACtT TTAATTAAAA AAGATAAAAT<br>ATAAAAACAT CATAATAACT CACCAGAGGT TAAGAACAAA AAAACAAATT<br>AGATATCTGC TAATCCAATA TAGTTAAATC AATCTTTCCT TGGTATAATG<br>GGTATATTAC ATATATTTCA AGGACCGACA CTCCTACCAA ATATCTAAAA<br>TTTACCATAT TAACATAACA TGTATATAAA CGTCAAATCA TAATCAGCAC<br>TA | 50<br>100<br>150<br>200<br>250<br>300<br>350<br>400<br>450<br>452 | 7 |
| 188-316 of 452 panARS with each of the 5<br>optimizing mutations:<br>AC<br>TTTAATAATT AtTTTAATAT TTtgTTCTAa ATAATGACtT TTAATTAAAA<br>AAGATAAAAT ATAAAAACAT CATAATAACT CACCAGAGGT TAAGAACAAA<br>AAAACAAATT AGATAT | 190<br>240<br>290<br>316 | 8 |
| PpARS-C379 with each of the 9 optimizing mutations<br>(1st position optional):<br>(G)TTGGGAtTC GAACCttcGA tCggaCgCTT GCAAGGGGAG CGCGCTACCA<br>ACTACGCCAC ACGCCCGAAT AATACAAACT AGGATAATGG AGTAATTATA | 50<br>100 | 9 |
| 188-371 (of the full 452 bp) panARS wild type sequence:<br>AC TTTAATAATT<br>AGTTTAATAT TTGTTTCTAT ATAATGACAT TTAATTAAAA AAGATAAAAT<br>ATAAAAACAT CATAATAACT CACCAGAGGT TAAGAACAAA AAAACAAATT<br>AGATATCTGC TAATCCAATA TAGTTAAATC AATCTTTCCT TGGTATAATG<br>GGTATATTAC ATATATTTCA A | 200<br>250<br>300<br>350<br>371 | 10 |

-continued

| ARS (upper case is wild type; lower case is optimizing mutation)* | SEQ ID NO: |
|---|---|
| Full 452 bp panARS wild type sequence:<br>TCAACATCTT TGGATAATAT CAGAATGAGA AAGAACAGAT ACGCAGTACG 50<br>TTTTTTGGTG AGCTCTTTGC ACTTCTTTAG TTCTTTCCAT CAATATCAGT 100<br>TGCTTATGCA CTTATGACTA ATATTGATGT TTAACTTCAA TATCTTTAAA 150<br>CTTTTGTTCT TCCCGACGTT CATTAAGAAT ACTAATACAC TTTAATAATT 200<br>AGTTTAATAT TTGTTTCTAT ATAATGACAT TTAATTAAAA AAGATAAAAT 250<br>ATAAAAACAT CATAATAACT CACCAGAGGT TAAGAACAAA AAAACAAATT 300<br>AGATATCTGC TAATCCAATA TAGTTAAATC AATCTTTCCT TGGTATAATG 350<br>GGTATATTAC ATATATTTCA AGGACCGACA CTCCTACCAA ATATCTAAAA 400<br>TTTACCATAT TAACATAACA TGTATATAAA CGTCAAATCA TAATCAGCAC 450<br>TA 452 | 11 |
| 188-316 of 452 panARS wild type sequence:<br>AC TTTAATAATT 200<br>AGTTTAATAT TTGTTTCTAT ATAATGACAT TTAATTAAAA AAGATAAAAT 250<br>ATAAAAACAT CATAATAACT CACCAGAGGT TAAGAACAAA AAAACAAATT 300<br>AGATATCTGC TAATCC 316 | 12 |
| PpARS-C379 wild type sequence (1ˢᵗ position optional):<br>(G)TTGGGAATC GAACCCAAGA CCTCTCCCTT GCAAGGGGAG CGCGCTACCA 50<br>ACTACGCCAC ACGCCCGAAT AATACAAACT AGGATAATGG AGTAATTATA 100 | 13 |
| PpARS-C379 optimization:<br>TTGGGAATC GAACCCA(A,c)GA<br>(C,t)C(T,g)(C,r)(T,a)C(C,g)(C,A)T(T, c)<br>GCA(A,y)(G,a)(G,t)(G,y)G(A,y)G CGCG(C,a)TACCA<br>ACTACGCCAC AC(G,t)CCC(G,y)(A,c)(A,y)(T,c)<br>(A,b)(A,c)TAC(A,y)A(A,g)(C,t)(T,a)<br>(A,b)(G,h)(G,w)(A,k)(T,r)(A,k)(A,k)(T,r)(G,w)(G,h)<br>(A,k)(G,h)(T,a)(A,y)(A,t)T(T,a)(A,t)(T,a)(A,t) | 14 |
| PpARS-C379 very beneficial mutations:<br>TTGGGAATC GAACCCAAGA CCTCTCCCTT GCAAGG(G,t)G(A,t)G<br>CGCGCTACCA ACTACGCCAC ACGCCCGAAT A(A,c)TACAAACT<br>(A,g)(G,a)(G,a)A(T,r)(A,g)(A,g)(T,g)(G,a)<br>(G,a)(A,g)(G,w)(T,a)A(A,t)TTATA | 15 |
| PpARS-A2772 wildtype:<br>AGATATCGT GCGAATAAAC ATGAATGTTT CATATTTATC AATTACGCTC 49<br>ACTATTAAAT TGTGAGAATC ATATTATAAA TCATGCTATA TATTTATTCT 99 | 16 |
| PpARS-A2772 optimization:<br>(A,t)(G,t)ATAT(C,w)(G,t)T (G,w)CGAA(T,a)AAA(C,w)<br>(A,t)T(G,t)(A,t)(A,s)T(G,y)T(T,a)T<br>C(A,b)T(A,g)(T,s)(T,g)(T,a)(A,b)(T,a)(C,a)<br>(A,k)(A,t)(T,r)(T,g)(A,k)(C,g)(G,c)C(T,g)(C,a)<br>(A,g)(C,r)(T,v)(A,b)(T,v)(T,g)(A,s)(A,s)(A,b)<br>(T,c) T(G,y)T(G,w)(A, c)(G, w)A(A,t)(T,a)(C,w)<br>(A,t)(T,a)ATTATAAA T(C,w)(A,b)(T,a)(G,a)CTATA<br>TATT(T,a)ATTC(T,g) | 17 |
| PpARS-A2772 very beneficial mutations:<br>(A,t)(G,t)ATAT(C,w)(G,t)T GCGAA(T,a)AAA(C,w)<br>AT(G,t)(A,t)AT(G,t)TTT C(A,k)TA(T,s)(T,r)<br>T(A,y)(T,a)(C,a) AATT(A,k)C(G,c)C(T,g)(C,a)<br>(A,g)(C,r)(T,r)(A,y)(T,r)T(A,s)(A,s)(A,c)T<br>T(G,y)T(G,w)(A,c)(G,a)AAT(C,w) (A,t)(T,a)<br>ATTATAAAT(C,w)(A,k)TGCTATA TATT(T,a)ATTCT | 18 |
| PpARS-A2772 fully optimized sequence:<br>tttTAaatT aCGAAaAAAa tgttgatTaT CgTgggacaa ttagtgcCga 49<br>gggtgggccc ctcacaAtaa taATTATAAA TataaCTATA TATTaATTCG 99 | 19 |

*Each nucleic acid recited in these sequences may optionally be substituted with a non-natural derivative of the indicated nucleic acid. Where parentheses are provided, the upper case letter indicates an option that would correspond to wild type sequence, while the lower case letter indicates an optimizing or non-detrimental mutation. An individual sequence may be prepared with some or all, or any combination, of the indicated optional mutations.

It is contemplated that, in some embodiments, where specifically indicated, the nucleic acid sequences of the present invention can comprise variants of SEQ ID NO: 1-19. It is contemplated that such variants have less than 100% sequence identity or similarity with the reference SEQ ID NO. In one embodiment, the variant will have a nucleotide sequence from about 75% to less than 100% nucleotide sequence identity or similarity with the nucleotide sequence of the reference SEQ ID NO., more preferably from about 80% to less than 100%, more preferably from about 85% to less than 100%, more preferably from about 90% to less than 100% (e.g., 91%, 92%, 93%, 94%, 95%, 96%, 97%, 98%, 99%) and most preferably from about 95% to less than 100%, e.g., over the length of the variant molecule. Some variants will share 100% identity with contiguous adjacent nucleotides of the reference sequence, but will have a portion of the reference sequence omitted at either or both ends.

The term percent "identity," in the context of two or more nucleic acid sequences, refer to two or more sequences or subsequences that have a specified percentage of nucleotides residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

Polynucleotides of the invention comprise at least 50 consecutive nucleotides, typically at least about 100 consecutive nucleotides of a nucleic acid sequence shown in SEQ ID NO: 1-19. Polynucleotides that are fully complementary to any such sequences are also encompassed by the present invention. Polynucleotides may be single-stranded (coding or antisense) or double-stranded, and may be DNA or RNA molecules. Additional coding or non-coding sequences may, but need not, be present within a polynucleotide of the present invention, and a polynucleotide may, but need not, be linked to other molecules and/or support materials.

Polynucleotides may be prepared using any of a variety of techniques known in the art, including, for example, oligonucleotide synthesis. Screening a prepared library with a selected probe may be conducted using standard procedures, such as those described in Sambrook et al., *Molecular Cloning: A Laboratory Manual* (New York: Cold Spring Harbor Laboratory Press, 1989).

The oligonucleotide sequences selected as probes should be sufficiently long and sufficiently unambiguous that false positives are minimized. The oligonucleotide is preferably labeled such that it can be detected upon hybridization to DNA in the library being screened. Methods of labeling are well known in the art, and include the use of radiolabels, such as $^{32}P$-labeled ATP, biotinylation or enzyme labeling. Hybridization conditions, including moderate stringency and high stringency, are provided in Sambrook et al., supra.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., DNA 2:183, 1983).

Nucleotide sequences can be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include plasmids, such as pRS400, pRS40H, pRS40N, pRS40B, pBR322, pIL07 and pIL13, pRS406 and it's derivatives pIL19 and pIL22. Other elements will depend upon the desired use, and will be apparent to those of ordinary skill in the art.

Methods

In one embodiment, the invention provides a method of producing stable plasmid replication in a yeast cell. Also provided is a method of enhancing plasmid replication in a yeast cell. The method comprises transforming a plasmid comprising a nucleic acid molecule of the invention into the yeast cell. The methods comprise transforming a plasmid comprising a nucleic acid molecule of the invention into the yeast cell. The nucleic acid molecule is typically selected from SEQ ID NO: 1-19. In one embodiment, the yeast cell is a member of the genera consisting of *Saccharomyces*, *Lachancea*, *Kluyveromyces*, and *Pichia* (*Komagataella*). In some embodiments, the yeast cell is selected from the group consisting of *Saccharomyces cerevisiae*, *Saccharomyces bayanus*, *Saccharomyces paradoxus*, *Lachancea kluyveri*, *Lachancea waltii*, *Kluyveromyces lactis*, *Kluyveromyces wickerhammii*, *Hansenula polymorpha*, *Pichia pastoris*, and *Naumovozyma castellii*. In one embodiment, the yeast cell is *Pichia pastoris*, and the nucleic acid molecule is SEQ ID NO: 9 or 19. Alternatively, the nucleic acid molecule is one of SEQ ID NO: 14, 15, 17, or 18. In one embodiment, the method of enhancing plasmid replication in a yeast cell is performed in a yeast cell that is not *K. lactis*, *S. cerevisiae*, or *L. kluyveri*.

The invention additionally provides a method of producing a shuttle vector for use in multiple species of yeast. The method comprises introducing a nucleic acid molecule of the invention into a plasmid. The plasmid is typically selected from pRS400, pRS40H, pRS40N, pRS40B, pBR322, pIL07 and pIL13, pRS406 and its derivatives pIL19 and pIL22. The vector can optionally include a selectable marker. In some embodiments, the insertion sites are the unique BamHI or the unique AatII restriction site in these plasmids.

Also described herein is a method of producing an optimized autonomous replicating sequence (ARS). The method comprises generating a library of mutagenized wild type ARSs; growing yeast containing the mutagenized ARSs on selective media; measuring the growth rate of the mutagenized ARSs relative to wild type ARSs; and identifying those mutagenized ARSs that grow at a faster rate on selective media relative to wild type ARS as optimized ARSs. The above method can further comprise sequencing the mutagenized ARSs to identify the mutations the effect the optimization of the ARS.

Kits

For use in the methods described herein, kits are also within the scope of the invention. Such kits can comprise a carrier, package or container that is compartmentalized to receive one or more containers such as vials, tubes, and the like, each of the container(s) comprising one of the separate elements to be used in the method. For example, the container(s) can comprise a nucleic acid molecule that is, optionally, detectably labeled. Optionally, included in the same or a separate container, the kit comprises a vector attached or to be attached to the nucleic acid molecule. The kit can also include one or more containers for a reporter-means bound to a detectable label, e.g., an enzymatic, florescent, or radioisotope label for use in monitoring the nucleic acid molecule. The kit can include all or part of a nucleic acid sequence described herein, or a vector or host cell that includes the nucleic acid sequence described herein.

The kit of the invention will typically comprise the container described above and one or more other containers comprising materials desirable from a commercial and user standpoint, including buffers, diluents, filters, needles, syringes, and package inserts with instructions for use. In addition, a label can be provided on the container to indicate that the composition is used for a specific therapeutic or non-therapeutic application, and can also indicate directions for use, such as those described above. Directions and or other information can also be included on an insert which is included with the kit.

EXAMPLES

The following examples are presented to illustrate the present invention and to assist one of ordinary skill in making and using the same. The examples are not intended in any way to otherwise limit the scope of the invention.

Example 1

Autonomously Replicating Sequence for Use in a Wide Range of Budding Yeasts

This example describes a short ARS sequence that functions in at least 10 diverse species of budding yeast. These include, but are not limited to members of the *Saccharomyces, Lachancea, Kluyveromyces,* and *Pichia (Komagataella)* genera spanning over 500 million years of evolution. In addition to its wide species range, this ARS and an optimized derivative confer improved plasmid stability relative to other currently used ARS modules.

DNA replication is an essential function of cellular biology. It is highly regulated at the initiation stage that occurs at loci termed replication origins. Yeast replication origins retain their initiation activity in a plasmid context allowing autonomous episomal plasmid maintenance (Stinchcomb et al. 1980). This cis-acting autonomously replicating sequence (ARS) function has been useful for both understanding the basic science of DNA replication (Nieduszynski et al. 2007; Liachko et al. 2013) and for industrial applications (Böer et al. 2007).

The well-studied ARSs of the baker's yeast, *Saccharomyces cerevisiae*, are short (<100 bp) modular DNA sequences that require an 11-17 bp core sequence element called the ARS Consensus Sequence (ACS) as well as less well defined flanking sequences (Méchali et al. 2013). The ACS serves as a binding site for the Origin Recognition Complex (ORC), a six-member protein complex that serves as the landing pad for downstream replication initiation machinery.

Large-scale studies have elucidated a diversity of ARS sequence determinants among the budding yeasts. Pre-Whole Genome Duplication (WGD) yeast *Kluyveromyces lactis* uses a 50 bp ACS motif that is very dissimilar from the canonical *S. cerevisiae* ACS (Liachko et al. 2010). Another pre-WGD species, *Lachancea waltii*, uses a motif that resembles a chimeric fusion between the *S. cerevisiae* and *K. lactis* ACS motifs (Di Rienzi et al. 2012) whereas its relative *L. kluyveri* has more relaxed sequence requirements (Liachko et al. 2011). While ARSs have also been described in other yeast species (Iwakiri et al. 2005; Iborra & Ball 1994; Vernis et al. 1997; Wright & Philippsen 1991; Cregg et al. 1985; Yang et al. 1994), the low-throughput nature of the relevant studies has precluded drawing any overarching conclusions about their origin structure.

Due to the diversity of sequences required for origin function in different yeast species, ARSs are usually restricted to function in only a few yeast species. For example, *K. lactis* ARSs rarely work in non-*Kluyveromyces* yeasts and ARSs from other species rarely function in *K. lactis* host cells (Liachko et al. 2010; 2011). On the other hand, *L. kluyveri* is a permissive host species and can utilize most ARSs from *S. cerevisiae* and *K. lactis* (Liachko et al. 2011). The methylotrophic budding yeast *Pichia pastoris* uses at least two different kinds of ARS sequences, neither of which function in *S. cerevisiae* (see Example 2 below). Since ARSs are required for plasmid maintenance, an ARS that functions across all yeasts would be a useful genetic tool to develop shuttle vectors for cross-species studies, but to date such a module does not exist.

We have identified a 452 bp *K. lactis* genomic fragment that retains ARS function in at least 10 budding yeast species with diverse ARS sequence requirements. This sequence (which we have named "panARS") maps to coordinates 781040-781491 bp on chromosome F of the *K. lactis* genome (strain NRRL Y-1140 (Dujon et al. 2004)). The DNA fragment was originally identified as an ARS in *K. lactis* using a predict-and-verify approach used to generate a comprehensive *K. lactis* ARS map (Liachko et al. 2010). This ARS was subsequently cloned into a commonly used ARS-less URA3 vector, pRS406. The resulting plasmid (named pIL20) as well as the original plasmid from the *K. lactis* experiment were used to transform ura3-strains of *S. cerevisiae, S. paradoxus, S. bayanus* var *uvarum, L. waltii, L. kluyveri, K. lactis, K. wickerhamii,* and *P. pastoris*. ARS activity is exhibited by high-transformation efficiency and robust colony formation on selective media. We detected ARS activity (>500 colonies per microgram of transforming plasmid DNA) in all species tested (FIG. 1a).

Additionally, for each species several colonies were re-streaked on selective medium agar plates and inoculated into selective liquid medium where they grew robustly at 30. We were able to recover plasmids from re-streaked colonies and cultures of all species using standard techniques. Sequencing and restriction digestion analysis confirmed the identity of the recovered plasmids to be the same as the input ARS plasmid. Recovered plasmids were used to transform the host species and displayed robust colony formation on selective media in all cases. These results suggest that panARS allows episomal plasmid maintenance in the yeast species listed above. We also detected ARS activity in *Naumovozyma castellii* and *Hansenula polymorpha* when panARS was cloned into vectors bearing antibiotic resistance markers (Chee & Haase 2012).

To delineate the region of panARS required for function in each of the different species we sheared the 452 bp ARS fragment and cloned a library containing ARS sub-fragments. This library was used to transform the different yeast species in order to identify sub-fragments of the ARS that retain function. Short ARS fragments isolated from this screen were also tested for function across multiple species. In this manner we were able to isolate the minimal region of the ARS that confers function across all species to a region near one end of the ARS (FIG. 1b). All species listed except P. pastoris were able to initiate replication with ARS sub-fragments in a region between relative positions 188-316. For ARS function, P. pastoris required ARS DNA fragments within relative coordinates 256-371 (FIG. 1b).

Figure 2A:
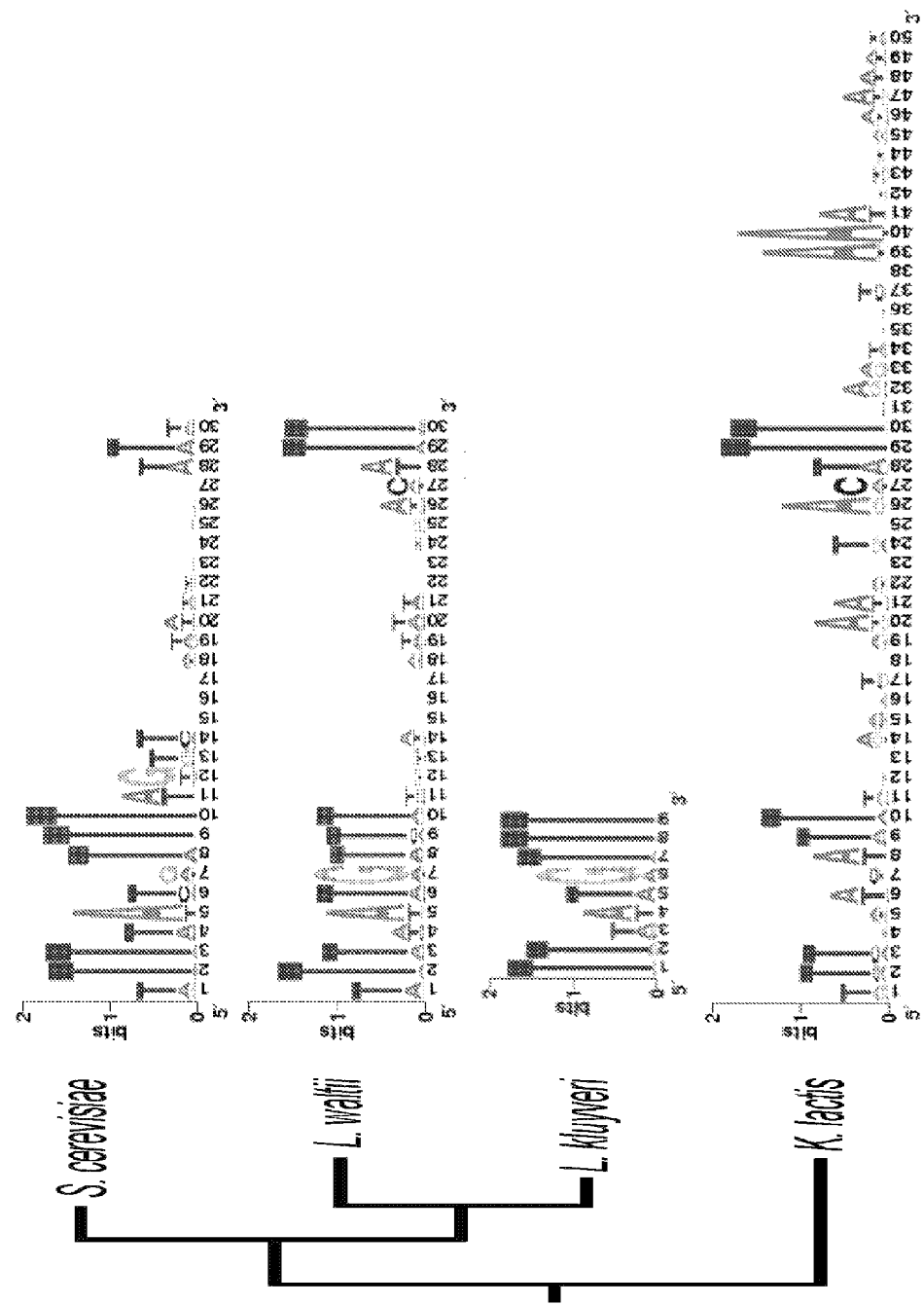
FIGS. 2A-2B. Comparison of ARS Consensus motifs and panARS sequences.
Figure 2B:

We modified the sequence of panARS in an attempt to simultaneously improve its function across multiple species. The sequence determinants of ARS function are not yet understood in most yeasts, precluding targeted optimization across the entire species panel. We introduced mutations into the best match to the S. cerevisiae and K. lactis ACS sequences within the functional panARS region and one strong match to the K. lactis ACS outside the minimal region (since this may be a dimeric K. lactis ARS) to improve the sequence matches to these known motifs (FIG. 2). The resulting mutations improved all motif matches as assayed by the FIMO motif-alignment program (Grant et al. 2011): the q-value of the S. cerevisiae ACS match decreased from 0.003 to 3.11e-05, and the q-value of the two K. lactis ACS matches decreased from 1.6e-08 to 7.25e-11 and from 1.89e-07 to 3.32e-12.

Figure 1C:
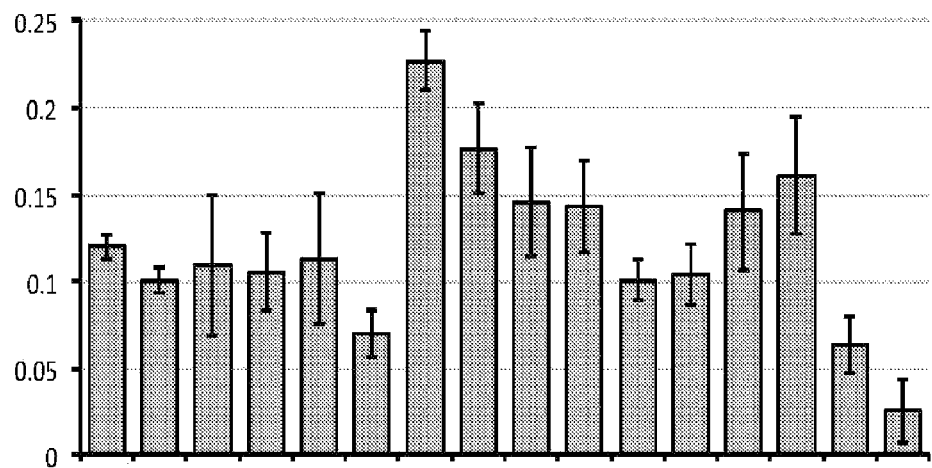

We cloned the full length (452 bp) optimized ARS mutant sequence into vector pRS406 and tested ARS function in different yeast species. The mutant ARS fragment retained robust ARS activity in all species listed above. We also performed plasmid loss assays as described (Donato et al. 2006) to measure relative plasmid stability in the eight aforementioned species (FIG. 1c). The plasmid loss assay (also known as the minichromosome maintenance assay) measures the retention of the plasmid-borne selectable marker during growth in non-selective media. YPD media was inoculated with cells transformed with relevant plasmids and grown for 10-20 generations. Proportions of Ura+ cells within each culture were measured at the start and end of the non-selective growth by plating on YPD and selective agar plates and counting colonies. Plasmids with low or absent ARS activity are quickly lost from the population whereas plasmids with increased ARS activity are more readily retained during non-selective growth. The mutant ARS sequence showed a slightly improved stability (indicated by lower plasmid loss/generation) in the S. cerevisiae, S. bayanus, and L. waltii hosts relative to the original ARS sequence (one-tailed two-sample t-test p-values=0.0007, 0.0403, and 0.0086 respectively). In K. lactis and K. wickerhamii, we did not detect a significant change in plasmid stability between the two alleles (p-values=0.3872 and 0.1678 respectively). This may be due to the fact that this ARS originates from K. lactis and is already maximally efficient. In P. pastoris the optimized ARS showed improved efficiency relative to the wild type sequence (p-value=0.0115).

Figures 3A, 3B:
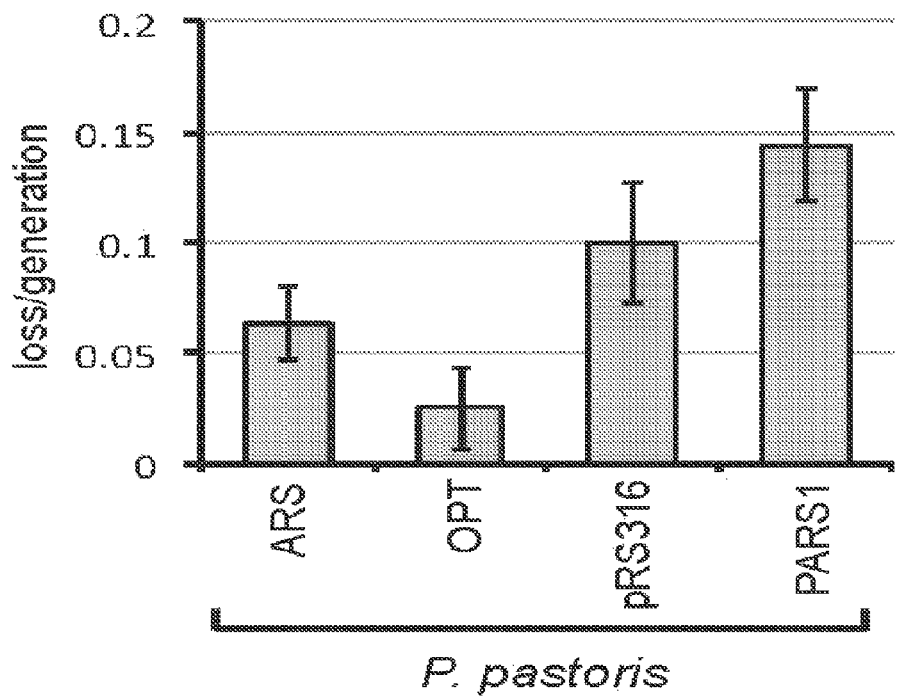
FIGS. 3A-3B. Plasmid loss rates in Pichia pastoris.

We also tested the plasmid loss rate of the same vector backbone bearing the previously described P. pastoris ARS, PARS1. This 167 bp sequence is currently the most commonly used ARS module in P. pastoris (Lee et al. 2005; Cregg et al. 1985). Additionally, we tested the efficiency of pRS316, a S. cerevisiae ARS/CEN plasmid which replicates in P. pastoris. Plasmids carrying both the wild type and optimized ARS alleles were more stable than both the PARS1 plasmid and pRS316 (FIG. 3).

In summary, we have identified a 452 bp ARS element that originates from K. lactis, but also retains ARS function in a number of other species with diverse sequence requirements for initiating DNA replication. The synthetically optimized mutant version of this sequence performs either equivalently to or better than the wild type sequence. Additionally, this module performs significantly better than other characterized ARS plasmids in P. pastoris, with a stability that resembles ARS/CEN plasmids in better-studied models. These results suggest that panARS provides an efficient ARS module in other related yeast species and a superior construct even when cross-species performance is not required.

References Cited in Example 1

Böer E, et al. (2007) Appl. Microbiol. Biotechnol. 77: 513-523.
Broach J R, et al. (1983) Cold Spring Harb. Symp. Quant. Biol. 47 Pt 2: 1165-1173.
Chee M K & Haase S B (2012) G3 (Bethesda) 2: 515-526.
Gregg J M, et al. (1985) Mol. Cell. Biol. 5: 3376-3385.
Di Rienzi S C, et al. (2012) Genome Res. 22: 1940-1952.
Donato J J, et al. (2006) PLoS Genet. 2: e141.
Dujon B et al. (2004) Nature 430: 35-44.
Grant C E, et al. (2011) Bioinformatics 27: 1017-1018.
Iborra F & Ball M M (1994) Yeast 10: 1621-1629.
Iwakiri R, et al. (2005) Yeast 22: 1049-1060.
Lee C C, et al. (2005) Plasmid 54: 80-85.
Liachko I et al. (2011) BMC Genomics 12: 633.
Liachko I, et al. (2010) PLoS Genet. 6: e1000946.
Liachko I, et al. (2013) Genome Res. 23: 698-704.
Méchali M, et al. (2013) Curr. Opin. Genet. Dev. 23: 124-131.
Nieduszynski C A, et al. (2007) Nucleic Acids Res. 35: D40-D46.
Stinchcomb D T, et al. (1980) Proc. Natl. Acad. Sci. U.S.A. 77: 4559-4563.
Vernis L, et al. (1997) Mol. Cell. Biol. 17: 1995-2004.
Wright M C & Philippsen P (1991) Gene 109: 99-105.
Yang V W, et al. (1994) Appl. Environ. Microbiol. 60: 4245-4254.

TABLE 1

Strains and plasmids used in Example 1

| Strains | | |
|---|---|---|
| name | species | source |
| W303-1a | S. cerevisiae | R. Rothstein |
| YDG613 | S. paradoxus | D. Greig |
| YZB5-113 | S. bayanus | Y. Zheng |
| N/A | L. waltii | B. Brewer |
| FM628 | L. kluyveri | M. Johnston |
| ILY538 | K. wickerhamii | spontaneous FOAr revertant of strain Y-8286 |
| MW98-8c | K. lactis | C. Newlon |
| JC308 | P. pastoris | J. Cregg |
| 4310 | N. castellii | D. Bartel |
| Y-5445 | H. polymorphs | USDA Agricultural Research Service |

| Plasmids | |
|---|---|
| name | features |
| pRS406 | ampr, URA3 |
| pIL20 | pRS406, panARS |
| pIL57 | pRS406, optimized panARS |
| pRS400 | ampr, G418 |
| pIL48 | pRS400, panARS |
| pRS40H | ampr, HygB |
| pIL50 | pRS40H, panARS |

Example 2

Optimizing Replication Origin Activity in the Methylotrophic Yeast *Pichia pastoris*

This example comprehensively profiles replication origin location, structure, and dynamics in the methylotrophic budding yeast *Pichia pastoris* (*Komagataella phaffii*) [31, 32] using a number of massively parallel sequencing techniques. In addition, we generated a genome-wide profile of nucleosome occupancy. The findings show that this yeast, which is commonly used for industrial production of recombinant proteins [33], employs at least two distinct types of DNA sequences to initiate replication. Approximately one third of *P. pastoris* ARSs require a G/C-rich motif that closely matches one form of the binding site of the well-studied Hsf1 transcriptional regulator [34]. The remaining origins use A/T-rich sequences for initiation. Genome regions near G/C-rich origins replicate significantly earlier than regions near the other class of origins and have a unique pattern of nucleosome organization. Their organization suggests that local transcriptional regulation may be linked in some way to replication timing at these sites. Furthermore, the most common plasmid vector used in *P. pastoris* contains a member of the AT-rich class of origin, suggesting that use of plasmids bearing a G/C-rich origin will yield immediate improvements for strain engineering.

Results

Global Mapping of *P. pastoris* ARSs

Figure 4A:
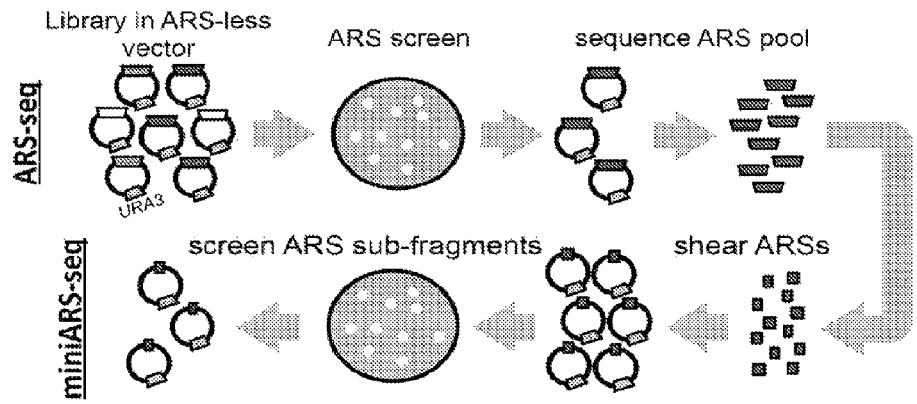
FIGS. 4A-4D. Mapping of replication origins in P. pastoris.

The classic ARS screen identifies sequences sufficient for the initiation of replication of plasmids [35, 36] by assaying for colony formation on selective medium. Non-replicating plasmids do not yield colonies. An early study identified two regions of the *P. pastoris* genome that have ARS function, but do not have ACS elements seen in *S. cerevisiae* ARSs [37]. To generate a comprehensive map of ARSs in the genome of *P. pastoris* (PpARSs) we utilized ARS-seq, a high-throughput ARS screen combined with deep sequencing (FIG. 4A) [38]. A ~15× library of genomic DNA fragmented by one of four "four-cutter" restriction enzymes was constructed in a non-replicating URA3 shuttle vector. A *P. pastoris* ura3 strain (JC308) was transformed with this library and plated on medium lacking uracil (C-Ura) resulting in ~20,000 colonies from an estimated 2-3×10$^6$ transformants. Colonies were replica-plated on C-Ura plates and grown for four additional days before the growing colonies were pooled. Total DNA was extracted from pooled cells. ARS inserts were amplified using vector-specific Illumina primers and sequenced using paired-end deep sequencing. The sequencing reads were assembled into 971 unique genomic fragments (averaging 661 bp in length) and 358 overlapping contigs. The data were filtered both computationally and by manual verification (Methods) resulting in a final list of 311 ARS loci.

To delineate the functional regions of *P. pastoris* ARSs with greater precision we used miniARS-seq, a follow-up ARS screen where the input library is constructed from short subfragments of ARSs isolated from the initial ARS-seq screen (FIG. 4A) [38]. The miniARS-seq screen returned 14,661 functional ARS fragments that were filtered and assembled into contigs (Methods). This procedure narrowed the functional regions of 100 ARSseq contigs to ~150 bp. We have previously shown that ARS regions can be accurately narrowed by inferring functional "cores" based on regions of overlap among multiple ARS-seq/miniARS-seq fragments [38]. We combined data from both screens to generate a high-resolution map of ARS sites in the *P. pastoris* genome.

At Least Two Classes of ARSs in *P. pastoris*

Figure 4B:
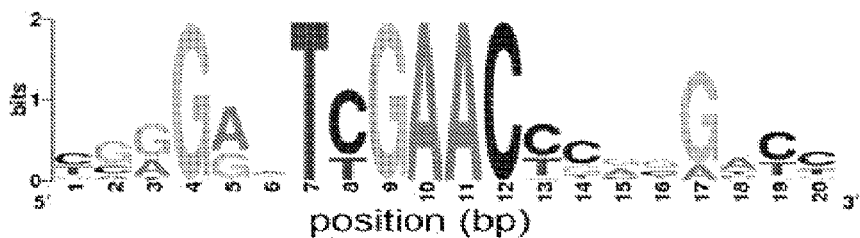
Figure 4C:
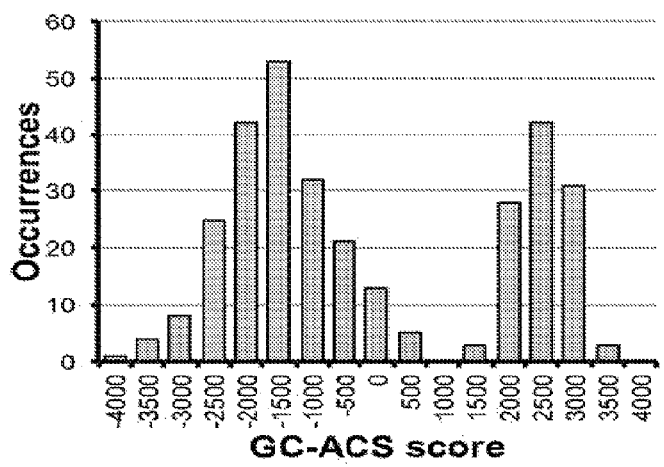

Identification of conserved motifs within a set of sequences with a shared function is one of the cornerstones of comparative genomics. The *S. cerevisiae* ACS motif is present in all *S. cerevisiae* ARSs and is easily recognizable by motif discovery algorithms [39-42]. The same is also true for *L. waltii* [29], and in *K. lactis* the ACS motif can additionally be used to predict accurately genomic ARS locations [27, 43]. We used the de novo motif discovery tool MEME [44] to identify conserved motifs of varying lengths within the entire set of *P. pastoris* ARSs using the zero or one occurrence per sequence (zoops) setting. MEME identified a 20 bp G/C-rich consensus motif ("GC-ACS," E-value=1.3e-248) with a TYGAAC core (FIG. 4B). However, not all PpARSs have a significant match to this motif. To determine the subset with a GC-ACS, we used the MAST algorithm to assign a score to the best occurrence of the motif within each sequence. The bimodal distribution of motif scores (FIG. 4C) indicated that 107/311 (34.4%) of the ARSs have much stronger matches to the motif than the remaining 204 ARSs. We were unable to detect any conserved motifs that were present among these 204 sequences.

We found that *P. pastoris* ARSs were significantly enriched for G/C-content relative to combined intergenic sequences (binomial P=1.778e-06). Furthermore, the 107 ARSs bearing the GC-ACS motif ("GC-ARSs") were significantly enriched (binomial exact test P=2.825e-15) for G/C-content relative to the 204 ARSs without the motif ("AT-ARSs"). In fact, the AT-ARSs alone are not significantly enriched for G/C or NT content relative to all of intergenic DNA (two-sided binomial exact test P=0.46), suggesting that GC-ARSs are chiefly responsible for the overall G/C enrichment in the ARS dataset. Additionally, while both classes of ARSs are predominantly intergenic, GC-ARSs associate with longer intergenes whereas AT-ARSs do not. The median length of all intergenes in the *P. pastoris* GS115 strain background is 216 bp [31], whereas the median length of GC-ARS intergenes is 869 bp, an enrichment that cannot be explained by the length of intergenes alone (Monte Carlo simulation P<0.01). In contrast, the median AT-ARS intergene at 566 bp is not significantly longer than the background (Monte Carlo simulation P=0.85). Another difference between the GC- and AT-ARSs is that the average combined ARS-seq read depths for individual ARSs of the AT-class are lower than for those of the GC-ARS class (one-tailed T-test P=0.035). This difference is most noticeable in that 61/204 AT-ARSs have a read depth <20, while all GC-ARSs have higher read depths, and only 9/107 GC-ARSs have read depths of <300. We validated a number of these low read depth AT-ARSs to ensure that they are not all false positives. This discrepancy in read depth between GC- and AT-ARSs suggests that the AT-ARS dataset may be enriched for ARSs that replicate less efficiently in this plasmid vector context.

Similarly to other budding yeast ARSs, PpARSs are predominantly intergenic (hypergeometric test P<2.2e-16). However, unlike *S. cerevisiae*, where replication origins are enriched in convergently transcribed intergenes (where both adjacent genes are transcribed toward the intergene), *P. pastoris* ARSs are depleted in convergent intergenes (Chi-squared P=4.749e-05).

Figure 4D:
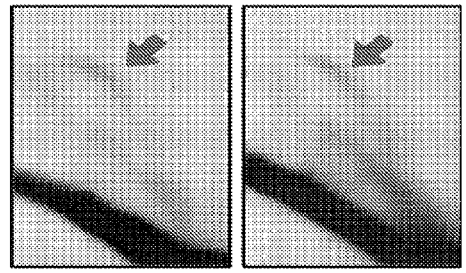
Figure 9:
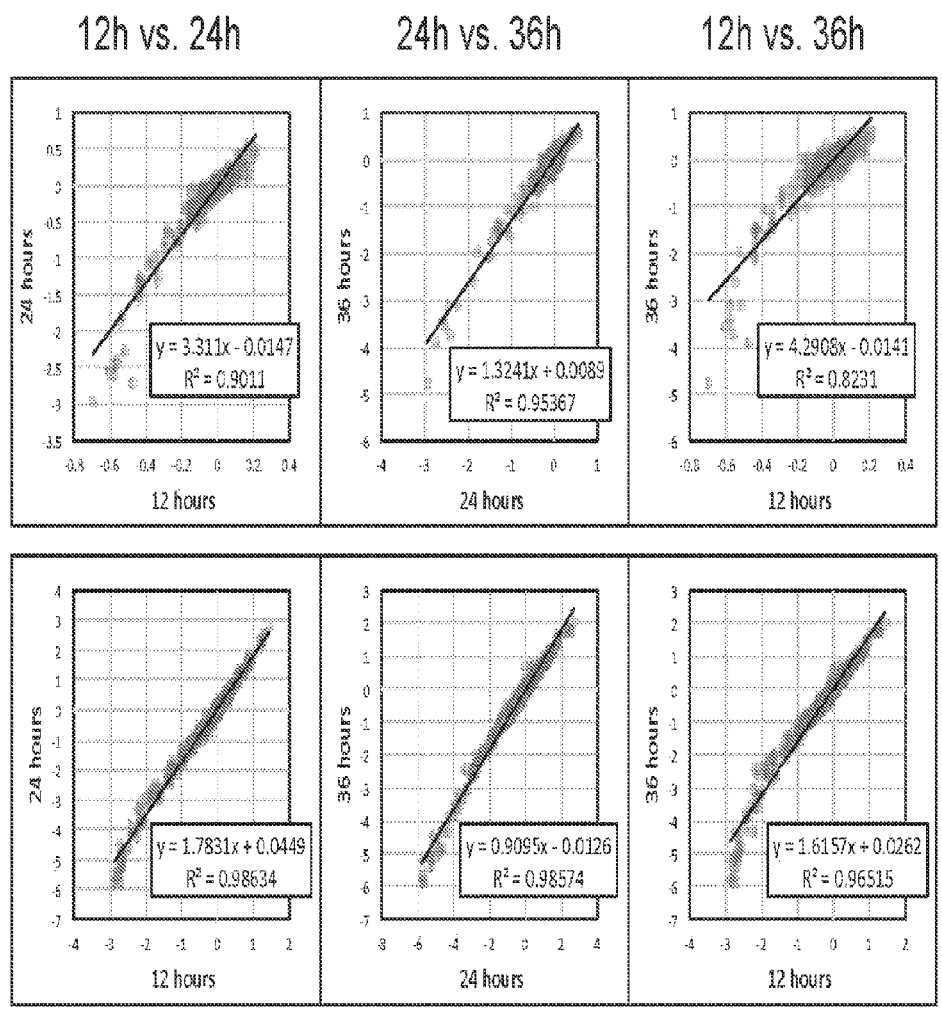
FIG. 9. Comparisons of mutARS-seq data during competitive growth. Averaged mutARS-seq data from 12-, 24-, and 36-hour timepoints are plotted as scatterplots. Upper panels, ARS-C379; lower panels, ARS-A2772. Left column plots 24 hrs vs. 12 hours; center plots 36 hrs vs. 24 hrs; right plots 36 hrs vs. 12 hrs. From left to right, upper panel: y=3.311x−0.0147; $R^2$=0.9011; y=1.3241x+0.0089, $R^2$=0.95367; y=4.2908x−0.0141, $R^2$=0.8231; and lower panel: y=1.7831x+0.0449, $R^2$=0.98634; y=0.9095x−0.0126, $R^2$=0.98574; y=1.6157x+0.0262, $R^2$=0.96515.

To confirm that both GC-ARSs and AT-ARSs are bona fide replication origins in their chromosomal context, we assayed genomic origin firing by 2D-gel electrophoresis at two genomic loci (FIG. 4D). Replication intermediates were isolated from exponentially growing cells in YPD medium, subjected to 2D-gel electrophoresis as described [45], and probed for a GC-ARS locus (C379) and an AT-ARS locus (A2772). The presence of an upper arc on a 2D-gel blot results from replication bubble intermediates (FIG. 4D, arrows) and is indicative of replication initiation at the probed locus. We detected such "bubble arcs" at both loci, suggesting that members of both classes of sequences can function as replication origins in the genome.

The GC-ACS Motif is Required for GC-ARS Function

Figure 5:
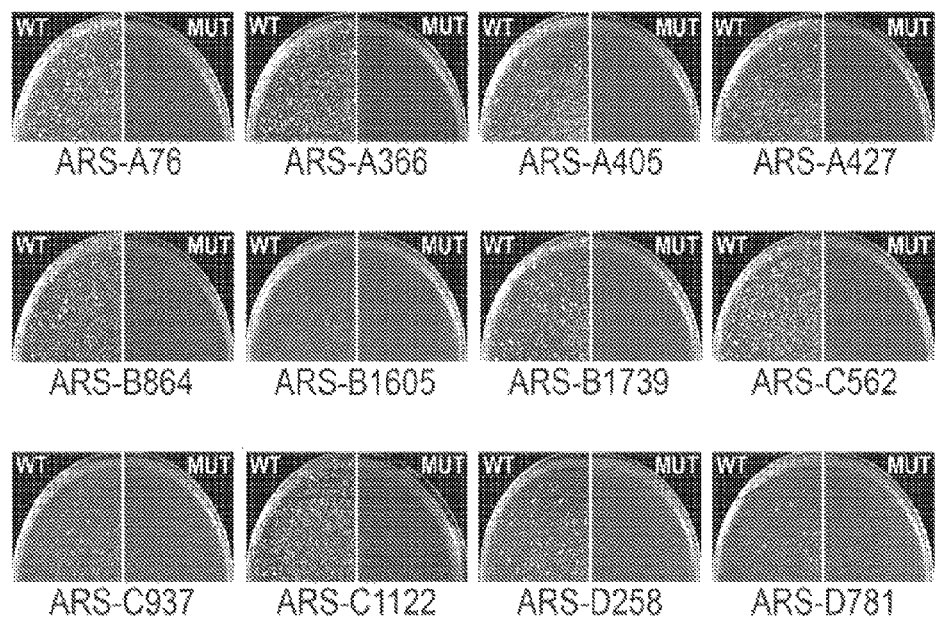
FIG. 5. The GC-ACS is required for GC-ARS function. Wild type (WT) and mutant (MUT) alleles of the twelve ARSs indicated were cloned into a URA3 ARS-less vector and used to transform ura3 yeast on selective medium plates lacking uracil. Plates were grown at 30 for five days before pictures were taken. Colony formation indicates plasmid maintenance and ARS activity. The GC-ACS was positioned <15 bp away from the 5' endpoint in all ARS sequences. The sequences of the fragments tested are provided in the accompanying Sequence Listing (SEQ ID NO: 20-59).

To test whether the GC-ACS identified from the sequence analysis is required for GC-ARS function, we used site directed mutagenesis to disrupt the motif within twelve different GC-ARSs and tested the effect of these mutations on ARS function (FIG. 5). We replaced the central GA dinucleotide within the best match of the GC-rich motif with a CC dinucleotide to disrupt the motif (TYGAAC. SEQ ID NO: 60, was changed to TYCCAC, SEQ ID NO: 61). We ligated short DNA fragments (125 bp) bearing both wild type and mutant alleles of each ARS into a URA3 plasmid and tested the resulting plasmids for ARS function by transformation of the P. pastoris ura3 strain (FIG. 5). Multiple individual clones of all plasmids carrying wild-type ARS alleles yielded colonies on selective media indicating ARS activity. All clones were functional, regardless of the relative orientation of the ARS insert within the vector. Three of the twelve wild-type ARSs (ARS-B1605, ARS-C937, and ARS-D781) showed a noticeably weaker ARS activity indicated by slower colony growth. This slow growth is likely due to the short fragment length of ARSs tested, since multiple flanking elements are commonly required to support or enhance ARS function. None of the clones bearing mutant ARS alleles showed colony formation indicating the absence of ARS function independent of insert orientation within the vector. Additionally, in all twelve cases, the wildtype ARSs retained function despite the GC-ACS being positioned <15 bp from the 5' end of the ARS fragment. These results indicate that the GC-ACS motif is required for GC-ARS function whereas sequences flanking the motif on the 5' side are not.

At Least Two Distinct Motifs can Drive ARS Function in P. pastoris

While the GC-ACS motif is not present in all PpARSs, the fact that it is present in over a third of ARS fragments and is essential for ARS function in the subset of GC-ARSs tested suggest that it plays an important role in ARS function. This hypothesis is further supported by the fact that ARS-seq identified most of the intergenic matches of this motif (106/134) across the genome. The remaining twenty-eight intergenic occurrences of this motif that were not detected by ARS-seq have significantly lower match scores than the motifs within ARS fragments (T-test P=1.49e-07) suggesting that strong matches to the GC-ACS are good indicators of ARS activity.

To assay directly the sequence determinants of ARS function, we applied a deep mutational scanning [46, 47] approach, mutARS-seq [38], to 100 bp fragments of P. pastoris ARS-C379 and ARS-A2772. This method involves competitively growing yeast transformed with a library of randomly mutagenized variants of a given ARS and measuring the enrichment of each allele through paired-end deep sequencing of samples over time (FIGS. 6A, and 7-9). Stronger ARS variants increase in population frequency over the course of the competition and are given positive enrichment scores, whereas deleterious mutations result in depletion of these alleles and are given negative enrichment scores. We constructed mutARS-seq libraries for ARS-C379 and ARS-A2772 using oligonucleotides synthesized with a 2% chance of bearing a random mutation at each position. Each library contained >20,000 inserts. A ura3 strain of P. pastoris was transformed with the two libraries separately (two biological replicates for each library). Resulting colonies on selective medium plates (~100,000 transformants for each experiment) were pooled and the cell mixture was used to inoculate a 1 L culture of liquid selective medium. The culture was grown at 30 and the abundance of each ARS variant at different times was measured by 101 bp paired-end sequencing.

Figure 6A:
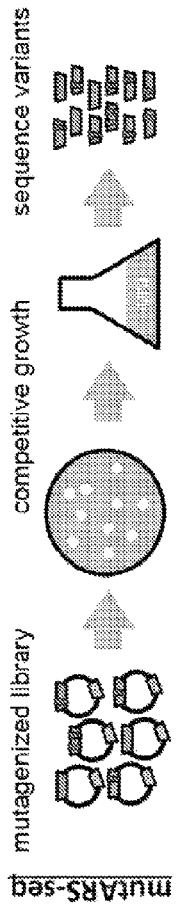
FIGS. 6A-6C. Deep mutational scanning of P. pastoris ARSs.
Figure 6B:
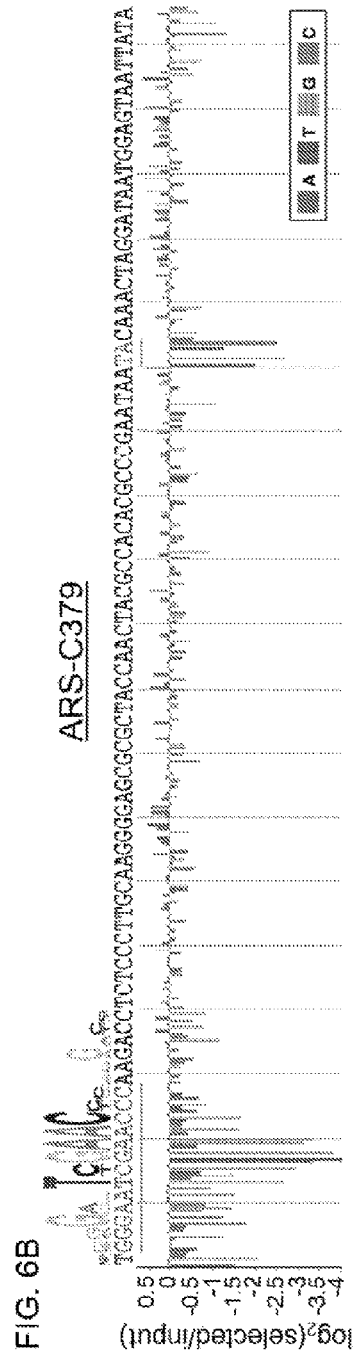
Figure 6C:
Figure 7:
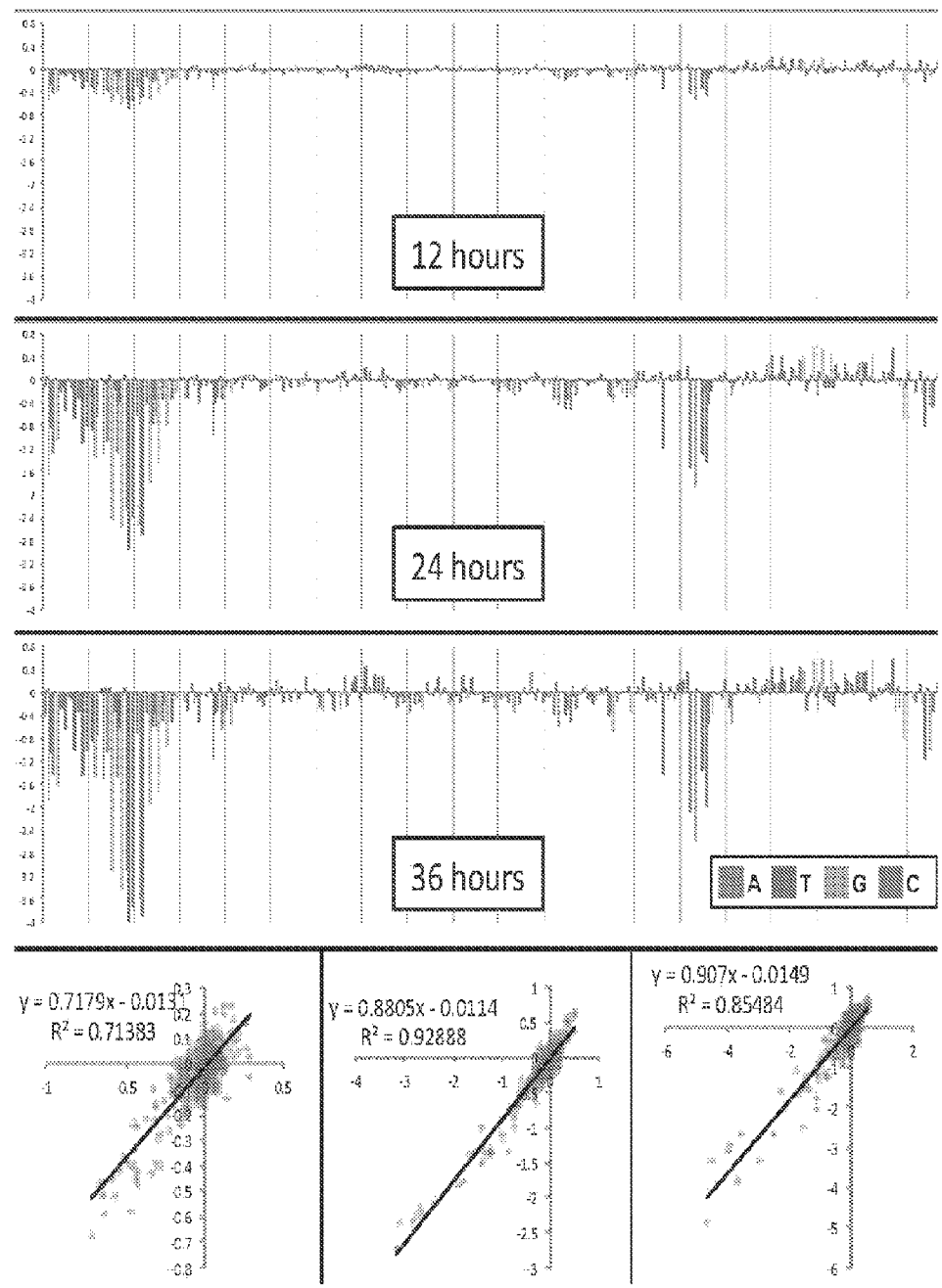
FIG. 7. ARS-C379 mutARS-seq data during competitive growth. Data processed as described in Example 2 is shown as the average of two replicates for 12-, 24-, and 36-hour timepoints normalized against the same input sample. In each of the 3 upper panels, the y axis represents $\log_2$ (enrichment ratio), and the scale ranges from −4 to 0.8. Data are plotted on the same y-axis scale to aid visual comparison. Scatterplots show correlations between replicates of the same timepoint samples (lower panels; replicate 1× replicate 2). Lower left panel: y=0.7179x−0.0131, $R^2$=0.71383; lower middle panel: y=0.8805x−0.0114, $R^2$=0.92888; lower right panel: y=0.907x−0.0149, $R^2$=0.85484.
Figure 8:
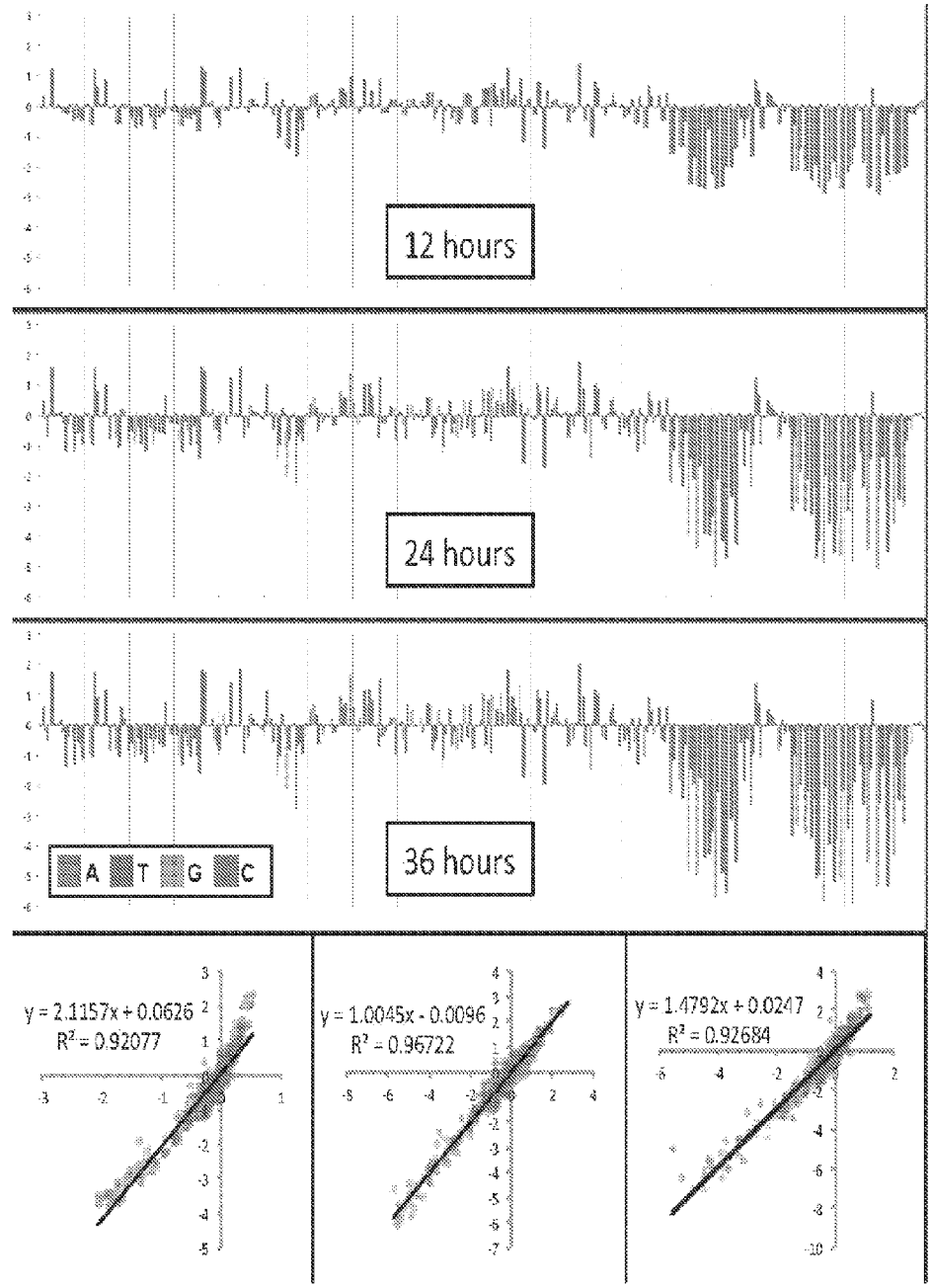
FIG. 8. ARS-A2772 mutARS-seq data during competitive growth. Data processed as described in Example 2 is shown as the average of two replicates for 12-, 24-, and 36-hour timepoints normalized against the same input sample. In each of the 3 upper panels, the y axis represents $\log_2$ (enrichment ratio), and the scale ranges from −6 to 3. Data are plotted on the same y-axis scale to aid visual comparison. Scatterplots show correlations between replicates of the same timepoint samples (lower panels; replicate 1× replicate 2). Lower left panel: y=2.1157x−0.0727, $R^2$=0.92077; lower middle panel: y=1.0045x−0.0096, $R^2$=0.96722; lower right panel: y=1.4792x−0.0247, $R^2$=0.92684.

The results of mutARS-seq show a striking difference in the sequences required for function of the two types of PpARSs. ARS-C379 shows a zone of constraint within the region corresponding to the match of the GC-ACS motif (FIGS. 6B and 7) further supporting that the GC-ACS motif is required for ARS-C379 function. In contrast, ARS-A2772 does not have a GC-ACS and shows a region of constraint at a repetitive NT-rich sequence that is not present in ARS-C379 (FIGS. 6C and 8). In searching for matches to the A/T-rich motif within the ARS set we were able to detect strong matches within only two sequences, one of them being ARS-A2772. This result suggests further complexity within the AT-ARS functional determinants. Alternatively, this motif may be inherently elusive to alignment-based methods due to its repetitive A/T-rich structure. Our findings demonstrate that P. pastoris can utilize at least two different non-overlapping sequence motifs for the initiation of DNA replication. We also found that these ARSs retained function in both orientations within the vector, on different length inserts, and in other plasmid contexts, suggesting that at least one of these sequences, or an equivalent, must be present for the initiation of plasmid replication and that each is sufficient for initiation.

GC-ARSs are Earlier Replicating than AT-ARSs

While the ARS assay can be used for high-precision mapping of sequences required for replication initiation, it is not an accurate measure of origin activity in the genomic context. No correlation between ARS activity and genomic replication timing has been detected in either S. cerevisiae or S. pombe, presumably due to higher-level regulation of timing that is absent on plasmids. To overcome this limitation of the ARS assay, we used an approach that combines cell sorting and deep sequencing [17, 48, 49] to map the temporal patterns of replication within the P. pastoris genome. This method calculates the DNA copy number ratio between S phase and G1 phase cells in sliding windows across the genome. Since a replicated region is present in twice the copy number of a non-replicated region, this copy number ratio is proportional to the relative mean replication time of a given locus [49, 50].

Approximately 1.5 million G1 and S phase cells were sorted from an exponentially growing culture using FACS. Total genomic DNA was isolated, randomly sheared, and sequenced to high coverage to measure the relative DNA copy number of all genomic loci. The ratios of sequence reads between G1 and S phase samples were calculated in non-overlapping 1 kb sliding windows across the genome and normalized based on the total number of reads within each sample (Methods). The resulting ratios from biological replicates were LOESS smoothed, yielding highly reproducible replication timing curves (Pearson and Spearman cor >0.94). To generate a composite replication timing profile, the unsmoothed ratios from both replicates were averaged, normalized to a baseline value of 1 and smoothed (Methods).

Figures 10A, 10B, 10C, 10D:
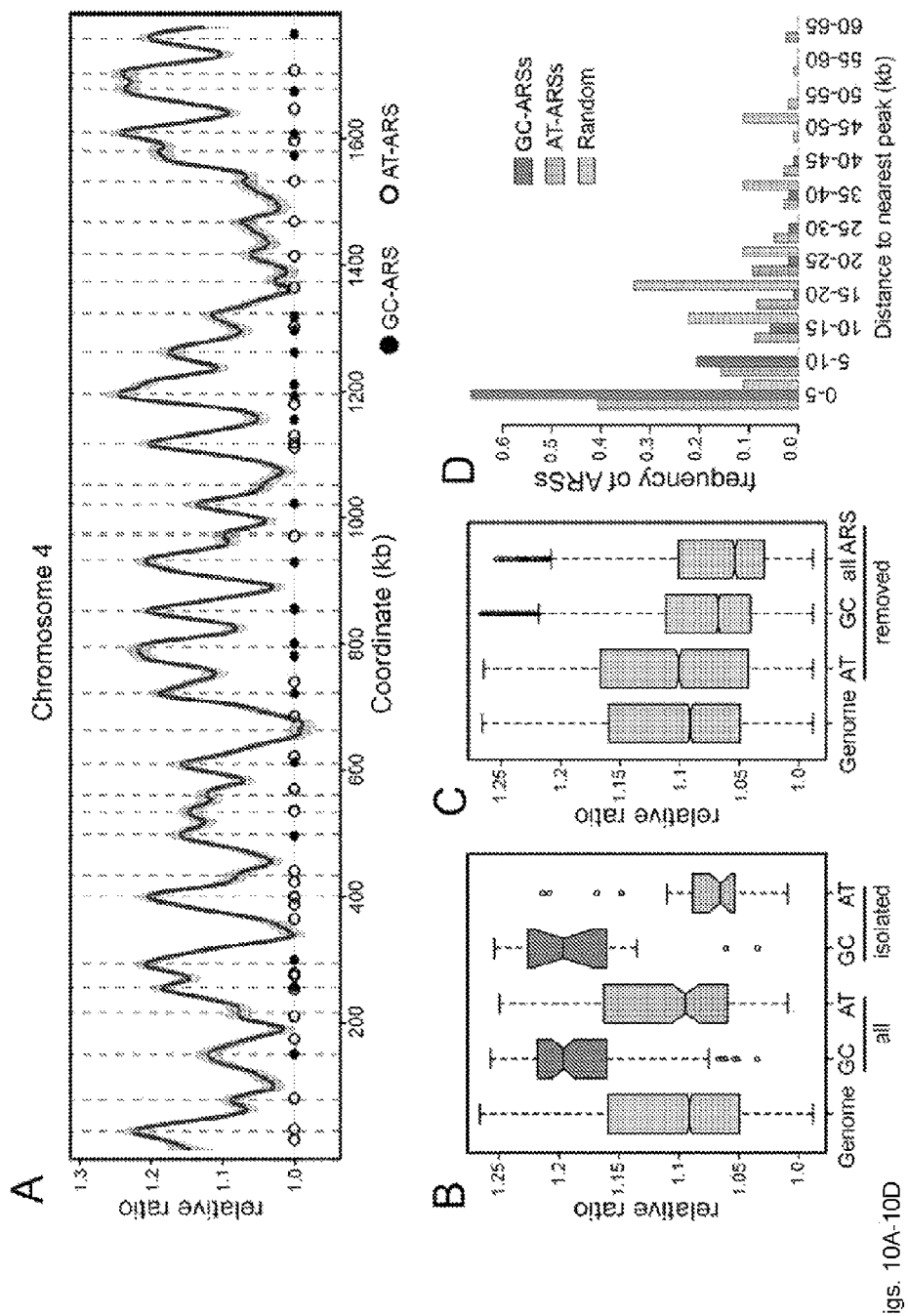
FIGS. 10A-10D. Replication timing of the P. pastoris genome.
Figure 11:
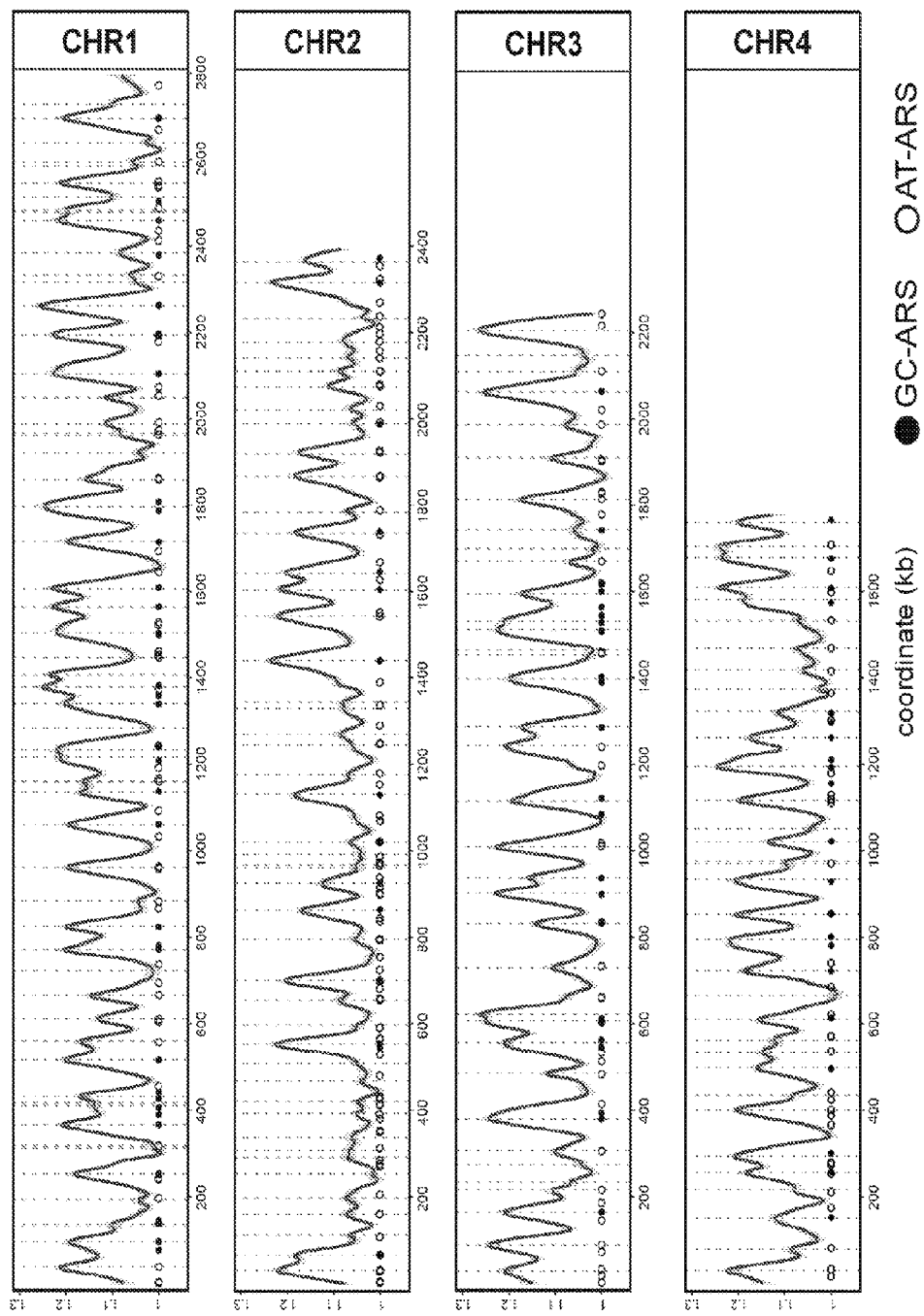
FIG. 11. Replication profiles of all *P. pastoris* chromosomes. Replication timing profiles were computed as discussed (see FIG. 10) and are shown for all four *P. pastoris* chromosomes. Un-smoothed ratio data for one of the replicates is shown in grey. Locations of GC-ARSs and AT-ARSs are indicated by open and shaded circles respectively.

Visual inspection of the chromosome replication profiles revealed ~100 significant peaks corresponding to early replicating regions, or replication origins (FIGS. 10A and 11), as well as valleys that reflect replication termination loci. Additionally, we detected numerous small peaks and "shoulders" (small peaks at the edges of larger peaks) that we interpret to be later firing or less efficient origins. Quantitative analysis identified 176 peaks in replication timing peaks (FIGS. 10 and 11). Overlaying ARS coordinates with the replication curve showed that all large peaks except one contained at least one ARS. Examination of the sequence within the lone ARS-less peak (near position 1,565,000 on chromosome 1) revealed two strong matches to the GC-ACS motif within 2 kb of the peak. Manual validation of 200 bp fragments centered on each of the motif occurrences revealed them both to have ARS function indicating that they are ARS-seq false negatives. We also used the replication timing data to further validate the ARS screen to remove false positives. We manually validated low coverage ARS-seq fragments that did not appear to map at a replication peak. From forty-nine fragments with a read-depth 2-10 (fragments with read-depth 1 are filtered out at the ARS-seq stage; see Methods) eleven did not appear close to peaks and were manually tested for ARS function. Among these eleven (none of which had GC-ACS motifs), ARS activity was detected for only three.

To test whether ARSs bearing the GC-ACS motif are regulated differently than those without, we compared the replication curve values between the two classes of ARSs (FIG. 10B). Our data show that while GC-ARS regions are replicated significantly earlier than the background genomic distribution, AT-ARSs are not (T-test P<2.2e-16 and 0.0699 respectively). Consistently, GC-ARSs are replicated earlier than AT-ARSs (T-test P<2.2e-16). This result holds true even if only loci without neighboring ARSs (within a two-sided 40 kb window) are compared (T-test P=6.267e-07). Chromosomal regions with single isolated AT-ARSs replicate significantly later relative to the pool of all AT-ARSs (T-test P=0.0003), suggesting that clustering of these elements increases their local replication signal. This effect was not seen at the GC-ARS loci (T-test P=0.88), indicating that clustering does not significantly affect their timing.

Another way to detect differences in replication timing between the two classes of ARSs is to measure the effect of removing their signals from the genomic dataset (FIG. 10C). Removing all points within 30 kb windows centered on GC-ARSs significantly shifted the distribution of remaining replication timing signals in the "later" direction (T-test P<2.2e-16). On the other hand, removing signals around AT-ARSs did not significantly affect the distribution of remaining points (T-test P=0.07094). When signal was removed around all ARSs, it shifted the distribution relative to removing just GC-ARSs (T-test P<2.2e-16), consistent with the AT-ARSs occupying a lower tier in the hierarchy of origin activation times.

Additionally, we found the distance from each ARS to the nearest replication peak and plotted histograms of these distances for AT- and GC-ARS's (FIG. 10D). We find that both types of ARSs are significantly associated with peaks (Kolmogorov-Smirnoff test, P=7.18×10e-5 for GC-ARSs and P=0.0293 for AT-ARSs). GC-ARS's were significantly closer to peaks than AT-ARS's (Kolmogorov-Smirnoff test, P=6.13×10e-7). Taken together, our data suggests that while both types of ARSs correlate with genomic replication origins, GC-ARSs are more often found associated with early origins and early replicating regions, whereas AT-ARSs show the opposite tendency.

Nucleosome Positioning at P. pastoris Origins

One common feature of replication origins is a nucleosome depletion region (NDR) close to the site of initiation [13, 14, 26, 30, 51, 52]. To investigate whether this feature holds true for P. pastoris, we generated a complete map of nucleosome positions within the P. pastoris genome by sequencing genomic DNA digested with micrococcal nuclease [53]. Our results revealed gross nucleosome positioning features similar to those seen in other yeasts, such as an NDR at transcriptional start sites (TSS) followed by regularly positioned nucleosomes within the body of transcripts [54, 55]. This result suggests that our experimental methods accurately captured the positions of nucleosomes in this strain. We also detected NDRs at replication origin sites; however, GC-ARS and AT-ARS sites showed striking differences in nucleosome occupancy relative to other budding yeasts [13, 14, 29]. When centered on the GC-ACS, we observed a relative depletion in nucleosome occupancy approximately 40 bp to the 5' side of the motif (in the TYGAAC orientation). However, unlike other yeast origins where the NDR spans the length of approximately one nucleosome, the P. pastoris GC-ARS depletion region spans approximately 450 bp and appears to be excluding three nucleosomes. On the other hand, AT-ARS sites showed a nucleosome depletion region of ~150 bp in length, a pattern more closely resembling that in other budding yeasts. However, this NDR was not flanked by well-ordered nucleosomes at all AT-ARS sites and suggests either that there are key regulatory differences with other budding yeasts or that not all AT-ARSs use the same sequence determinant for origin firing.

Genome Location and Motif Sequence Identify a Class of Origins Associated with Promoters The underrepresentation of GC-ARSs in convergently transcribed intergenes suggests that these elements may be associated with promoters. As in promoters, the NDR near GC-ACS sites is followed by regularly spaced nucleosomes. To test the putative association of the GC-ACS with gene promoters, we searched for this motif in the regulatory motif databases and found that it is a match to one of the motifs annotated as the binding sites of the human Hsf1 [34] heat shock factor (HSF) transcriptional regulator [56] (factor-book.org/mediawiki/index.php/HSF1). Additionally, when centered on the GC-ACS motif (in the TYGAAC orientation), GC-ARSs show a pronounced poly(dA) region around 10 bp to 35 bp upstream of the motif. Notably, this poly(dA) tract is not present near the non-ARS occurrences of this motif and is not required for ARS function (FIG. 5). It has been previously shown that such a neighboring poly(dA) region is a conserved feature of Hsf1 binding sites in the sensu stricto group of budding yeasts [57], though we note that the TYGAAC portion of the motif does not match the canonical budding yeast HSF motif. To determine whether the GC-ACS is likely to be a binding site for Hsf1 or one of its homologs, we aimed to test whether this motif is overrepresented in promoters of genes likely to be regulated by HSF. We used BLAST to identify homologs of S. cerevisiae genes regulated by HSF [58] and filtered the list to include only strong matches (PBLAST E-value<1e-10), resulting in a set of 120 gene homologs. We used the FIMO algorithm to identify significant matches to the GC-ACS within 500 bp regions upstream of all 5037 P. pastoris genes. We identified 451 genes that had GC-ACS motifs and 716 genes with matches to the HSF binding site (the Heat Shock Element, HSE [56, 59]), within 500 bp upstream of the start codon. In our set of 120 potential HSF-regulated P. pastoris genes, 45 had at least one match to the HSE (hypergeometric test P=3.1e-11) and 16 genes had GC-ACSs within 500 bp upstream of the start codon (hypergeometric test P=0.037).

We also used an independent approach to test whether GC-ACS motifs associate with HSE motifs throughout the genome. We mapped separately all occurrences of the GC-ACS and of the HSE. We then assigned to each motif occurrence the nearest annotated gene. There are 5037 annotated genes in *P. pastoris*. From these, 1,188 unique genes were assigned as closest gene to an occurrence of the GC-ACS and 1,236 unique genes were assigned as closest to an HSE. A significant number (524) of unique genes were present in both lists, suggesting an association between GC-ACS and HSE motifs (hypergeometric test P=4.6e-67). While HSF function in *P. pastoris* has not been studied, these results show an enrichment of GC-ACS motifs in regions likely to be regulated by HSF. Furthermore, the GC-ACS motif is positioned close to TSSs and ORF start sites upstream of the motif suggesting some functional overlap between transcription and early origin firing.

Since the GC-ACS is associated with promoters, it raises the possibility that transcription is required for origin activation. If this possibility were true, then the DNA between the GC-ACS and the TSS may be required for ARS function. Since miniARS-seq screens large numbers of randomly sheared ARS sub-fragments, we were able to test this possibility by determining what sequences flanking the GC-ACS are required for ARS function. Using the full list of inferred functional ARS cores we calculated the length of sequence between the edge of the consensus motif and the edge of the ARS core on either side of the motif. The distributions of 5' and 3' lengths show that several GC-ARSs require <10 bp of sequence on the 5' of the GC-ACS while more ARS sequence is required on the 3' side of the motif. In fact, the fragment of ARS-C379 that was used for mutARS-seq (FIG. 6A) retained function with only 2 bp of ARS sequence to the 5' side. Additionally, the twelve wild-type ARS fragments that were tested for activity (FIG. 5) all contained <15 bp of sequence to the 5' of the GC-ACS. The fact that all tested ARSs retained function in the absence of 5' flanking DNA shows that this region, and the 5' poly(dA) sequence, are not required for GC-ARS function. While it is possible that transcription can initiate at ectopic sites in the plasmid, these results suggest that transcription per se may not be required for GC-ARS function in *P. pastoris*. Consistent with these findings, we have been unable to detect a correlation between expression and replication initiation/timing.

The majority of ARSs in budding yeast require sequences on the 3' side of the ACS (on the T-rich strand) collectively called "B-elements" [38, 42, 60]. Our data show that GC-ARSs also require flanking sequence on the 3' side of the GC-ACS motif (in the TYGAAC orientation) for ARS function. This result is supported by our mutARS-seq data where we detected a minor region of constrained nucleotides ~50 bp to the 3' side of the GC-ACS in ARS-C379 (FIG. 6B). The required flanking DNA lies distal to the TSS and may explain the extended nucleosome depletion regions seen at these loci.

Discussion

Faithful genome duplication is essential to all living organisms. Like many other cellular processes, DNA replication is primarily regulated at the initiation step. Understanding the regulation of initiation at replication origins is therefore key to understanding how different species replicate their genomes. The extensively studied yeasts *S. cerevisiae* and *S. pombe* have yielded great insights into origin function, but lack several properties exhibited by metazoan origins. For one, metazoan origins have G/C-rich signatures whereas all yeast origin sequence determinants described to date are NT-rich with the possible exception of fission yeast *S. japonicus*, where GC-rich motifs have been implicated in origin function through sequence analysis. Another key difference between yeast and metazoan origins is the connection between replication initiation and transcription. While promoter-associated origins tend to be early-firing in metazoans, this phenomenon has not been previously described in yeast. These discrepancies limit the value of most yeast species as models for the study of replication origins from higher eukaryotes. A better model would ideally possess the beneficial characteristics of yeast (genetic and molecular tools) while also recapitulating more of the traits displayed by metazoans.

In this study we generated a comprehensive profile of replication origins in *P. pastoris*, a budding yeast that is very distantly related to both the *S. cerevisiae* and *S. pombe* yeasts [61]. This methylotrophic budding yeast has traditionally been utilized as an industrial organism valued for its ability to convert methanol to biomass and for its ability to produce and secrete recombinant proteins in high yields [33]. An early study showed that two native *P. pastoris* ARSs did not function in *S. cerevisiae*, suggesting key mechanistic differences in replication initiation between the two species [37]. We identified 311 ARSs in *P. pastoris* and were able to delineate the essential functional regions to <200 bp in most cases. As in other budding yeasts we found PpARSs to reside predominantly in intergenic regions. However, unlike other studied yeasts, *P. pastoris* displayed a conserved G/C-rich motif (GC-ACS) in approximately 35% of its ARSs. In fact, almost all strong intergenic matches to this motif were isolated in our ARS screen, suggesting a causal role for this motif in origin function. We were unable to detect a strong conserved motif within the other origins (AT-ARSs). It is possible that the AT-ARSs function with an ill-defined sequence determinant similar to those seen in *S. pombe* and *L. kluyveri* [22, 28] or that the sequence required for AT-ARS function is innately elusive to traditional alignment-based methods due to its nucleotide composition.

To identify experimentally the nucleotides required for ARS function, we used mutARS-seq, a massively parallel approach that allows simultaneous measurement of the effects of all mutations on the function of an ARS [38]. This approach showed that the GC-ACS is indeed required for GC-ARS function (FIG. 6B). Notably, the GC-ACS was the most constrained element within the ARS tested, suggesting that this motif is the primary element used for ARS function and not a supporting element akin to *S. cerevisiae* "B-elements". The fact that the GC-ACS motif retains function within different plasmid contexts supports this hypothesis. The mutARS-seq experiment on ARS-A2772, an AT-ARS, revealed a very different region of functional constraint (FIG. 6C). A repetitive A/T-rich element was required for the function of this ARS. Other than its general A/T-richness, this element is significantly different from all previously identified ACS elements. Similarly to the GC-ACS, this motif is also the only strong region of functional constraint within the ARS and functions within different plasmid contexts, suggesting that it is a primary ARS element. While it is tempting to speculate that both of these motifs act as ORC binding sites (or in some other way recruit relevant protein factors), we have no direct evidence to this effect. To our knowledge *P. pastoris* is the first organism that simultaneously uses such diverse sequences as ARS elements.

The dynamics of replication in this species showed a surprising difference in replication timing between GC-ARSs and AT-ARSs (FIG. 10). While both types of origins exist within replication peaks, as a class, GC-ARS sites replicate significantly earlier and/or more efficiently than AT-ARS sites—although there are individual exceptions to this general categorization (FIG. 10B). Our data also show that while the timing/efficiency of AT-ARS benefits from clustering with other ARSs, GC-ARSs are not affected by clustering, suggesting that they are operating at maximal initiation potential. While it is not yet clear how such a hierarchy of replication timing is achieved mechanistically, in metazoan cells promoter-associated origins fire earlier than the others and this difference is usually attributed to increased chromatin accessibility at transcription start sites [1]. Our findings are consistent with the difference in timing being associated with differences in chromatin structure. We assayed global positioning of nucleosomes in *P. pastoris* by sequencing mononucleosomal DNA from MNase-treated chromatin. The results of this experiment showed an atypical pattern of nucleosome depletion at GC-ARSs that resembles the depletion pattern seen at TSSs, but with two additional nucleosomes depleted upstream of the TSS. In contrast, nucleosome depletion at AT-ARSs resembles the *S. cerevisiae* ARS pattern with a single nucleosome depleted close to the location of the A/T-rich functional element. It should also be noted that while the A/T-rich motif identified by mutARS-seq is essential for the function of ARS-A2772, it is possible that other AT-ARSs use other elements. This possibility is supported by the fact that many AT-ARSs do not have strong matches to the motif generated from the mutARS-seq data despite showing a nucleosome depletion region at the site of best match.

Combined, our findings suggest that *P. pastoris* can utilize at least two distinct sequences for origin selection and activation. One group of origins is A/T-rich and their replication times are distributed across S phase. The other type of origin is G/C-rich, disproportionally early replicating, and shows a close association with transcription start sites, properties usually associated with metazoan origins. In fact, the conserved motif required for GC-ARS firing is a very close match to the binding site of the human Hsf1 transcriptional activator [34]. Additionally, we have detected a statistical association between GC-ACS motifs and genes likely to be regulated by Hsf1 or its homologs. While the mechanistic nature of GC-ARS function will require additional investigation, our data could suggest that the Hsf1 binding site in *P. pastoris* is capable of recruiting either directly or indirectly the replication initiation machinery. Our data also suggest that transcription per se may not be required for GC-ARS function, as sequences between the GC-ACS and transcription start sites are not required for ARS function, but are likely to be required for transcription. Consistent with this model, we have not been able to detect a correlation between gene expression and replication timing, but this lack of correlation may also be due to a combination of subtle regulation patterns and scarcity of available expression data. It is worth noting that the GC-ACS motif does not match the well-defined *S. cerevisiae* Hsf1 binding site that has the sequence structure TTCTAGAAnnTTCT [62] (SEQ ID NO: 62) and is often represented as three evenly-spaced trinucleotides TTCnnGAAnnTTC [59] (SEQ ID NO: 63). However, Hsf1 is known to directly regulate genes lacking this motif, suggesting an ability to interact with diverse sequences [58]. Barring a mis-annotation, it is possible that in *P. pastoris* at least one of the four Hsf1 homologs is able to interact with and recruit ORC whereas the single Hsf1 protein in *S. cerevisiae* cannot bind to this atypical motif and thus relies exclusively on A/T-rich ARSs. This hypothesis would imply that the ability to use GIG-rich motifs for replication initiation is an ancestral trait that was lost in the lineage leading to the *Saccharomyces, Lachancea,* and *Kluyveromyces* clades. Whether other budding yeasts can utilize G/C-rich sites for initiation is not yet known. Alternatively, since a connection between Hsf1 and replication initiation has not yet been described, it is possible that this novel function is specific to the *Pichia* (*Komagataella*) genus, or perhaps only *P. pastoris*. Another observation that points to this motif being used for multiple functions is that a G/C-rich motif constructed from mutARS-seq data (FIG. 6B) is less information-rich than the motif obtained from alignment (contrary to the case of the A/T-rich motif which is difficult to produce by alignment, but is very obvious in the mutARS-seq data). While the optimal bases within the mutARS-seq data perfectly match the alignment-based motif, the cost of changing to a sub-optimal nucleotide is lower at most positions than the alignment-based motif would suggest. This observation can be explained by hypothesizing that this GC-motif is used for both origin activity as well as transcriptional regulation. If transcriptional regulation of the genes affected by this motif is evolutionarily more constrained than is ARS activity, then we would expect that the G/C-rich motifs would be selected upon primarily for their regulatory function.

Additionally, it is possible that GC-ACS motifs act as enhancer elements to other, potentially A/T-rich primary elements. Transcription factors such as Fkh1, Abf1, and Mcm1 have been previously shown to enhance origin activity in *S. cerevisiae* [10-12]. This model would argue that the G/C-rich motif does not act as a primary site of initiation, but enables nearby dormant elements to initiate DNA replication possibly through the chromatin-modifying activity of Hsf1. However, the fact that approximately one-third of all active origins have the same G/C-rich motif and that almost all intergenic occurrences of this motif are in ARSs is very different from what has been previously observed in other yeast models where connections between ARSs and transcription factors are much less obvious.

In addition to elucidating the features of replication dynamics, our data offer useful tools and data resources for this industrially important yeast. We anticipate that our nucleosome position map will be useful for studies of chromatin and gene expression, especially when combined with transcriptome data [55, 63]. More practically, replication origins are regulators of genome duplication and cell cycle progression, and are essential for episomal plasmid maintenance [64]. Current episomal vectors used in *P. pastoris* contain the original PARS1 (ARS-B413 in our data), an ARS discovered almost three decades ago [37, 65]. Our data show that PARS1 is one of the less efficient AT-ARSs [64], suggesting that using a different ARS may result in improvements in plasmid stability. Previously, we used mutARS-seq data to optimize ARS function in *S. cerevisiae* [38] and this approach can potentially be used to further improve plasmid maintenance in *P. pastoris*, facilitating strain engineering efforts in this system.

Materials and Methods

Strains, Plasmids, and Reagents.

The *P. pastoris* strain used in these studies was JC308 (James Gregg), a ura3 auxotroph of the GS115 background strain. All yeast growth was performed at 30; all bacterial growth was performed at 37. The plasmid vectors used in this study were previously described [38]. All *E. coli* work was done using Alpha-Select Gold Efficiency competent cells (Bioline). All enzymes used were from New England Biolabs unless otherwise noted. Primers were purchased from IDT unless otherwise noted. PCR purification and purification of digested plasmids was done using the DNA Clean and Concentrator-5 Kit (Zymo Research). Plasmid DNA was purified using the Wizard Plus SV Miniprep Kit (Promega).

ARS-Seq and miniARS-Seq.

ARS-seq and miniARS-seq screens were performed largely as described [38]. *P. pastoris* genomic DNA was isolated from cells grown in YPD using a phenol/chloroform bead-disruption method followed by ultracentrifugation in a CsCl gradient (to remove mitochondrial DNA) followed by EtOH precipitation. Genomic DNA was fragmented and ligated as described [38]. Cloning efficiencies of resultant libraries were verified by colony PCR and *P. pastoris* cells were transformed with libraries using a custom lithium acetate protocol as follows. To make competent cells yeast were grown in YPG medium (10 g/L yeast extract, 20 g/L Peptone, 3% v/v glycerol) until $OD_{600}$ density of 1. Cells from 1 L of culture were spun down, rinsed and resuspended in 10 mL of TE/LiOAc (10 mM Tris-HCl, 1 mM EDTA, 100 mM lithium acetate). Cell suspensions were incubated at 30 with shaking for 30 minutes, dispensed into 100 μL aliquots and frozen at −80. For transformations competent cells were thawed at room temperature, mixed with 1-5 μg of plasmid DNA, 600 μL of "two-step" transformation buffer (40% polyethylene glycol-4000, 100 mM LiOAc, 10 mM Tris-HCl, 1 mM EDTA, 12 mM DTT, 0.12 mg/mL fish sperm carrier DNA) and incubated at 30 with gentle rotation for 30 minutes. The cell mixture was then heat-shocked at 42 for 30 minutes and plated. Cells were grown for five days, replica-plated, and grown for three more days before cells were pooled for plasmid extraction. DNA shearing for miniARS-seq, plasmid recovery from yeast, and Illumina sequencing were performed as described [38].

ARS-Seq and miniARS-Seq Sequence Analysis.

Illumina paired end sequencing reads were uniquely mapped to the GS115 genome [31] using Bowtie version 0.12.7. Custom Python scripts were used to detect relevant restriction sites at the ends of all mapped fragments that were extended to remove truncation products. Overlapping fragments were assembled into contigs. Contigs that had a combined read-depth of 1 were removed from the dataset. Cases where multiple discontinuous contigs were joined by overlapping fragments were manually resolved based on read depth. To maximize miniARS-seq data recovery, 101 bp paired end reads were mapped in full and unmapped reads were trimmed to 50 bp and mapped again. Resulting fragments with read depth >1 were assembled into contigs and contigs consisting of fewer than three unique fragments were removed. Both ARS-seq and miniARS-seq fragments were used to delineate minimal overlapping regions ("inferred functional cores"). To prevent data loss, cores that were <150 bp in length were extended bi-directionally to a final length of 150 bp.

mutARS-Seq.

mutARS-seq was performed largely as described [38]. Mutagenized oligos of ARS-C379 and ARS-A2772 were synthesized by Trilink Biotechnologies. The resulting libraries contained 24,000-40,000 ARS inserts. Yeast were transformed with mutagenized libraries as described above in two biological replicate pools each containing ~100,000 transformed colonies. After five days of growth on selective agar plates, colonies were pooled and inoculated into 1 L cultures of liquid selective medium. Cultures were grown for 36 hours with periodic dilution to prevent saturation. Samples were taken at 0, 12, 24, and 36 hours. Sequencing data were analyzed using the Enrich software package [66]. For maximum separation averaged data from the 36-hour samples are shown in FIG. 6. To create a position-weighted matrix from mutARS-seq data, the enrichment ratio values within the constrained region were converted into relative allele frequencies after an arbitrary cutoff minimum of 0.2 was applied. Logo images were generated using Weblogo software [67].

Site-Directed Mutagenesis.

ARS sequences bearing mutations (see accompanying Sequence Listing) were ordered as custom designed double stranded gBlock DNA fragments (Integrated DNA Technologies). The gBlocks were used as PCR templates to amplify the mutant alleles prior to cloning. Wild type ARS alleles were PCR amplified from the gDNA of the parent strain (JC308).

Conserved Motif Analysis.

The MEME de novo motif discovery tool [44] was applied to identify conserved motifs within the entire set of PpARSs using the 5th order Markov background model and the entire set of *P. pastoris* intergenic sequences. Both MAST [68] and FIMO [69] programs from the MEME suite were used to map motif occurrences within different sets of ARS sequences.

2D Gel Analysis.

A 1 L culture of *P. pastoris* was grown to early log phase in YEPD and harvested for genomic DNA isolation [70]. Approximately 8 μg of DNA was cleaved with NcoI or StuI to release genomic fragments of 4.575 kb or 4.043 kb containing ARS-C379 or the ARS-A2772, respectively. Replication intermediates were separated on a first dimension gel of 0.4% ME agarose in 1×TBE for 20 hours at 1 V/cm. Lanes for the second dimension gel were sliced from the gel and encased in a second gel of 0.9% ME agarose in 1×TBE with 0.3 μg/ml. Electrophoresis for the second dimension was carried out for 4.5 hours at 5.5 V/cm at 4° C. The genomic fragments were detected on Southern blots using $^{32}$P-dATP labeled PCR probes.

Replication Timing Measurements.

Replication timing experiments were performed largely as described [48]. Exponentially growing (in YPD medium) *P. pastoris* cells were subjected to flow sorting using standard techniques on a BD FACsAria II cell-sorter. The purity of each sorted sample was determined to be ~95%. Genomic DNA from 1.5-2 million G1 and S-phase cells was isolated using the YeaStar Genomic DNA Kit (Zymo Research). Randomly fragmented sequencing libraries were prepared using the Nextera DNA Sample Preparation Kit (Illumina) [71]. Approximately 29 million 50 bp reads were recovered for each sample of each replicate. More than 90% of the reads in all samples were mapped to the *P. pastoris* GS115 reference genome and ~1% of the reads in each sample were removed due to multiple mapping sites. After processing, 25-27 million reads were assigned to 1 kb bins across the genome resulting in average count-depth of 2936 reads/bin for G1 sample of replicate 1, 2796 reads/bin for G1 sample of replicate 2, 2843 reads/bin for S sample of replicate 1, and 2913 reads/bin for S sample of replicate 2. Reads were mapped using Bowtie and custom scripts were used to generate replication timing profiles as described [48]. The total number of reads for each replicate was equalized in each sample and a ratio of S/G1 reads was calculated for each replicate. These ratios were multiplied by 1.5 to account for the fact that the average cell in the middle of S-phase will have replicated half of its DNA. We fitted a loess curve to the mean of the two replicate ratio measurements, then found peaks along this curve using the turnpoints( ) function from the R package, pastecs. The resulting curves were normalized to a baseline value of 1.

Nucleosome Mapping.

Nucleosome positions were mapped similarly to the method described [53]. Two colonies were grown in 400 mL of YPD media until an $OD_{600}$ of 1 and then cross-linked with formaldehyde. The two samples were bead disrupted in 10 mM Tris-HCl pH8.0 with 1 mM $CaCl_2$. Visually lysed samples were then MNase digested for 30 minutes at increasing concentrations of MNase. Cross-links were removed by overnight incubation at 65 followed by DNA extraction with phenol/chloroform. Extracted DNA was separated using a 2% agarose gel to visualize the mononucleosome enriched band. DNA corresponding to ~150 bp was then extracted and sequenced using the Illumina HiSeq platform. The samples were divided in half to provide technical replicates.

Supplemental Notes on Methods & Results

Nucleosome profile of *P. pastoris*. Nucleosome density was plotted for sites centered on all TSSs as a control to test the overall quality of the mapping data, non-overlapping GC-ARS sites with a single match to the GC-ACS, or the A/T-rich motif shown in FIG. 6C. TSS sites are ranked based on expression in the SDEG condition [55]. GC-ARS and AT-ARS sites are ranked by the strength of the best match to the G/C- and the A/T-rich motif respectively.

Sequence features of GC-ARSs. Average nucleotide frequencies around 107 GC-ARS sites and twenty-eight non-ARS intergenic occurrences of the GC-ACS, were centered on the best match of the GC-ACS. The nucleotide frequencies were calculated at all flanking regions around the motif independent of whether the flanking region is present in ARS contigs or cores. The distribution of distances between the GC-ACS motif and the TSS for adjacent genes transcribing away from the ARS with available TSS annotations. Distances to the 5' side of the motif, and distances to the 3' side of the motif were noted. The distribution of sequence lengths was noted between the GC-ACS and the end of the inferred functional core region for each GC-ARS.

Accession Numbers

All sequencing data presented are available from the National Center for Biotechnology Information Sequence Read Archive (ARS-seq-SRP031643; miniARS-seq-SRP031646; mutARSseq-SRP031760; replication timing-SRP031759; nucleosome mapping-SRP031651).

TABLE 2

Sequences of ARS mutagenized in FIG. 5

| fragment_name | chrom | start | end | length | Combined_rd | fxn |
|---|---|---|---|---|---|---|
| Manual validation summary (SEQ ID NO: 20-35, respectively) | | | | | | |
| 1_1843383_1843731 | 1 | 1843383 | 1843731 | 348 | 5 | No |
| 1_713599_713789 | 1 | 713599 | 713789 | 190 | 6 | No |
| 2_3962_4915 | 2 | 3962 | 4915 | 953 | 6 | very weak |
| 3_499687_499988 | 3 | 499687 | 499988 | 301 | 6 | No |
| 4_341217_341721 | 4 | 341217 | 341721 | 504 | 6 | No |
| 3_1970779_1970969 | 3 | 1970779 | 1970969 | 190 | 7 | No |
| 2_970074_970511 | 2 | 970074 | 970511 | 437 | 8 | No |
| 2_2281275_2281434 | 2 | 2281275 | 2281434 | 159 | 8 | No |
| 1_2060258_2060474 | 1 | 2060258 | 2060474 | 216 | 9 | No |
| 4_1647690_1648691 | 4 | 1647690 | 1648691 | 1001 | 9 | weak |
| 1_197_4023 | 1 | 197 | 4023 | 3826 | 10 | weak |
| 1_278500_281500 | 1 | 278500 | 281500 | 3000 | manual | No |
| 1_315141_318141 | 1 | 315141 | 318141 | 3000 | manual | very weak |
| 3_267500_270500 | 3 | 267500 | 270500 | 3000 | manual | No |
| 4_684500_687500 | 4 | 684500 | 687500 | 3000 | manual | weak |
| 4_1047500_1050500 | 4 | 1047500 | 1050500 | 3000 | manual | No |
| Candidate ARSs and mutant variants tested (FIG. 5; SEQ ID NO: 36-59, respectively) | | | | | | |
| A76_WT | 1 | 76846 | 76970 | 125 | 38076 | Yes |
| A76_MUT | 1 | 76846 | 76970 | 125 | 38076 | No |
| A366_WT | 1 | 366441 | 366565 | 125 | 26366 | Yes |
| A366_MUT | 1 | 366441 | 366565 | 125 | 26366 | No |
| A405_WT | 1 | 405388 | 405512 | 125 | 5389 | Yes |
| A405_MUT | 1 | 405388 | 405512 | 125 | 5389 | No |
| A427_WT | 1 | 427956 | 428080 | 125 | 16604 | Yes |
| A427_MUT | 1 | 427956 | 428080 | 125 | 16604 | No |
| B864_WT | 2 | 864224 | 864348 | 125 | 8405 | Yes |
| B864_MUT | 2 | 864224 | 864348 | 125 | 8405 | No |
| B1605_WT | 2 | 1605269 | 1605145 | 125 | 55795 | Yes |
| B1605_MUT | 2 | 1605269 | 1605145 | 125 | 55795 | No |
| B1739_WT | 2 | 1739383 | 1739507 | 125 | 19427 | Yes |
| B1739_MUT | 2 | 1739383 | 1739507 | 125 | 19427 | No |
| C562_WT | 3 | 562487 | 562611 | 125 | 22676 | Yes |
| C562_MUT | 3 | 562487 | 562611 | 125 | 22676 | No |
| C937_WT | 3 | 937624 | 937500 | 125 | 14995 | Yes |
| C937_MUT | 3 | 937624 | 937500 | 125 | 14995 | No |
| C1122_WT | 3 | 1122505 | 1122381 | 125 | 6298 | Yes |
| C1122_MUT | 3 | 1122505 | 1122381 | 125 | 6298 | No |
| D258_WT | 4 | 258716 | 258840 | 125 | 8990 | Yes |
| D258_MUT | 4 | 258716 | 258840 | 125 | 8990 | No |
| D781_WT | 4 | 781423 | 781547 | 125 | 7714 | Yes |
| D781_MUT | 4 | 781423 | 781547 | 125 | 7714 | No |

References Cited in Example 2

1. Méchali M (2010) Nat Rev Mol Cell Biol 11: 728-738.
2. Eaton M L, et al. (2011) Genome Res 21: 164-174.
3. Dellino G I, et al. (2013) Genome Res 23: 1-11.
4. Costas C, et al. (2011) Nat Struct Mol Biol 18: 395-400.
5. Hansen R S, et al. (2010) Proc Natl Acad Sci USA 107: 139-144.
6. Méchali M, et al. (2013) Curr Opin Genet Dev 23: 124-131.
7. Cayrou C, et al. (2011) Genome Res 21: 1438-1449.
8. Stinchcomb D T, et al. (1979) Nature 282: 39-43.
9. Bell S P, Dutta A (2002) Annu Rev Biochem 71: 333-374.
10. Chang V K, et al. (2004) Mol Cell Biol 24: 6514-6524.
11. Walker S S, et al. (1989) Mol Cell Biol 9: 2914-2921.
12. Knott S R V, et al. (2012) Cell 148: 99-111.
13. Eaton M L, et al. (2010) Genes Dev 24: 748-753.
14. Berbenetz N M, et al. (2010) PLoS Genet 6. doi:10.1371/journal.pgen.1001092.
15. Lin S, Kowalski D (1997) Mol Cell Biol 17: 5473-5484.
16. Donaldson A D, et al. (1998) Mol Cell 2: 173-182.
17. Koren A, et al. (2010) PLoS Genet 6: e1001068.
18. Mantiero D, et al. (2011) EMBO J 30: 4805-4814.
19. Bechhoefer J, Rhind N (2012) Trends Genet 28: 374-381.
20. de Moura A P S, et al. (2010) Nucleic Acids Res 38: 5623-5633.
21. Chuang R Y, Kelly T J (1999) Proc Natl Acad Sci USA 96: 2656-2661.
22. Dai J, et al. (2005) Proc Natl Acad Sci USA 102: 337-342.
23. Patel P K, et al. (2006) Mol Biol Cell 17: 308-316.
24. Ryba T, et al. (2011) PLoS Comput Biol 7: e1002225.
25. Delgado S, et al. (1998) EMBO J 17: 2426-2435.
26. MacAlpine H K, et al. (2010) Genome Res 20: 201-211.
27. Liachko I, et al. (2010) PLoS Genet 6: e1000946.
28. Liachko I, et al. (2011) BMC Genomics 12: 633.
29. Di Rienzi S C, et al. (2012) Genome Res 22: 1940-1952.
30. Xu J, et al. (2012) Genome Biol 13: R27.
31. De Schutter K, et al. (2009) Nat Biotechnol 27: 561-566.
32. Kurtzman C P (2009) J Ind Microbiol Biotechnol 36: 1435-1438.
33. Macauley-Patrick S, et al. (2005) Yeast 22: 249-270.
34. Anckar J, Sistonen L (2011) Annu Rev Biochem 80: 1089-1115.
35. Chan C S, Tye B K (1980) Proc Natl Acad Sci USA 77: 6329-6333.
36. Tanaka S, et al. (1996) Yeast 12: 101-113.
37. Cregg J M, et al. (1985) Mol Cell Biol 5: 3376-3385.
38. Liachko I, et al. (2013) Genome Res 23: 698-704.
39. Keich U, et al. (2008) BMC Bioinformatics 9: 372.
40. Ng P, Keich U (2008) Bioinformatics 24: 2256-2257.
41. Breier A M, et al. (2004) Genome Biol 5: R22.
42. Nieduszynski C A, et al. (2006) Genes Dev 20: 1874-1879.
43. Bhaskar A, Keich U (2010) Stat Appl Genet Mol Biol 9: Article28.
44. Bailey T L, Elkan C (1994) Proc Int Conf Intel! Syst Mol Biol 2: 28-36.
45. Brewer B J, Fangman W L (1987) Cell 51: 463-471.
46. Fowler D M, et al. (2010) Nat Methods 7: 741-746.
47. Patwardhan R P, et al. (2009) Nat Biotechnol 27: 1173-1175.
48. Müller C A, Nieduszynski C A (2012) Genome Res. doi:10.1101/gr.139477.112.
49. Müller C A, et al. (2013) Nucleic Acids Res. doi: 10.1093/nar/gkt878.
50. Müller P, et al. (2010) Genes Dev 24: 1418-1433.
51. Lantermann A B, et al. (2010) Nat Struct Mol Biol 17: 251-257.
52. Lubelsky Y, et al. (2011) Nucleic Acids Res 39: 3141-3155.
53. Lee W, et al. (2007) Nat Genet 39: 1235-1244.
54. Tsankov A M, et al. (2010) PLoS Biol 8: e1000414.
55. Liang S, et al. (2012) BMC Genomics 13: 738.
56. Wang J, et al. (2012) Genome Res 22: 1798-1812.
57. Yuan G-C, et al. (2005) Science 309: 626-630.
58. Hahn J-S, et al. (2004) Mol Cell Biol 24: 5249-5256.
59. Trinklein N D, et al. (2004) Mol Biol Cell 15: 1254-1261.
60. Shirahige K, et al. (1993) Mol Cell Biol 13: 5043-5056.
61. Dujon B (2010) Nat Rev Genet 11: 512-524.
62. Harbison C T, et al. (2004) Nature 431: 99-104.
63. Gasser B, et al. (2007) BMC Genomics 8: 179.
64. Liachko I, Dunham M J (2013) FEMS Yeast Res. doi:10.1111/1567-1364.12123.
65. Lee C C, et al. (2005) Plasmid 54: 80-85.
66. Fowler D M, et al. (2011) Bioinformatics. doi:10.1093/bioinformatics/btr577.
67. Crooks G E, et al. (2004) Genome Res 14: 1188-1190.
68. Bailey T L, Gribskov M (1998) Bioinformatics 14: 48-54.
69. Grant C E, et al. (2011) Bioinformatics 27: 1017-1018.
70. Huberman J A (1997) Methods 13: 247-257.
71. Adey A, et al. (2010) Genome Biol 11: R119.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A recombinant or synthetic nucleic acid molecule selected from the group consisting of SEQ ID NO:1-3, 5-10 and SEQ ID NO:12-19, wherein the nucleic acid molecule includes one or more mutations relative to the corresponding wild type sequence (SEQ ID NO: 11-13, or 16), and wherein the one or more mutations are selected from the optional bases of SEQ ID NO:1-3, 5, 14-15, and 17-18.

2. The nucleic acid molecule of claim 1, which comprises SEQ ID NO: 1 and wherein the nucleic acid sequence contains at least 2 mutations selected from the optional bases presented in SEQ ID NO: 1 relative to the corresponding wild type sequence shown in SEQ ID NO: 10.

3. The nucleic acid molecule of claim 1, which is SEQ ID NO: 6 or 7.

4. The nucleic acid molecule of claim 1, which is SEQ ID NO: 5 and wherein the nucleic acid sequence contains at least 2 mutations selected from the optional bases presented in SEQ ID NO: 5 relative to the corresponding wild type sequence shown in SEQ ID NO: 13.

5. The nucleic acid molecule of claim 1, which is SEQ ID NO: 9 or 19.

6. A plasmid comprising the nucleic acid molecule of claim 1.

7. A yeast cell comprising the nucleic acid molecule of claim 1.

8. The yeast cell of claim 7, which is a member of the genera consisting of *Saccharomyces, Lachancea, Kluyveromyces,* and *Pichia (Komagataella)*.

9. The yeast cell of claim 7, which is selected from the group consisting of *Saccharomyces cerevisiae, Saccharomyces bayanus, Saccharomyces paradoxus, Lachancea kluyveri, Lachancea waltii, Kluyveromyces lactis, Kluyveromyces wickerhammii, Hansenula polymorpha, Pichia pastoris,* and *Naumovozyma castellii*.

10. The yeast cell of claim 9, which is *Pichia pastoris*, and wherein the nucleic acid molecule is SEQ ID NO: 9 or 19.

11. A method of producing stable plasmid replication in a yeast cell, the method comprising transforming the plasmid of claim 6 into the yeast cell.

12. The method of claim 11, wherein the yeast cell is a member of the genera consisting of *Saccharomyces, Lachancea, Kluyveromyces,* and *Pichia (Komagataella)*.

13. The method of claim 11, wherein the yeast cell is selected from the group consisting of *Saccharomyces cerevisiae, Saccharomyces bayanus, Saccharomyces paradoxus, Lachancea kluyveri, Lachancea waltii, Kluyveromyces lactis, Kluyveromyces wickerhammii, Hansenula polymorpha, Pichia pastoris,* and *Naumovozyma castellii*.

14. The method of claim 13, wherein the yeast cell is *Pichia pastoris*, and wherein the nucleic acid molecule is SEQ ID NO: 9 or 19.

15. A method of enhancing plasmid replication in a yeast cell, the method comprising transforming the plasmid of claim 6 into the yeast cell.

16. The method of claim 15, wherein the yeast cell is a member of the genera consisting of *Saccharomyces, Lachancea, Kluyveromyces,* and *Pichia (Komagataella)*.

17. The method of claim 15, wherein the yeast cell is selected from the group consisting of *Saccharomyces cerevisiae, Saccharomyces bayanus, Saccharomyces paradoxus, Lachancea kluyveri, Lachancea waltii, Kluyveromyces lactis, Kluyveromyces wickerhammii, Hansenula polymorpha, Pichia pastoris,* and *Naumovozyma castellii*.

18. The method of claim 17, wherein the yeast cell is *Pichia pastoris*, and wherein the nucleic acid molecule is SEQ ID NO: 9 or 19.

19. A method of producing a shuttle vector for use in multiple species of yeast, the method comprising introducing the nucleic acid molecule of claim 1 into a plasmid.

20. The method of claim 19, wherein the plasmid is pRS406.

* * * * *